(12) United States Patent
Low et al.

(10) Patent No.: US 10,347,843 B2
(45) Date of Patent: Jul. 9, 2019

(54) ORGANIC ELECTRONIC MATERIAL

(71) Applicants: GUANGDONG AGLAIA OPTOELECTRONIC MATERIALS CO., LTD., Foshan, Guangdong (CN); BEIJING AGLAIA TECHNOLOGY DEVELOPMENT CO., LTD., Beijing (CN)

(72) Inventors: Kam-Hung Low, Foshan (CN); Zhe Li, Foshan (CN); Jinxin Chen, Foshan (CN); Lifei Cai, Beijing (CN)

(73) Assignees: GUANGDONG AGLAIA OPTOELECTRONIC MATERIALS CO., LTD., Foshan (CN); BEIJING AGLAIA TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 15/557,097

(22) PCT Filed: Sep. 1, 2015

(86) PCT No.: PCT/CN2015/088709
§ 371 (c)(1),
(2) Date: Sep. 11, 2017

(87) PCT Pub. No.: WO2016/141691
PCT Pub. Date: Sep. 15, 2016

(65) Prior Publication Data
US 2018/0047909 A1 Feb. 15, 2018

(30) Foreign Application Priority Data
Mar. 9, 2015 (CN) .......................... 2015 1 0102569

(51) Int. Cl.
| | |
|---|---|
| *H01L 51/00* | (2006.01) |
| *C07C 13/567* | (2006.01) |
| *C07C 13/573* | (2006.01) |
| *C09K 11/06* | (2006.01) |
| *C07C 13/72* | (2006.01) |
| *C07D 213/06* | (2006.01) |

(Continued)

(52) U.S. Cl.
CPC ........ *H01L 51/0058* (2013.01); *C07C 13/567* (2013.01); *C07C 13/573* (2013.01); *C07C 13/72* (2013.01); *C07D 213/06* (2013.01); *C07D 213/16* (2013.01); *C09B 1/00* (2013.01); *C09K 11/06* (2013.01); *H01L 51/0052* (2013.01); *H01L 51/0056* (2013.01); *C07C 2603/18* (2017.05); *C07C 2603/24* (2017.05); *C07C 2603/94* (2017.05); *C07C 2603/97* (2017.05); *C09K 2211/1007* (2013.01); *C09K 2211/1011* (2013.01); *H01L 51/5012* (2013.01); *Y02E 10/549* (2013.01)

(58) Field of Classification Search
None
See application file for complete search history.

(56) References Cited

U.S. PATENT DOCUMENTS

| 8,426,035 B2* | 4/2013 | Kwong | ................ | C07D 345/00 |
|---|---|---|---|---|
| | | | | 428/690 |
| 2012/0091885 A1 | 4/2012 | Kim et al. | | |

(Continued)

FOREIGN PATENT DOCUMENTS

| CN | 102449109 A | 5/2012 |
|---|---|---|
| JP | 2003-229273 A | 8/2003 |

(Continued)

*Primary Examiner* — Tam M Nguyen
(74) *Attorney, Agent, or Firm* — Maschoff Brennan

(57) ABSTRACT

The present invention discloses an "organic electronic material", belonging to the organic light-emitting device (OLED) display materials field. The organic electronic material in the present invention has a structural formula (I), having good thermal stability, high luminous efficiency, high purity of light emission. The OLED made by this kind of organic light-emitting material has the advantages of excellent organic light-emitting efficiency, excellent color purity and long service life.

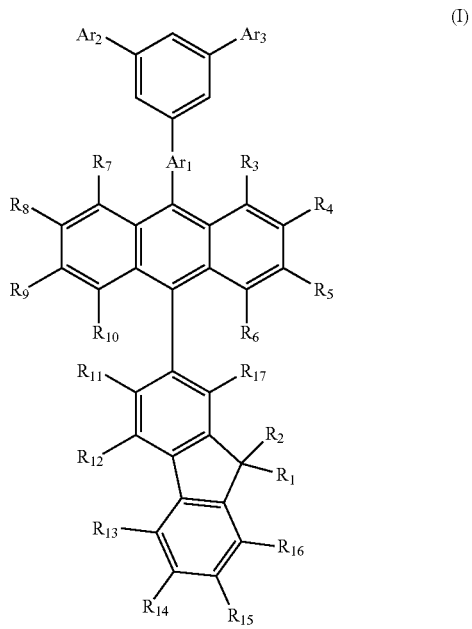

6 Claims, 5 Drawing Sheets

(51) Int. Cl.
*C07D 213/16* (2006.01)
*C09B 1/00* (2006.01)
*H01L 51/50* (2006.01)

(56) References Cited

U.S. PATENT DOCUMENTS

2017/0029278 A1* 2/2017 Fasel ........................ C23C 16/44
2018/0175313 A1* 6/2018 Loo ........................... C09K 9/02

FOREIGN PATENT DOCUMENTS

| KR | 10-2009-0041999 A | 4/2009 |
| KR | 10-2009-0065201 A | 6/2009 |
| KR | 10-2011-0081698 A | 7/2011 |

* cited by examiner

ORGANIC ELECTRONIC MATERIAL

TECHNICAL FIELD

This invention relates to a new type of organic light-emitting material. By deposited into thin film through vacuum evaporation, it is used in organic light emitting diodes as a blue light-emitting material. It belongs to the Organic Light-emitting Device (OLED) display material field.

BACKGROUND ART

OLED, as a new type of display technology, has unique advantages such as self-illumination, wide viewing angle, low power consumption, high efficiency, thin, rich colors, fast response, extensive application temperature, low drive voltage, used to make flexible, bendable and transparent display panel and environmental friendliness, etc. Therefore, OLED technology can be applied to flat panel displays and new generation of lighting, or can be used as backlight of LCD.

OLED is a device made through spin-coating or depositing a layer of organic material between two metal electrodes. A classic three-layer OLED comprises a hole transport layer, a light emitting layer and an electron transport layer. The holes generating from the anode through the hole transport layer and the electrons generating from the cathode through the electron transport layer combine to form excitons in the light emitting layer, emitting light. By changing the material of the light emitting layer, the OLED can emit red light, green light and blue light. Therefore, stable, efficient organic light-emitting materials with pure colors play an important role in the application and promotion of OLEDs. Meanwhile, it is also very urgent for the application and promotion of large area of panel display in OLEDs.

Among three primary colors (red, blue, green), the red and green light materials have made great development, which also meet the market demands of the panels. There are a series of commercially available materials for the blue light materials, and distyryl-biphenyl (DPVBi) compounds produced by Idemitsu are widely used in the early period. The devices made by this type of compound have high efficiency, but these materials often have poor stability, and even worse, this type of compound often emits sky blue light, and often y>0.15 of the CIE value. Therefore, its poor stability and impure color greatly restrict the application of this type of compounds in the full-color display devices. Another type of blue-light material is the Kodak ADN and tetra-butyl perylene, but their luminous efficiency is relatively poor, thus, it cannot be widely used.

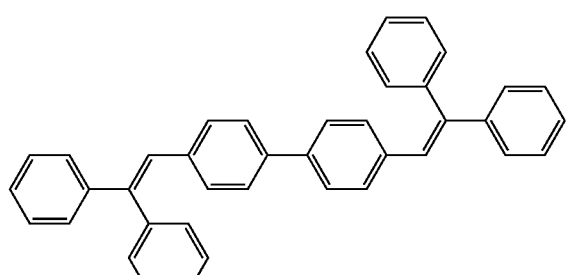

(DPVBi)

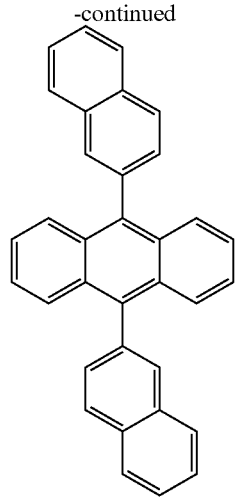

(ADN)

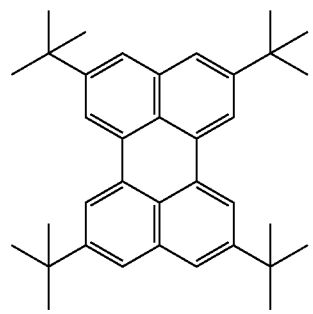

(Tetra-tert-butyl perylene)

SUMMARY OF THE INVENTION

In the present invention, a series of organic blue light-emitting materials with good thermal stability, high luminous efficiency, high purity of light-emitting are provided, to overcome the deficiencies of the above compounds. The OLEDs prepared thereof have the advantages of good electroluminescent efficiency, excellent color purity and long lifetime.

The said organic electronic material has the following structural formula (I):

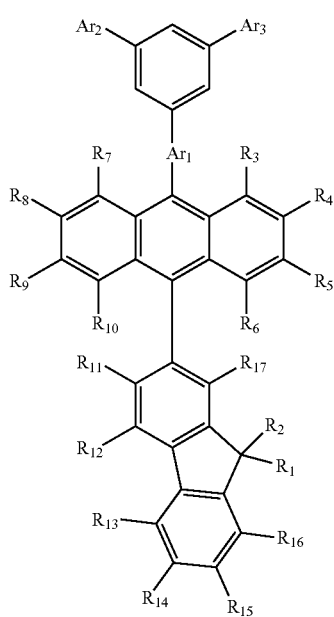

(I)

Wherein R₁-R₁₇ independently represent hydrogen, deuterium, halogen, cyano, nitro, C1-C8 alkyl, C1-C8 alkoxy, C6-C30 substituted or unsubstituted aryls, C3-C30 substituted or unsubstituted aryls containing one or more heteroatoms, C2-C8 substituted or unsubstituted alkenyl, C2-C8 substituted or unsubstituted alkynyl, wherein Ar₁-Ar₃ independently represent C6-C60 substituted or unsubstituted aryl, C3-C60 substituted or unsubstituted heteroaryl containing one or more heteroatoms, triaryl (C6-C30) amine.

Preferably, wherein R₁-R₁₇ independently represent hydrogen, halogen, cyano, nitro, C1-C8 alkyl, C1-C8 alkoxy, C2-C8 substituted or unsubstituted alkenyl, C2-C8 substituted or an unsubstituted alkynyl, C1-C4 alkyl substituted or unsubstituted phenyl, C1-C4 alkyl substituted or unsubstituted naphthyl, or combined C1-C4 alkyl substituted or unsubstituted fluorenyl; Ar₁-Ar₃ independently represent C1-C4 alkyl or C6-C30 aryl-substituted phenyl, C1-C4 alkyl or C6-C30 aryl-substituted naphthyl, phenyl, naphthyl, pyridyl, N—C6-C30 aryl or C1-C4 alkyl-substituted carbazolyl, dibenzothienyl, dibenzofuranyl, anthryl, phenanthryl, pyrenyl, perylenyl, fluoranthenyl, (9,9)-dialkyl) fluorenyl, (9,9-dialkyl substituted or unsubstituted aryl) fluorenyl, 9,9-spirofluorenyl.

Preferably, wherein R₁-R₂ independently and preferably represent hydrogen, halogen, C1-C4 alkyl, C1-C4 alkyl substituted or unsubstituted phenyl, C1-C4 alkyl substituted or unsubstituted naphthyl, or combined C1-C4 alkyl-substituted or unsubstituted fluorenyl; wherein R₃-R₁₇ may independently represent hydrogen, halogen, C1-C4 alkyl, C1-C4 alkyl substituted or unsubstituted phenyl, C1-C4 alkyl-substituted or unsubstituted naphthyl, preferably Ar₁-Ar₃ independently represent phenyl, tolyl, xylyl, t-butylphenyl, naphthyl, pyridyl, methyl naphthalene, biphenyl, diphenylphenyl, naphthylphenyl, diphenylbiphenyl, diarylamine phenyl, N-phenylcarbazolyl, (9,9-dialkyl) fluorenyl, (9,9-dialkyl substituted or unsubstituted phenyl) fluorenyl, 9,9-spirofluorenyl.

Preferably, wherein R₃-R₁₇ preferably represents hydrogen, and R₁ and R₂ may independently represent hydrogen, methyl, ethyl, propyl, isopropyl, t-butyl, phenyl, biphenyl, naphthyl, or combined fluorenyl; Ar₁-Ar₃ may independently represent phenyl, pyridyl, tolyl, xylyl, naphthyl, methylnaphthalene, biphenyl, diphenylphenyl, naphthylphenyl, diphenylbiphenyl, (9,9-dialkyl) fluorenyl, (9,9-dimethyl-substituted or unsubstituted phenyl) fluorenyl, 9,9-spirofluorenyl.

Preferably, R₃-R₁₇ represent hydrogen preferably; R₁, R₂ independently represent hydrogen, methyl or combined fluorenyl; Ar₁, Ar₂, Ar₃ independently represent phenyl and naphthyl.

Preferably,

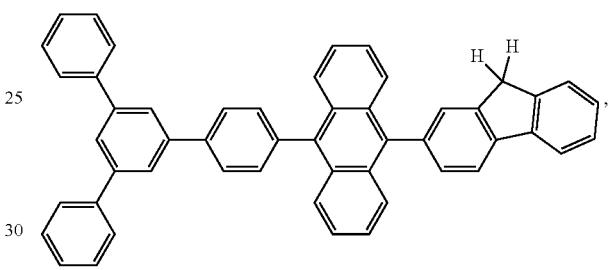

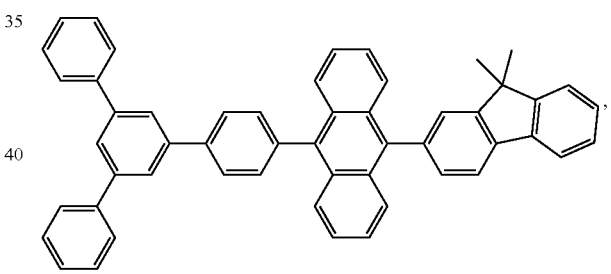

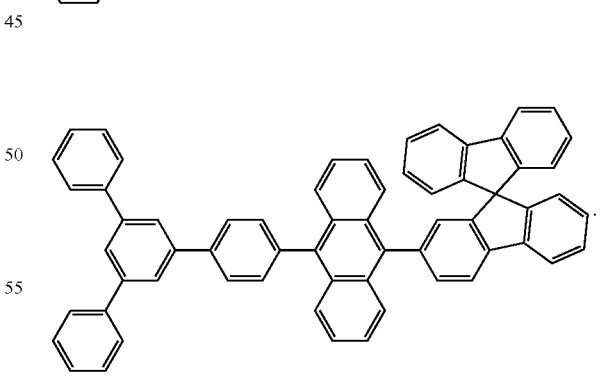

The applications of the above said organic electronic material in such fields as organic light-emitting devices, organic solar cells, organic thin-film transistors or organic photoreceptors.

As mentioned above, the specific embodiments in the invention are as follows, but not limited to the structures as below:

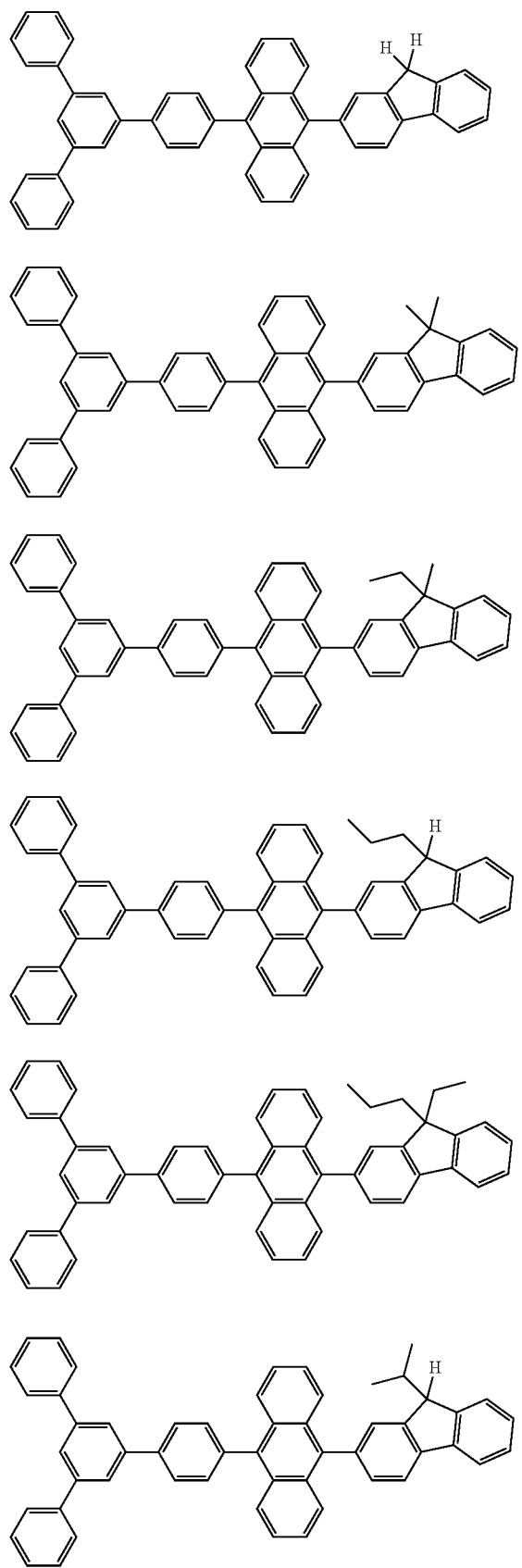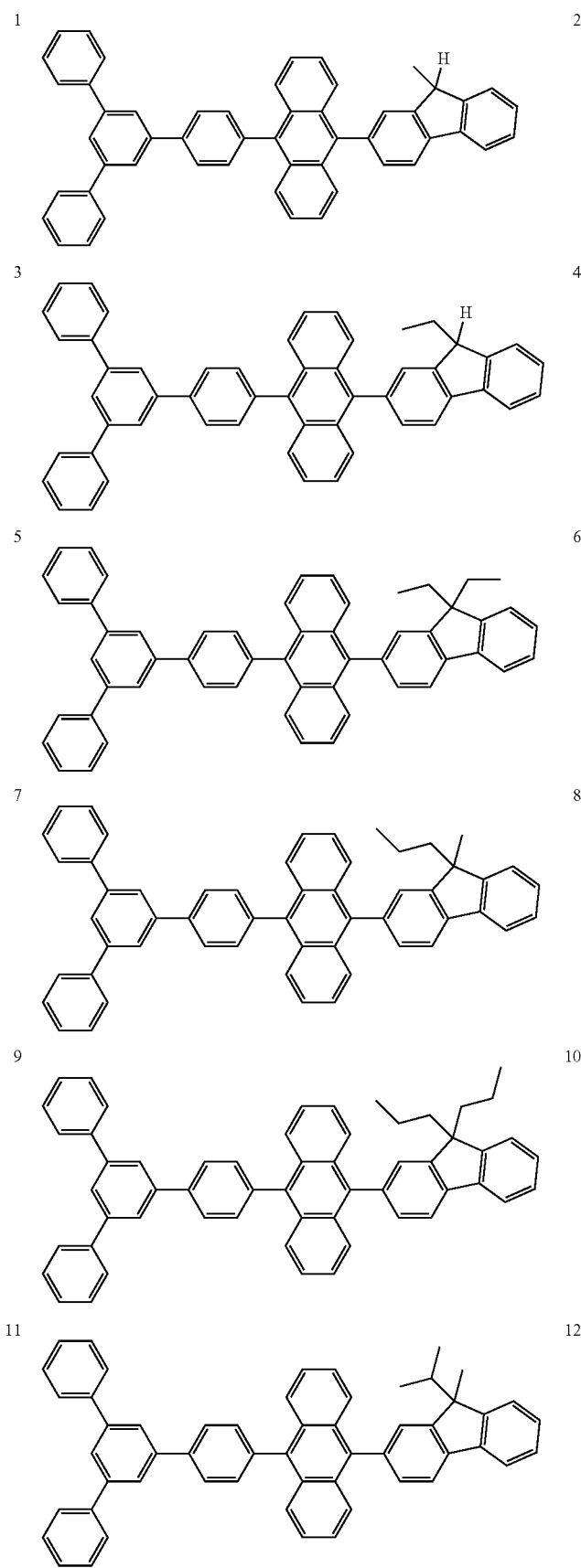

-continued
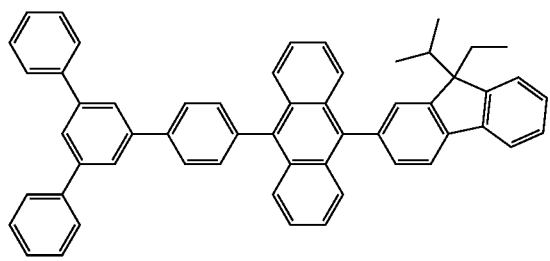
13
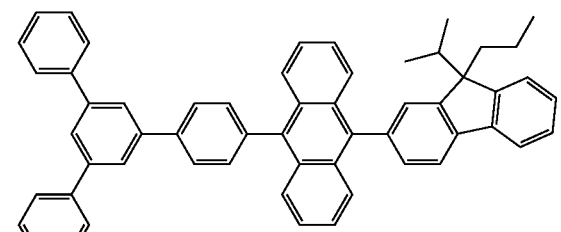
14
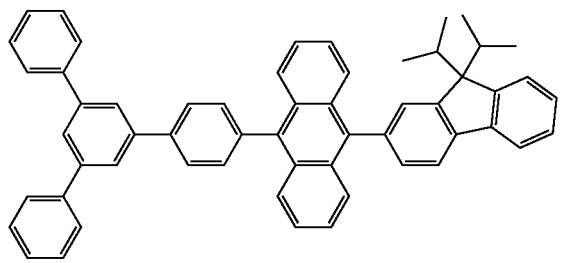
15
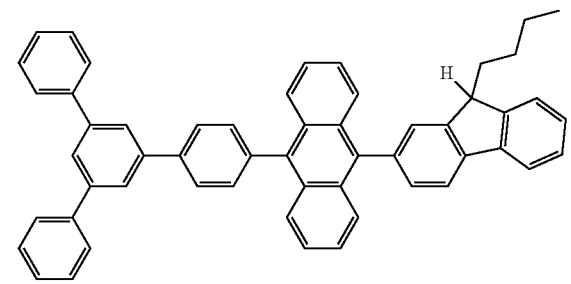
16
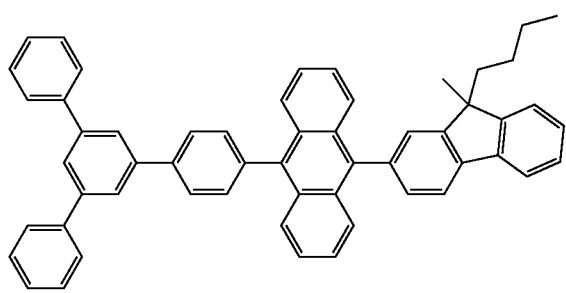
17
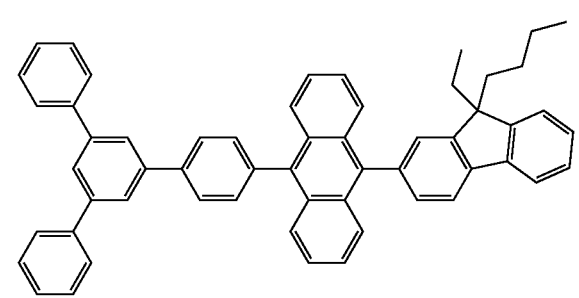
18
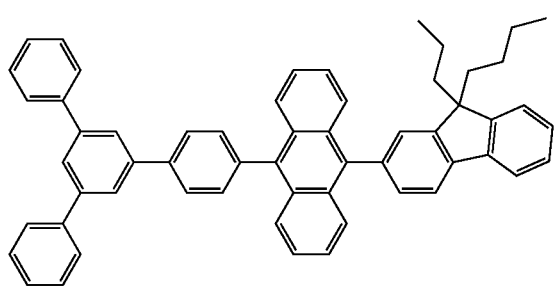
19
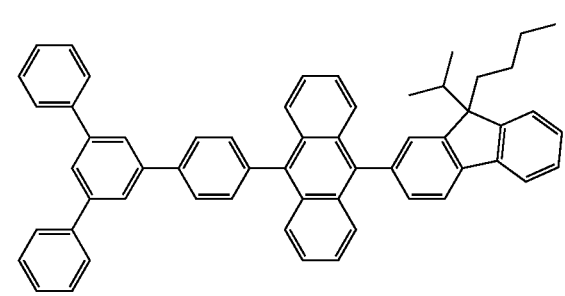
20
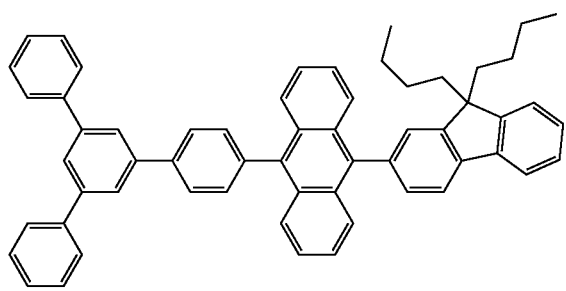
21
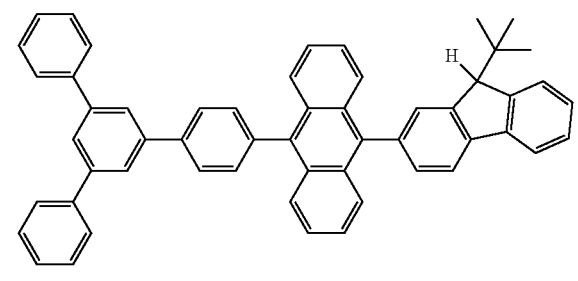
22

-continued
23
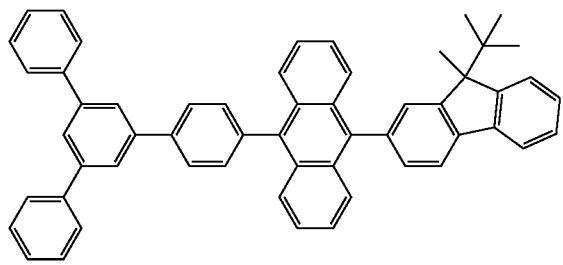
24
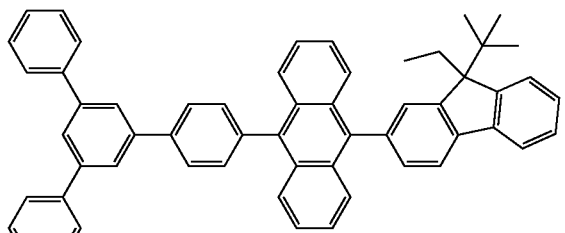
25
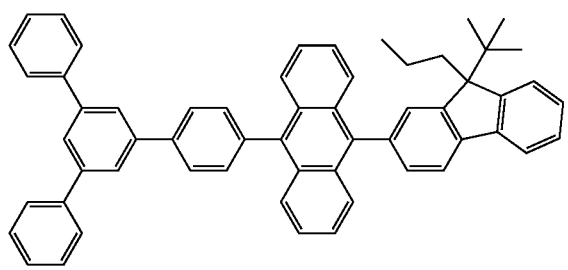
26
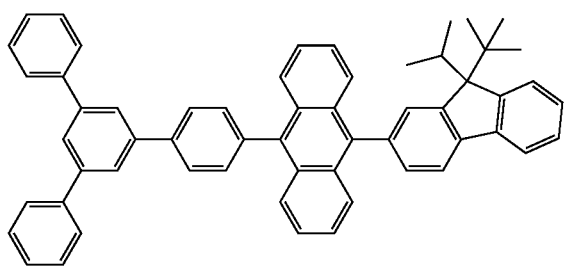
27
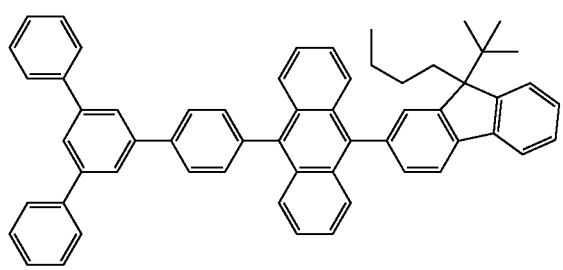
28
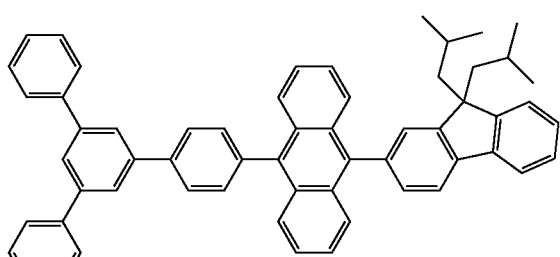
29
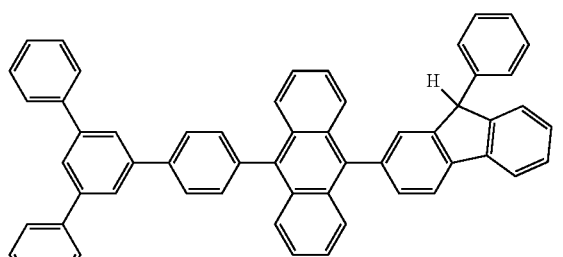
30
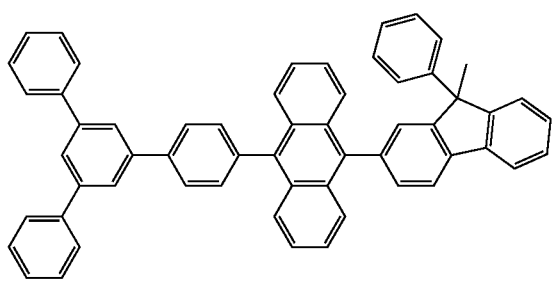
31
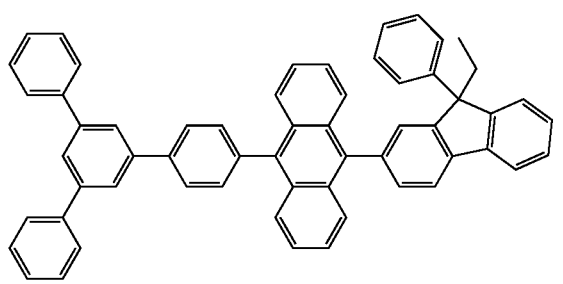
32
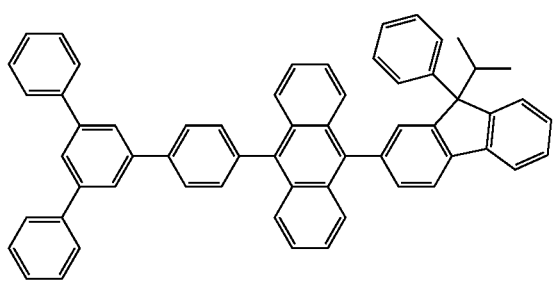

33
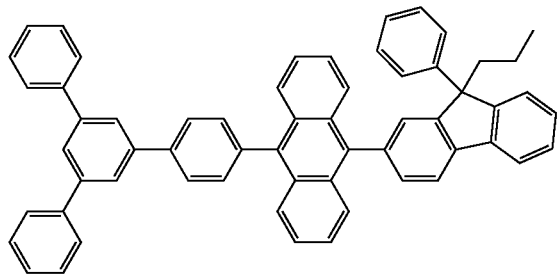
34
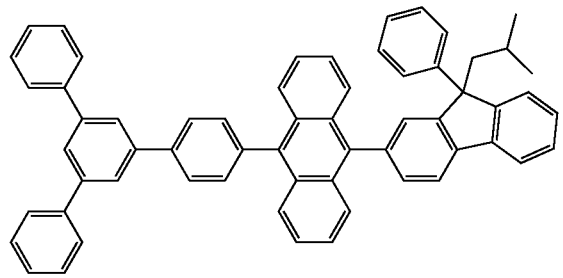
35
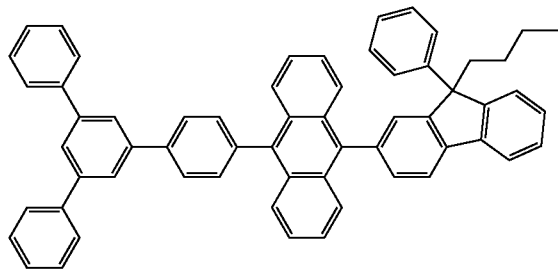
36
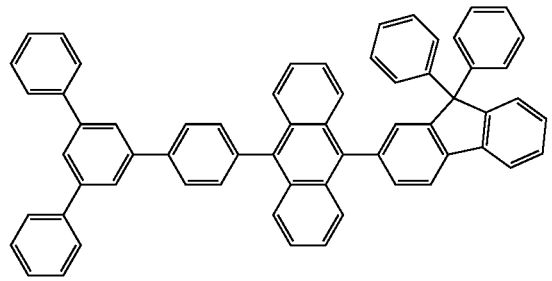
37
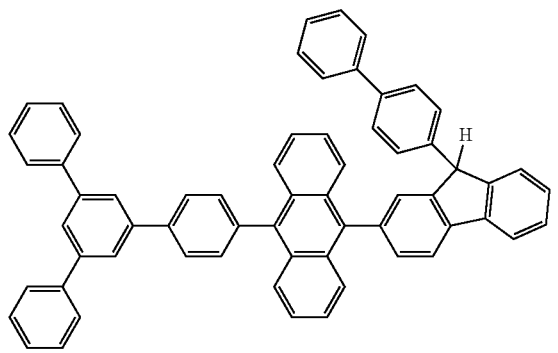
38
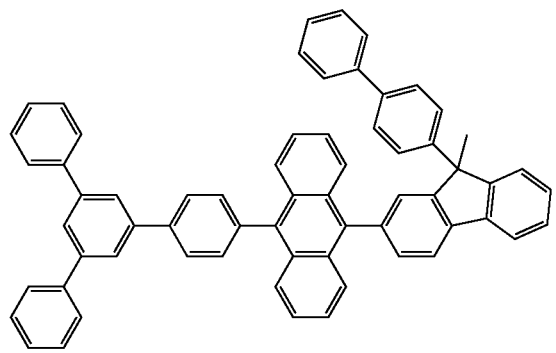
39
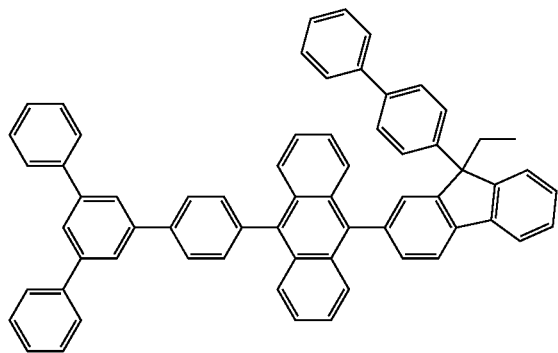
40
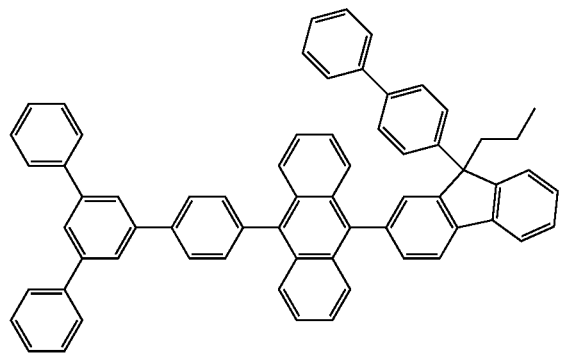
41
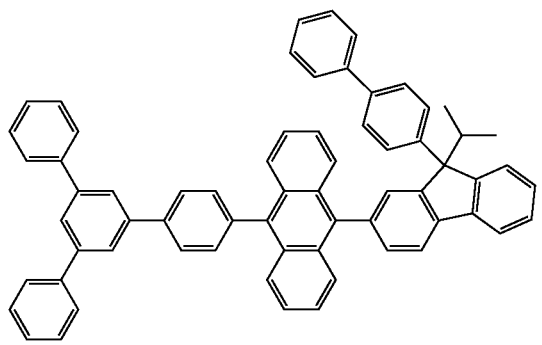
42
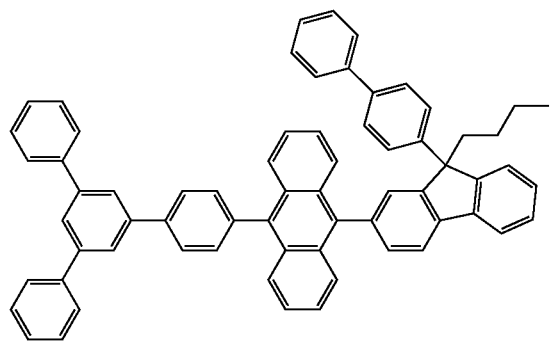

-continued
43
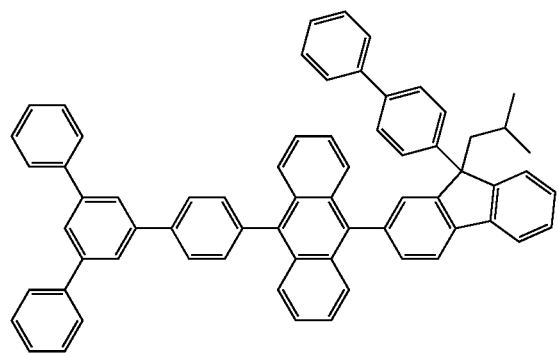
44
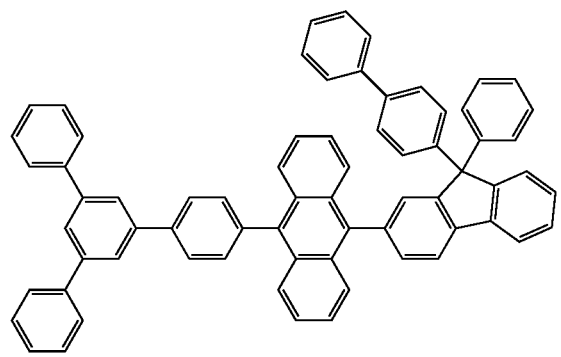
45
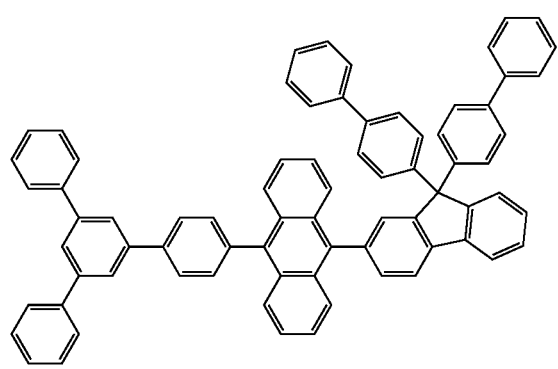
46
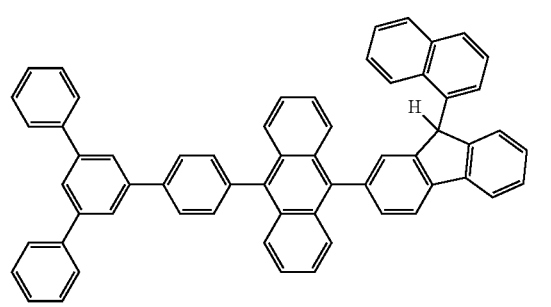
47
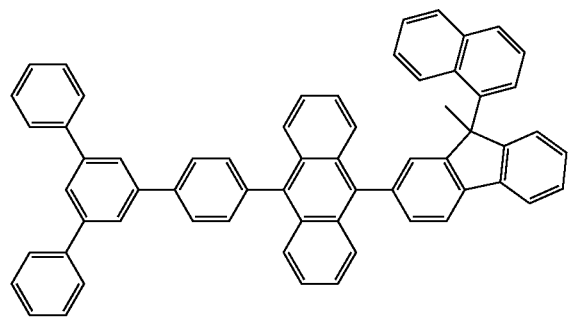
48
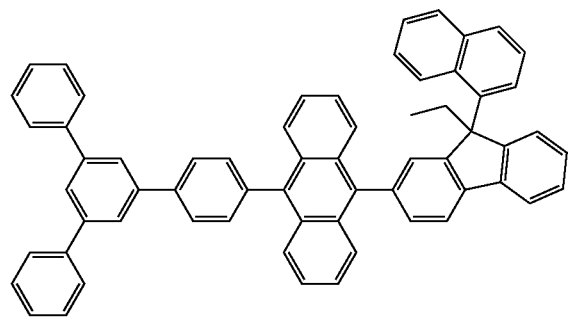
49
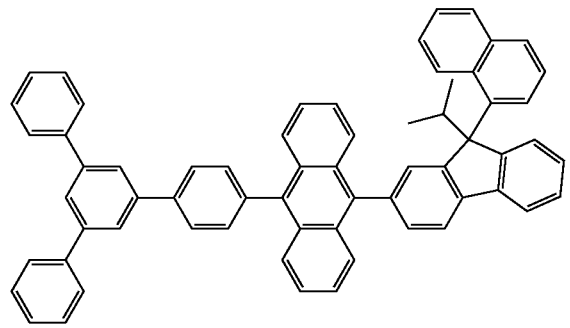
50
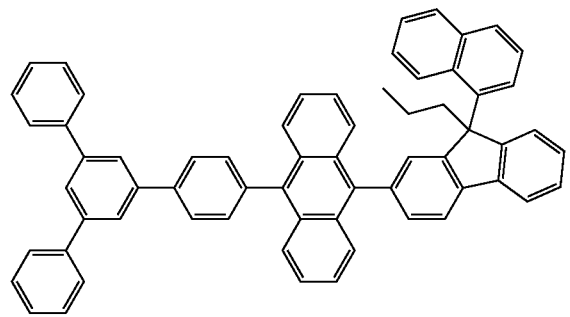

-continued
51
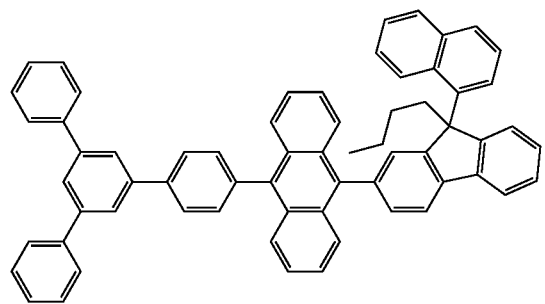
52
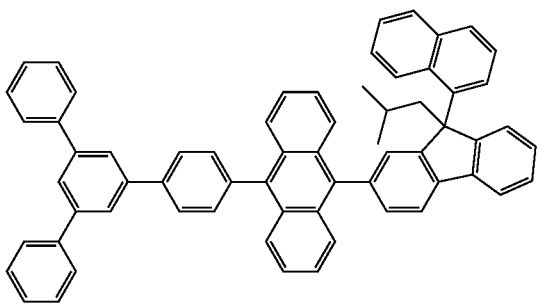
53
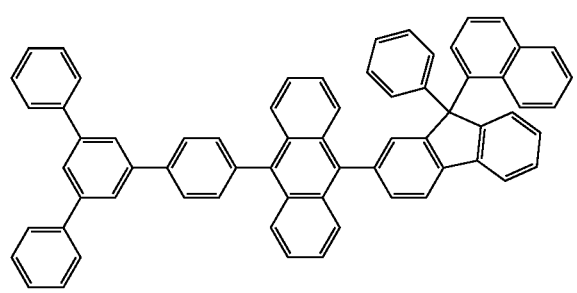
54
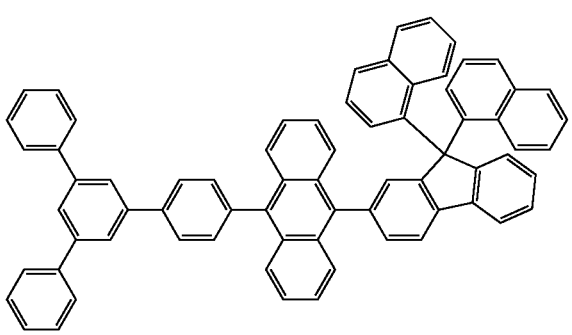
55
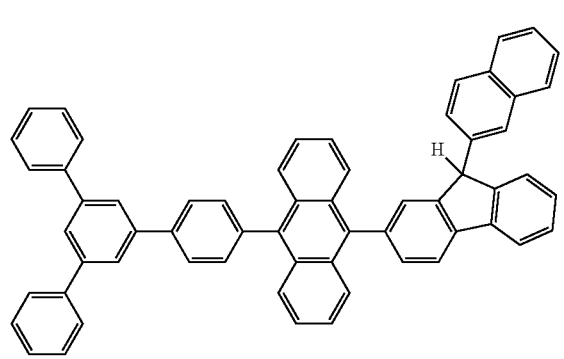
56
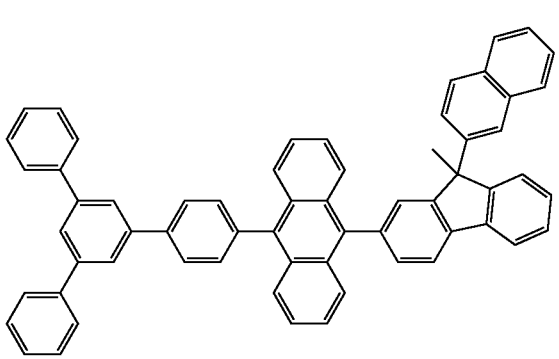
57
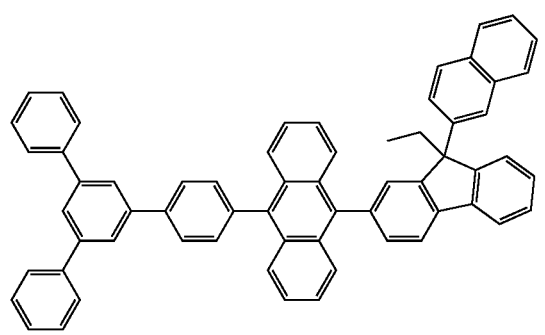
58
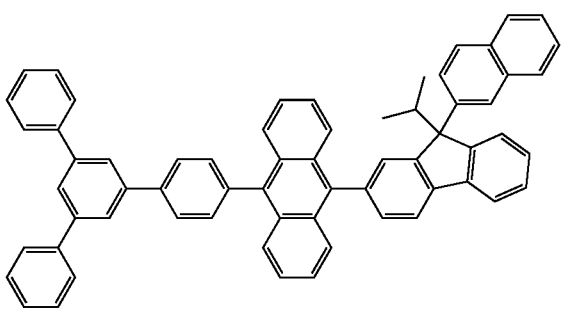

-continued
59
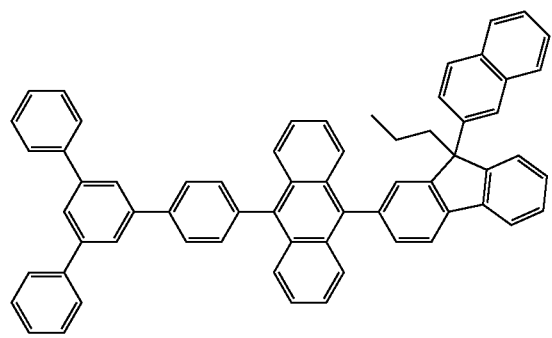
60
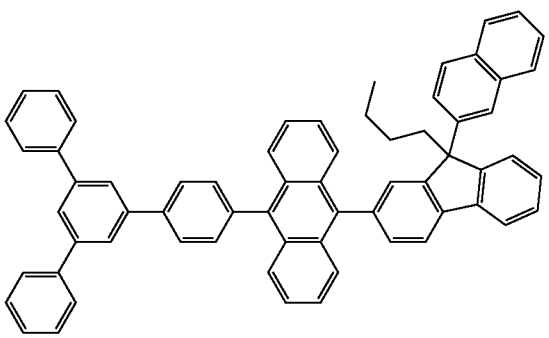
61
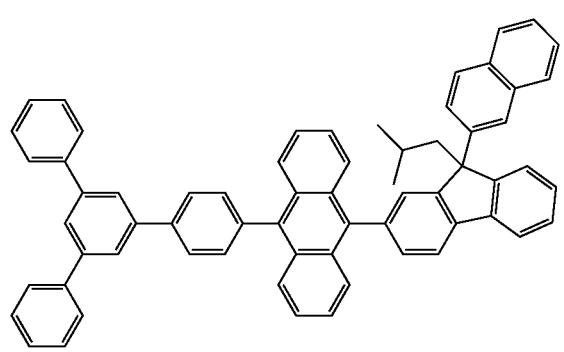
62
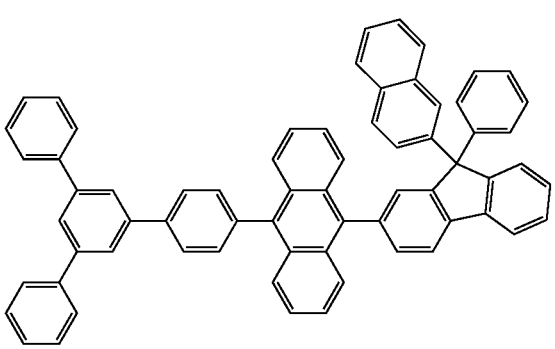
63
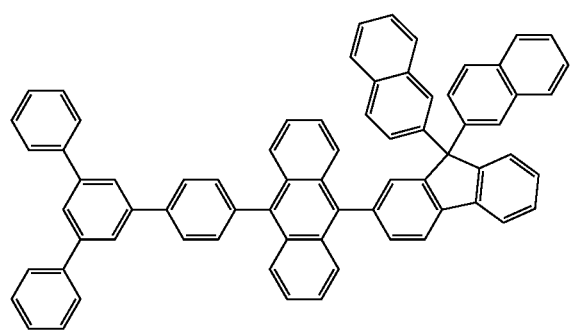
64
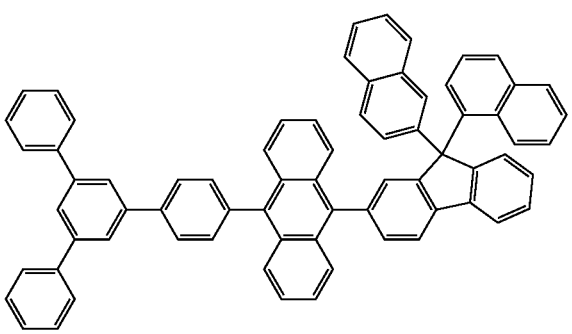
65
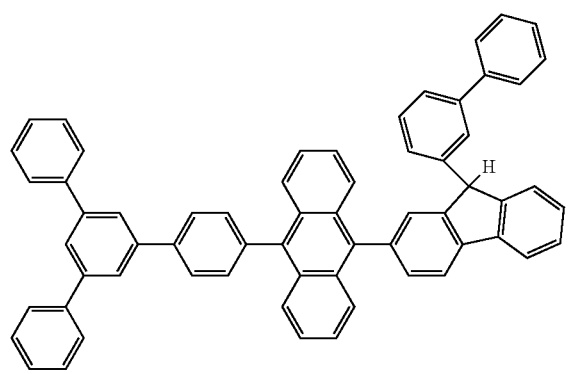
66
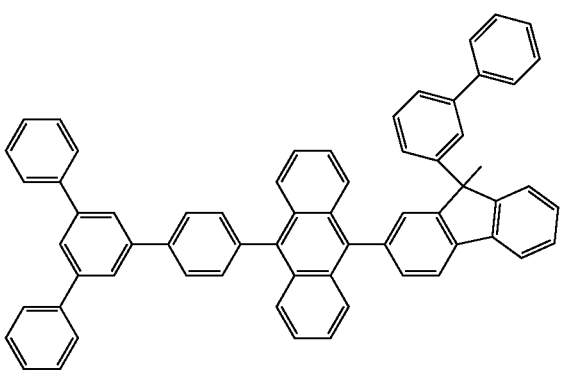

67
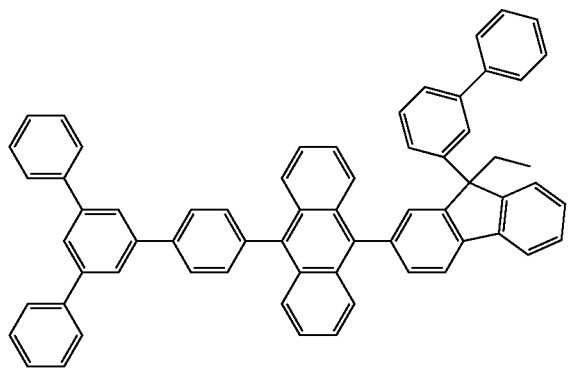
68
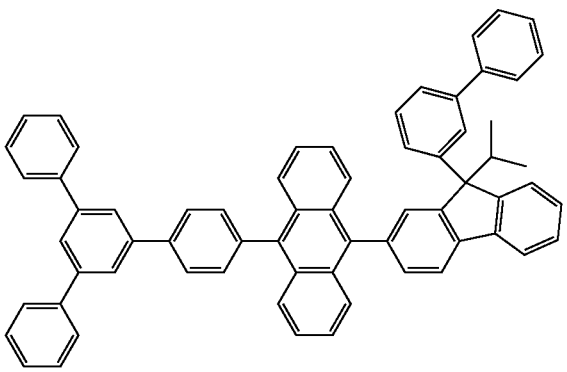
69
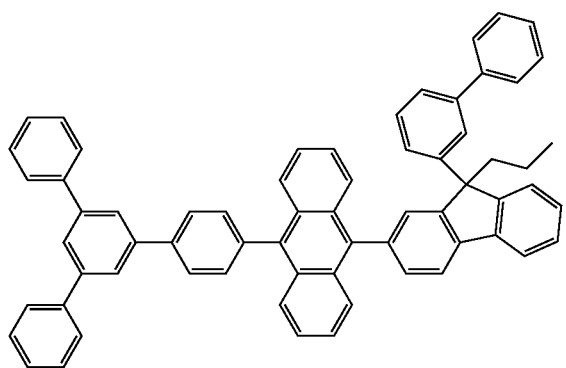
70
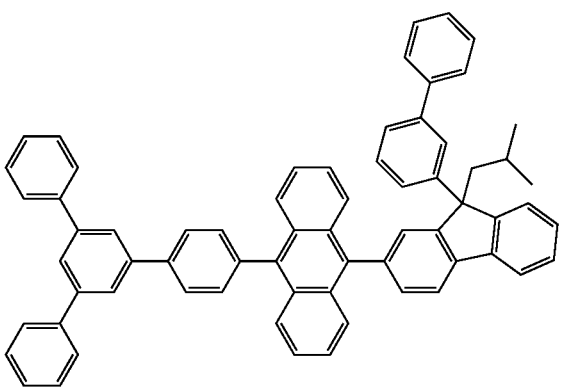
71
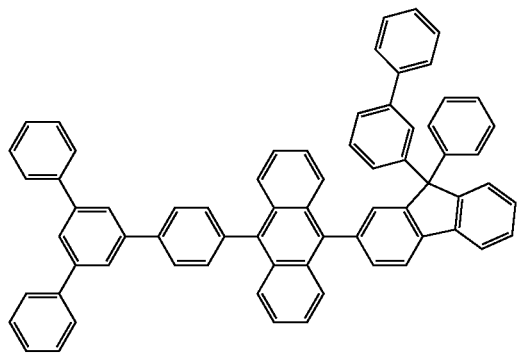
72
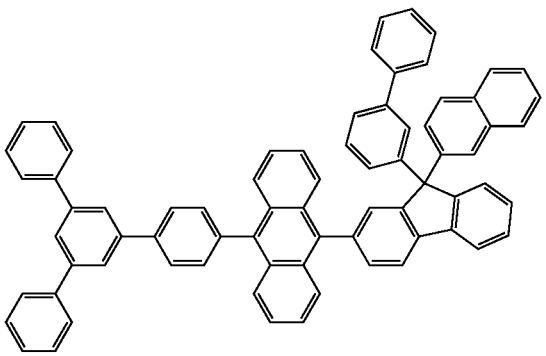
73
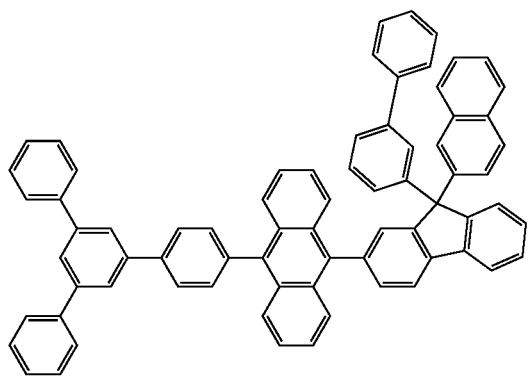
74
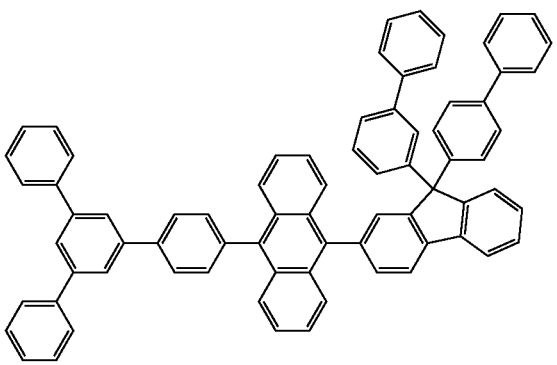

-continued
75
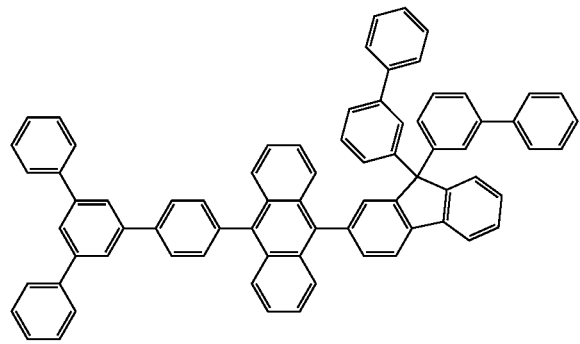
76
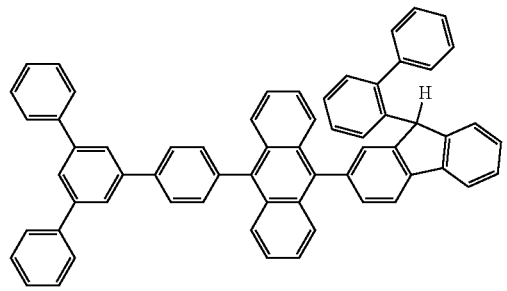
77
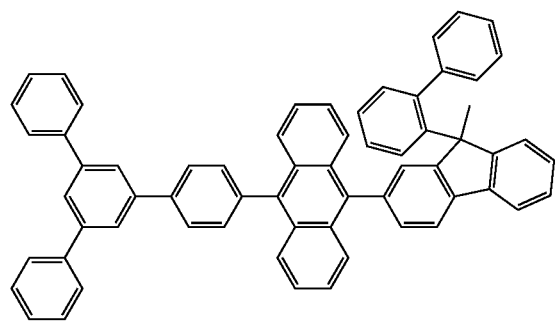
78
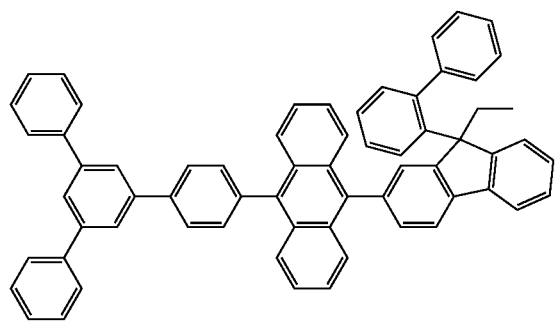
79
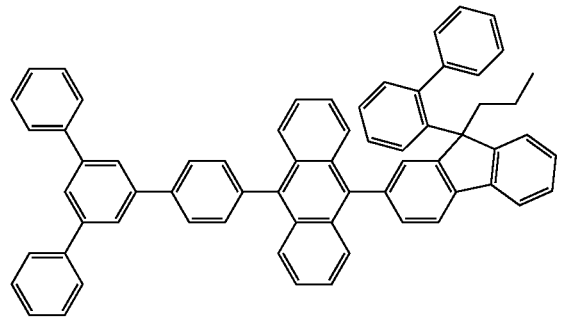
80
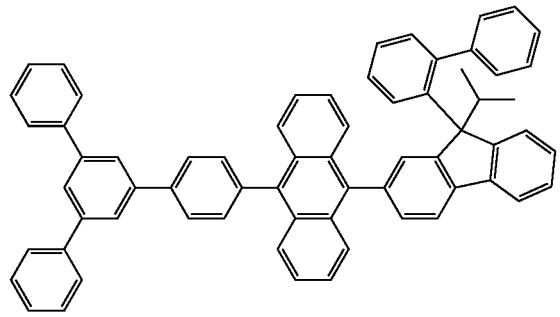
81
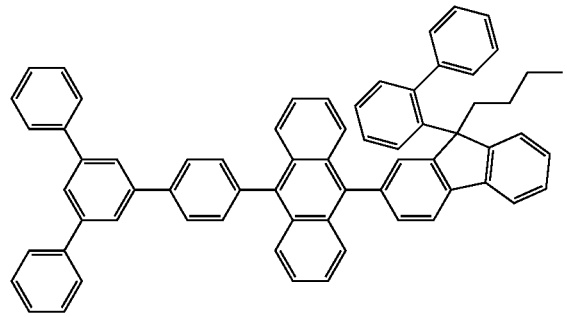
82
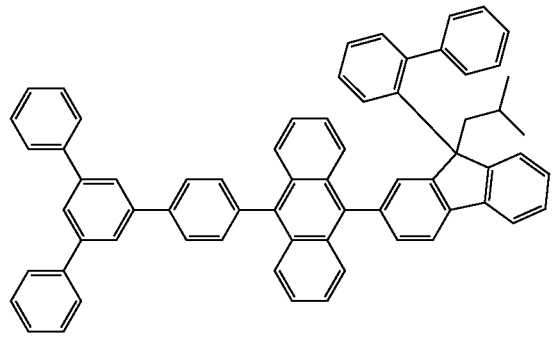

83
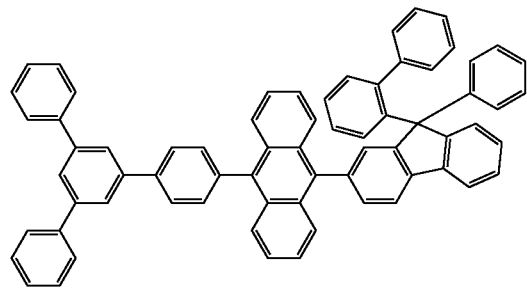
84
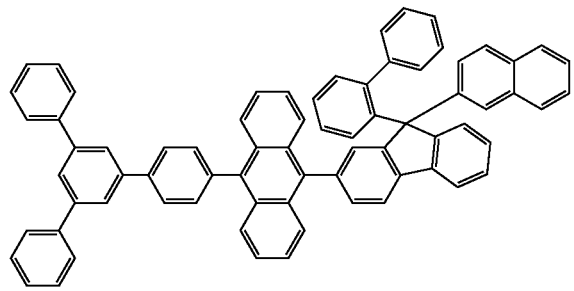
85
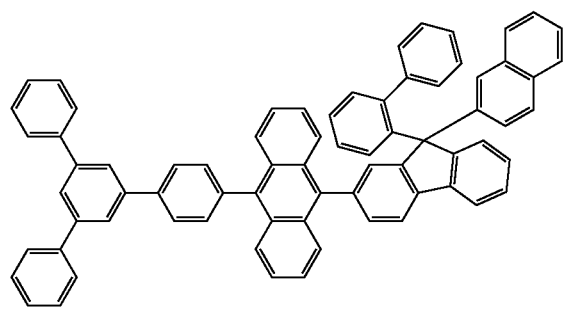
86
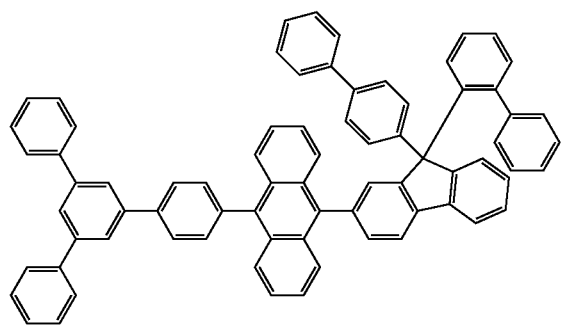
87
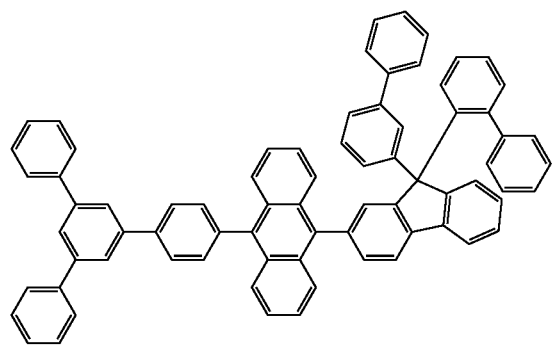
88
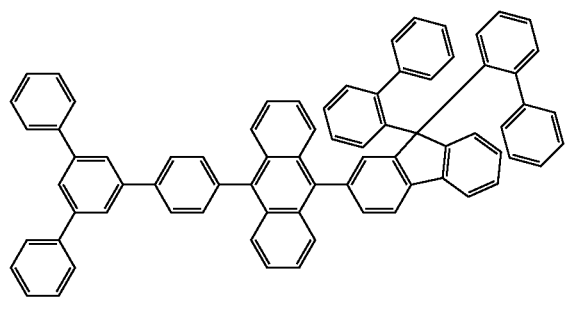
89
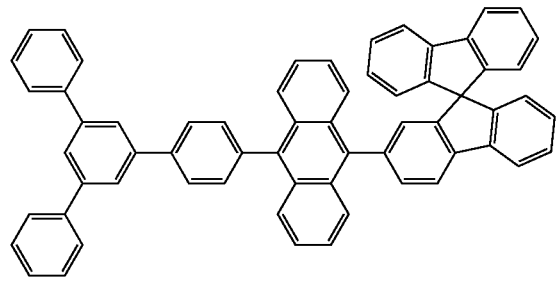
90
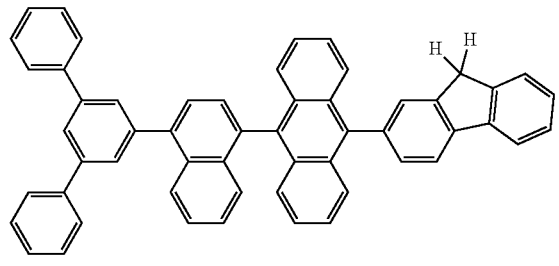
91
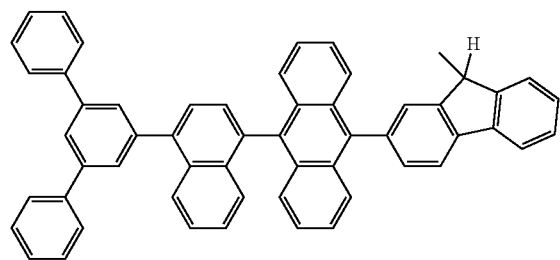
92
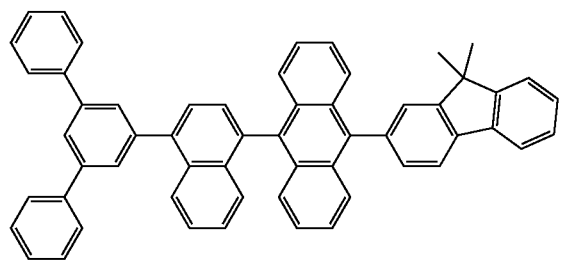

-continued
93
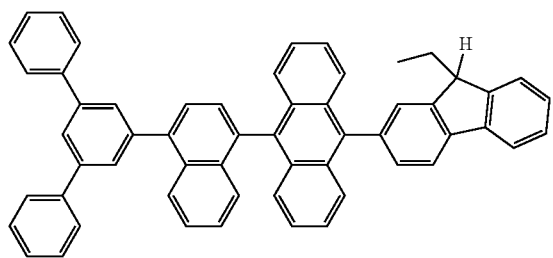
94
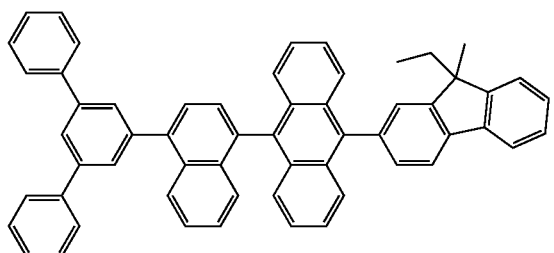
95
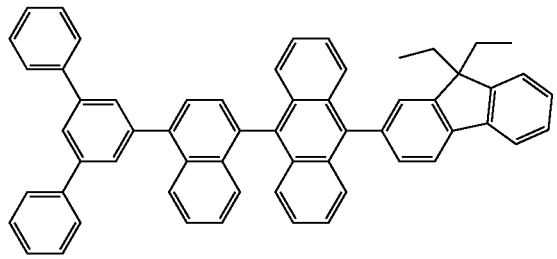
96
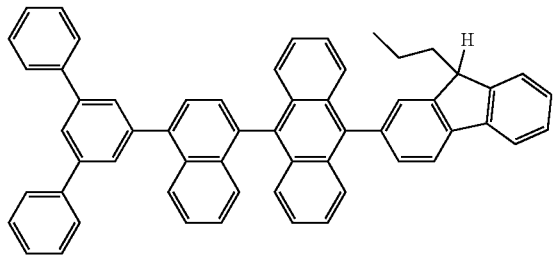
97
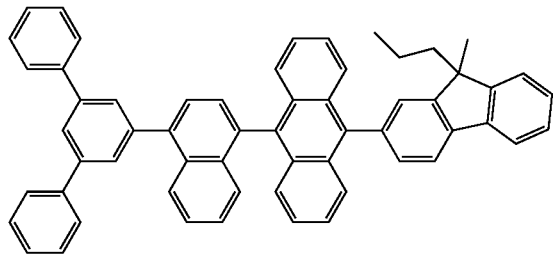
98
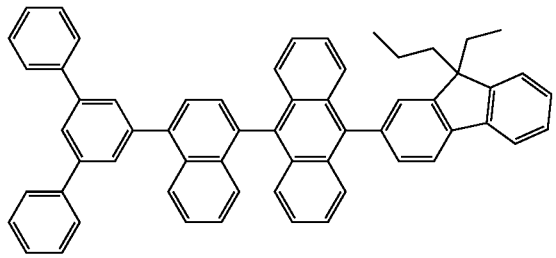
99
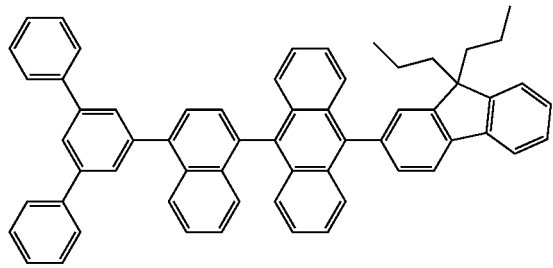
100
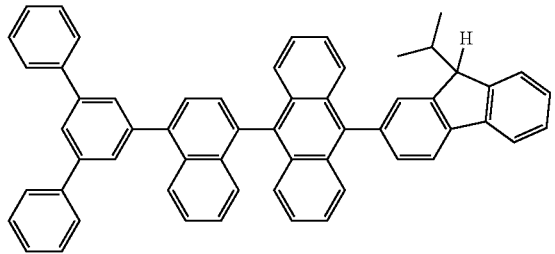
101
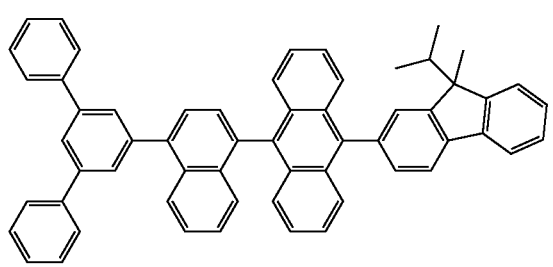
102
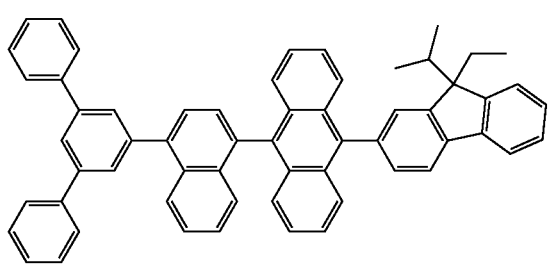
103
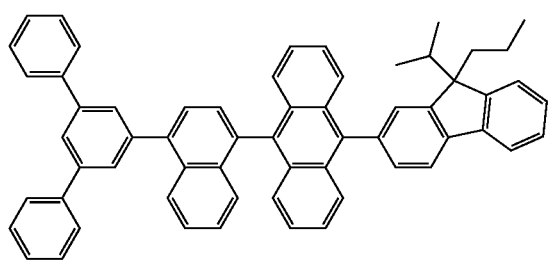
104
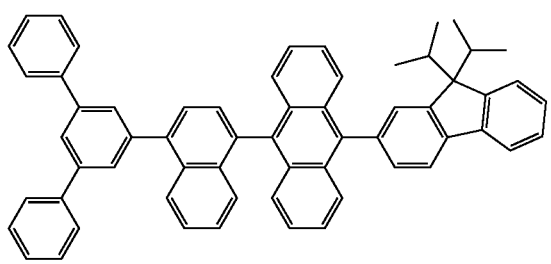

-continued
105
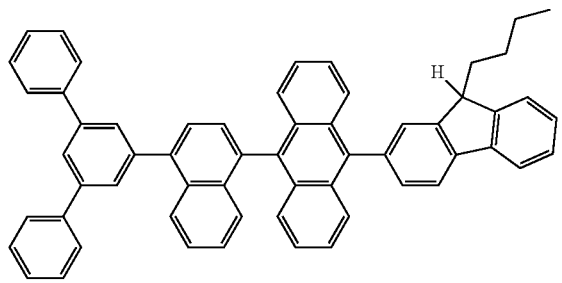
106
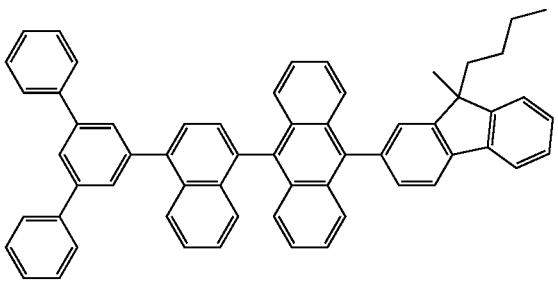
107
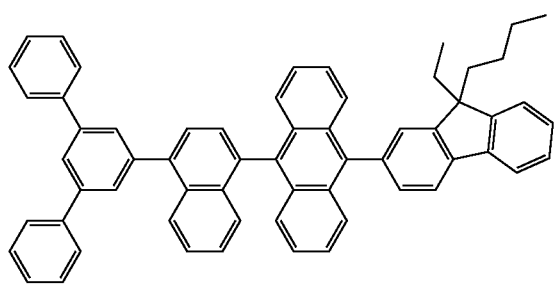
108
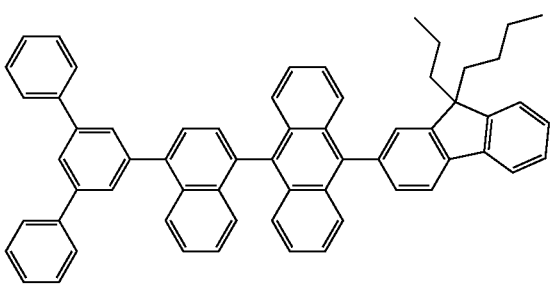
109
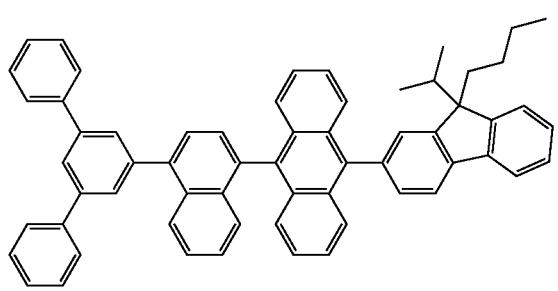
110
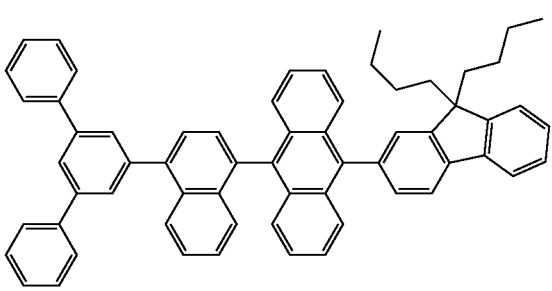
111
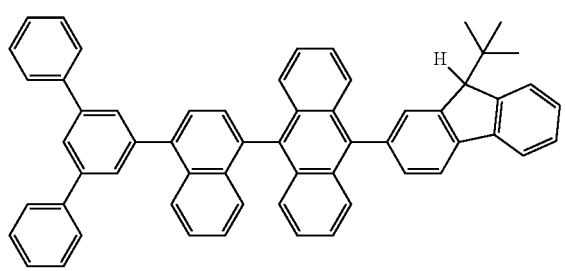
112
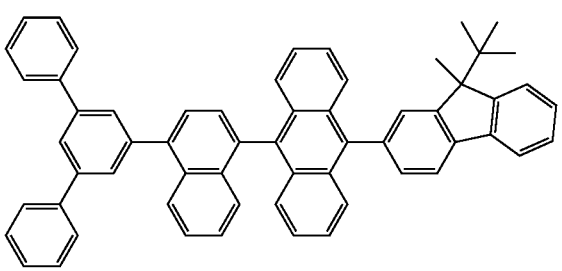
113
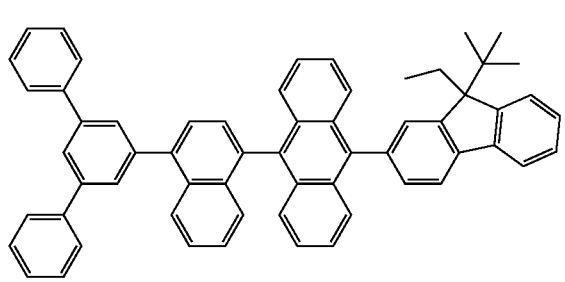
114
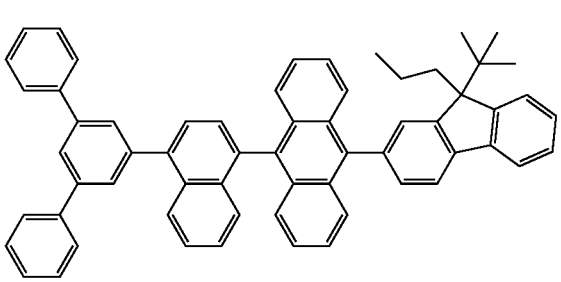

-continued
115
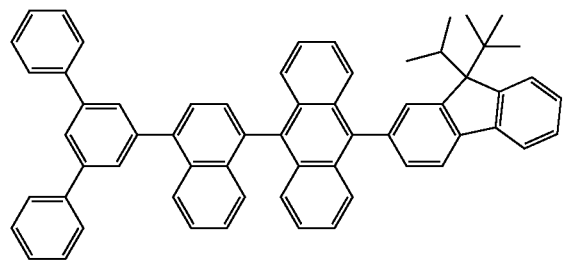
116
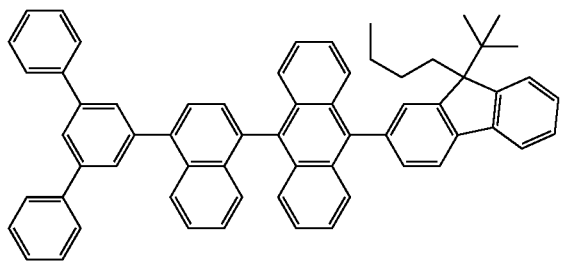
117
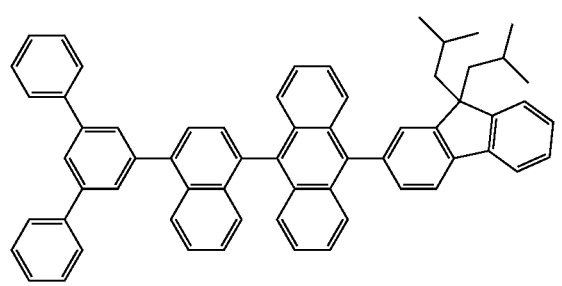
118
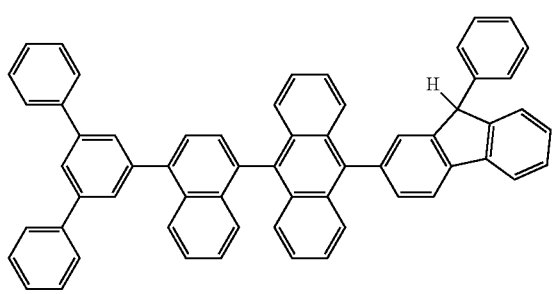
119
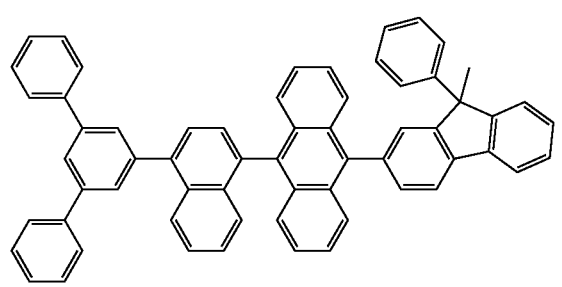
120
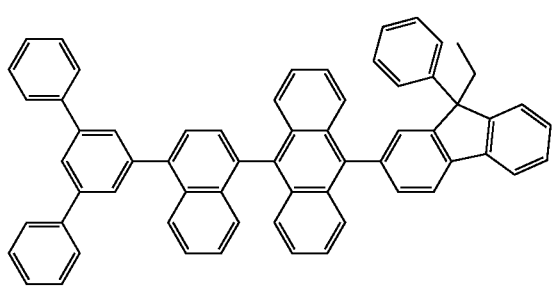
121
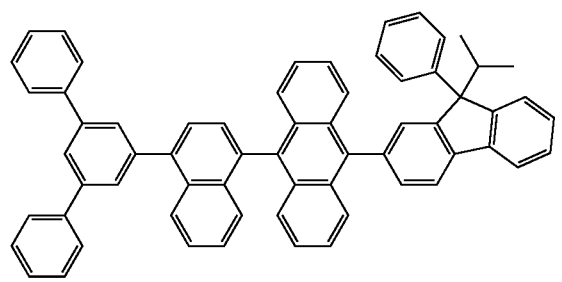
122
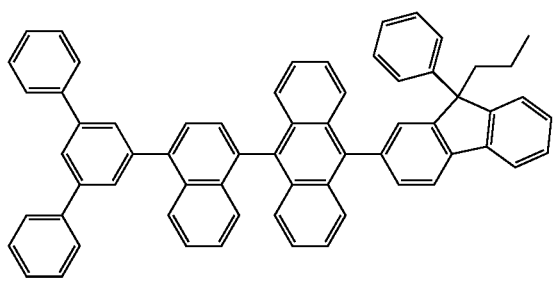
123
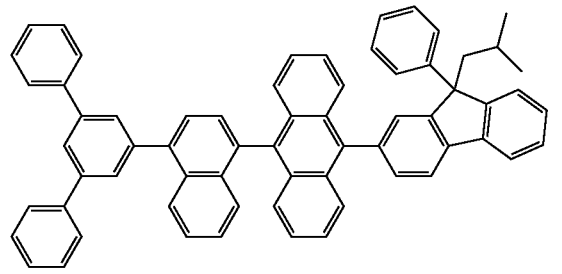
124
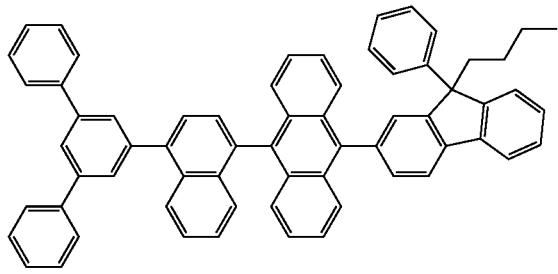

-continued
125
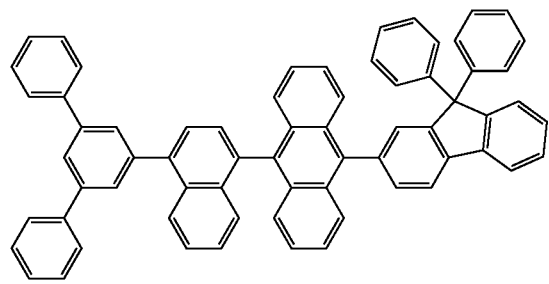
126
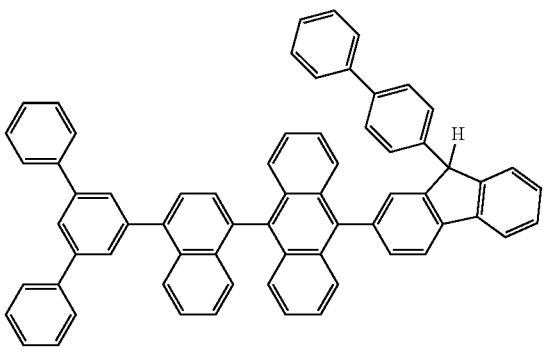
127
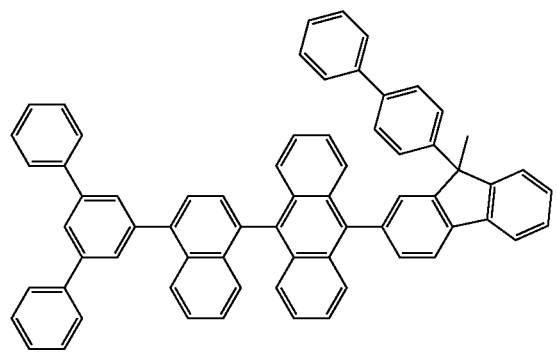
128
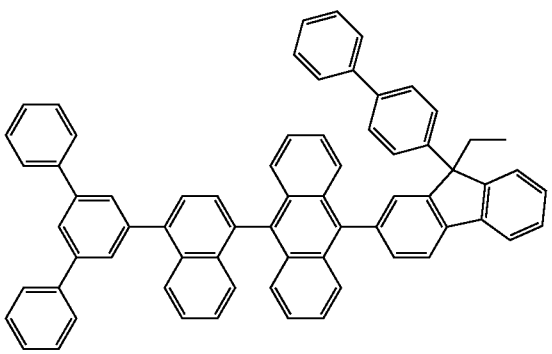
129
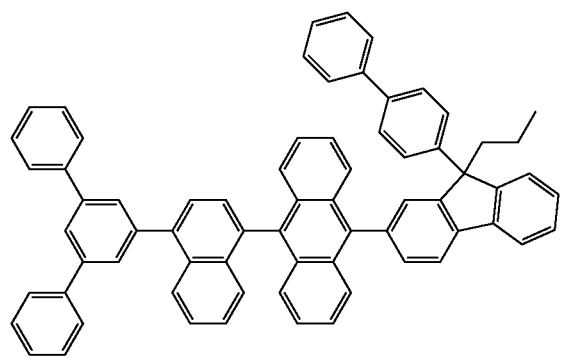
130
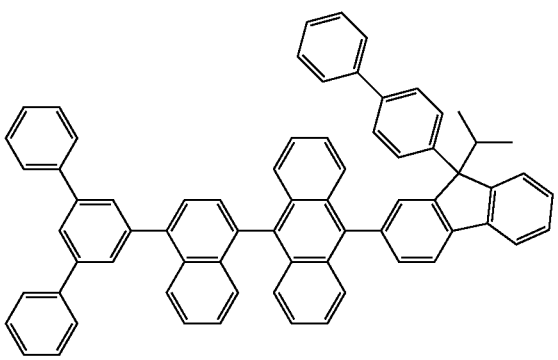
131
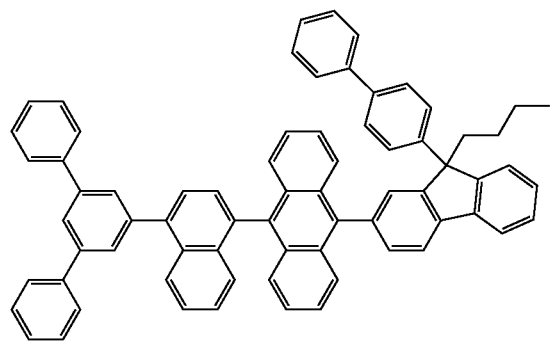
132
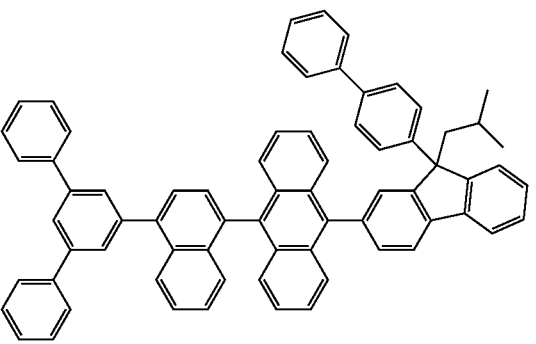

-continued
133
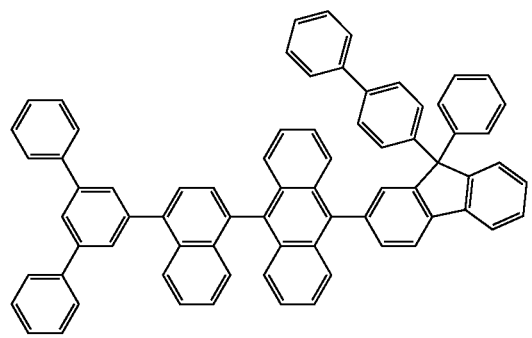
134
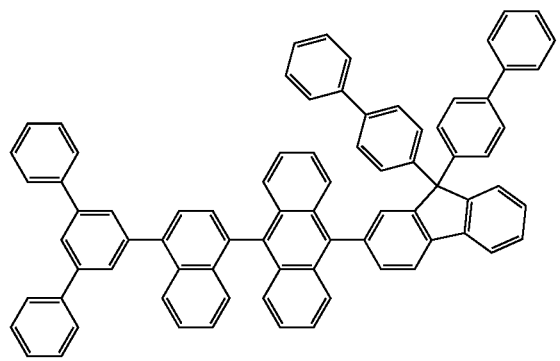
135
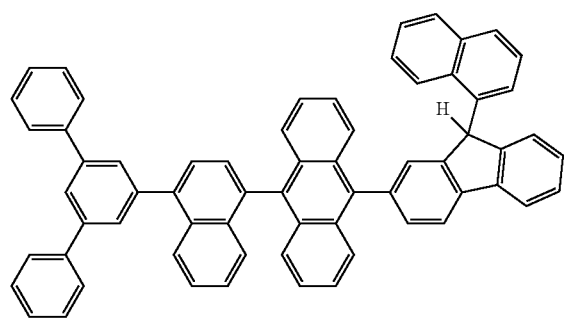
136
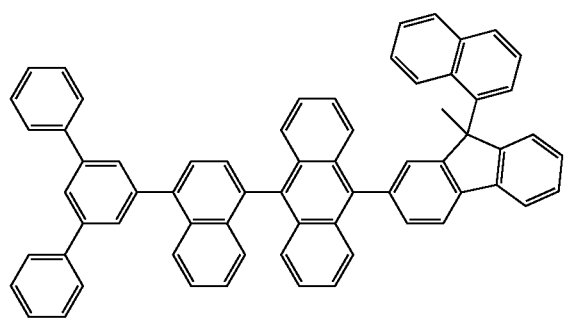
137
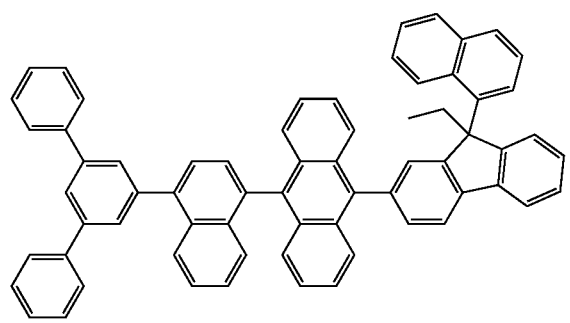
138
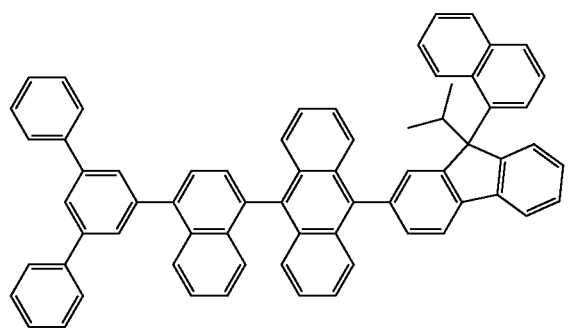
139
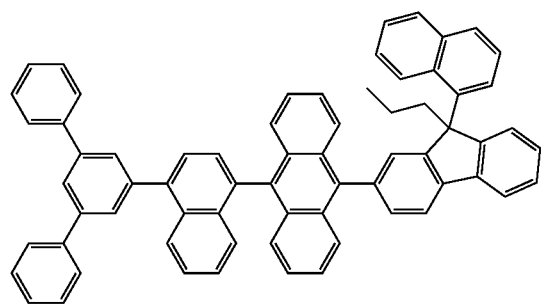
140
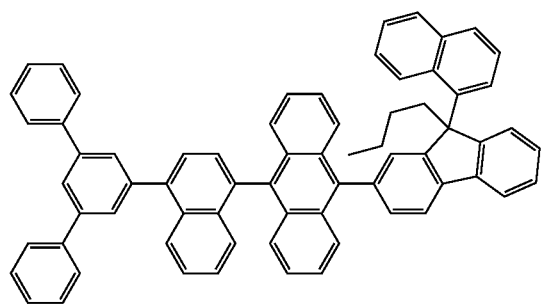

-continued
141
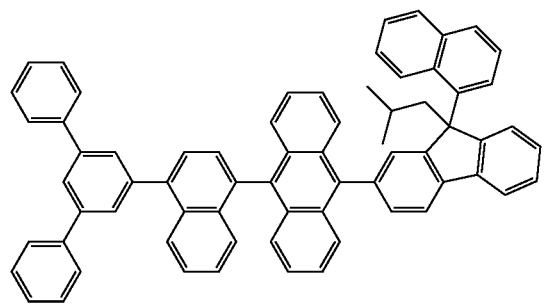
142
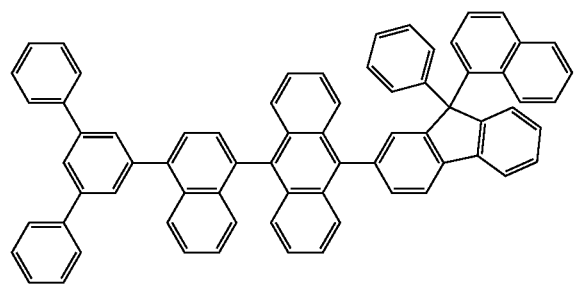
143
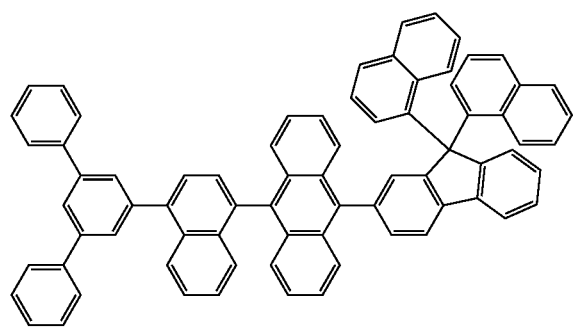
144
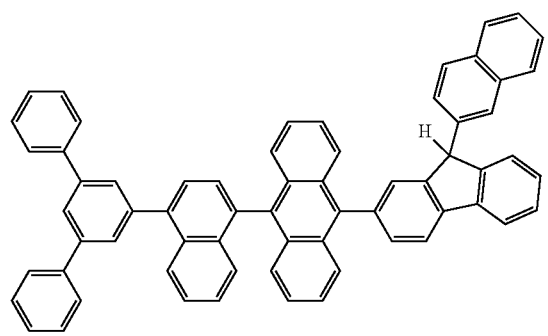
145
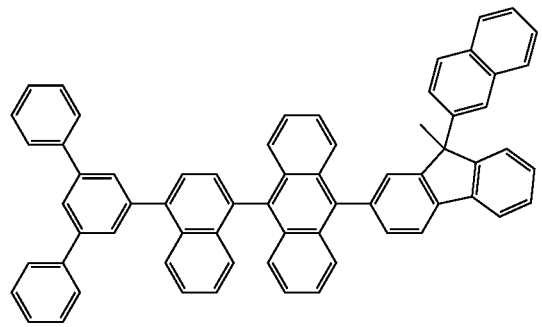
146
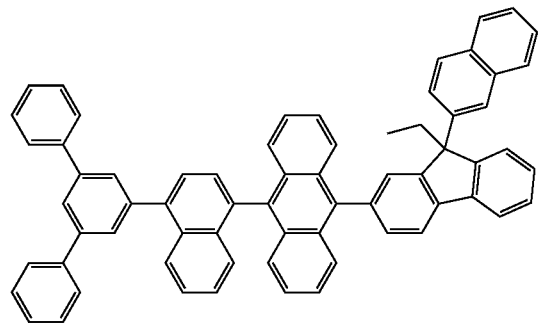
147
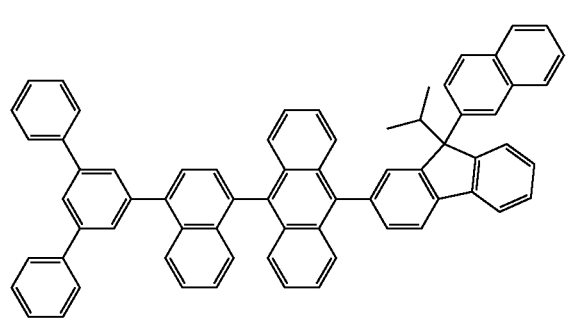
148
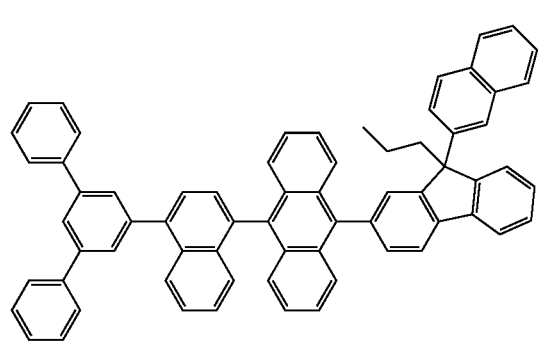

-continued
149
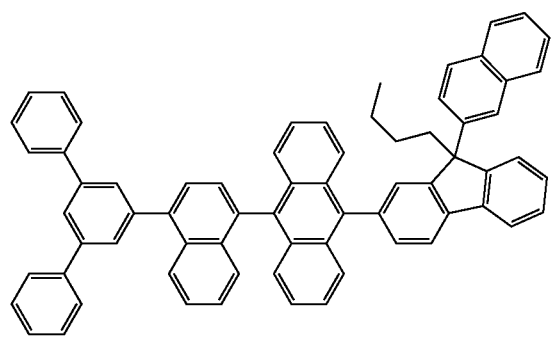
150
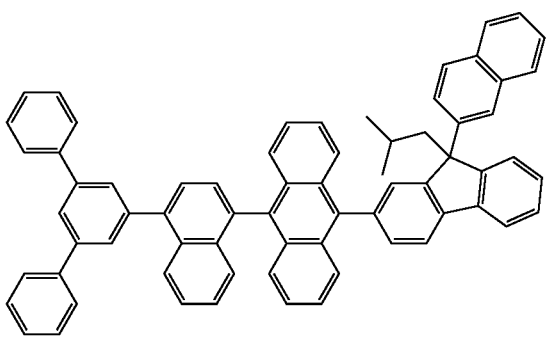
151
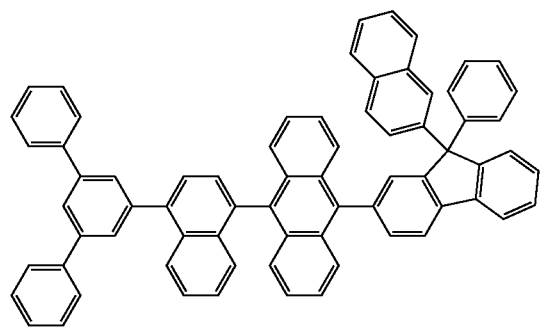
152
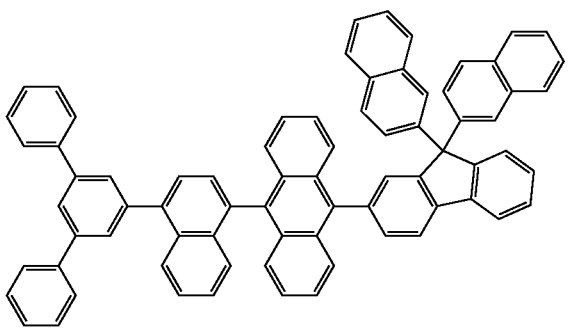
153
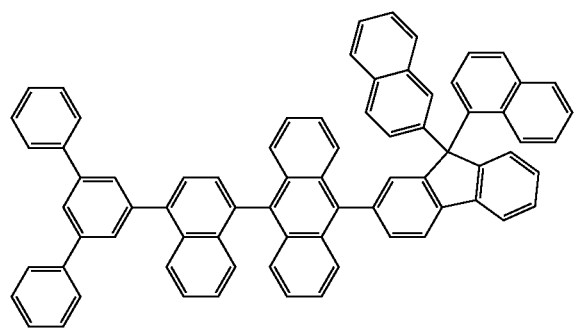
154
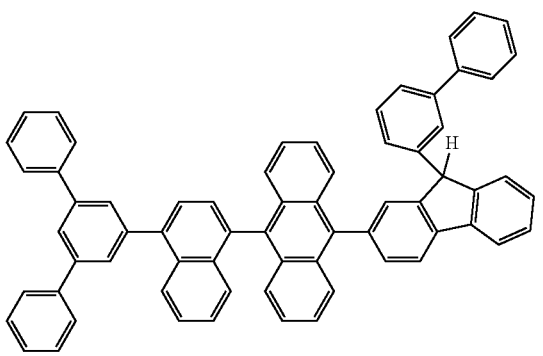
155
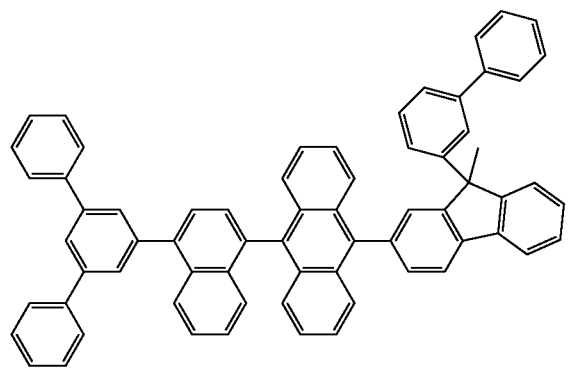
156
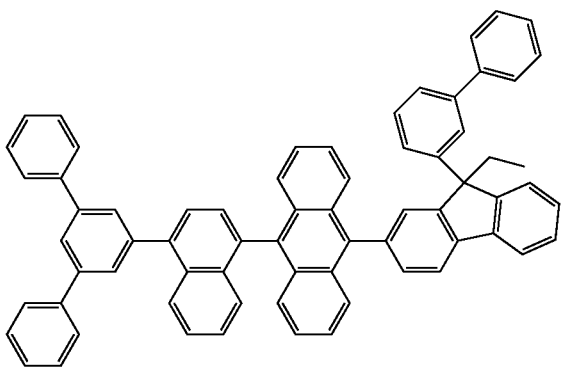

-continued
157
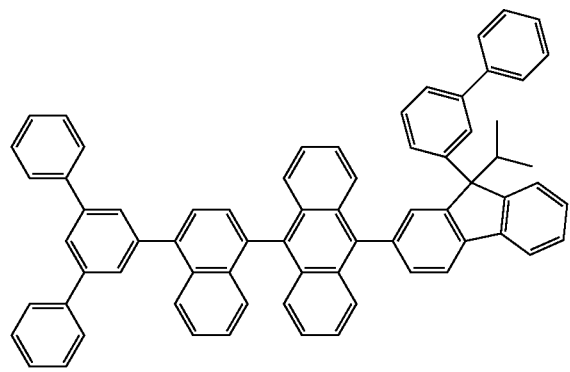
158
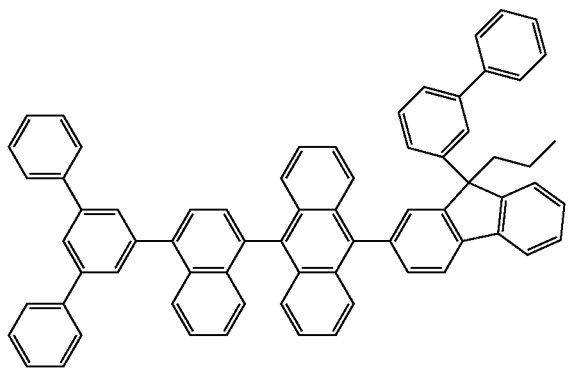
159
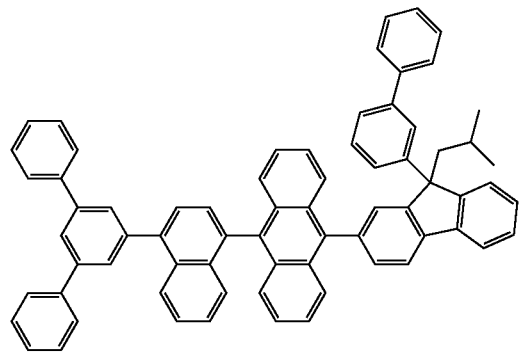
160
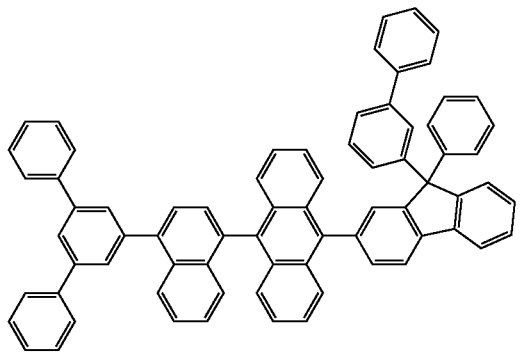
161
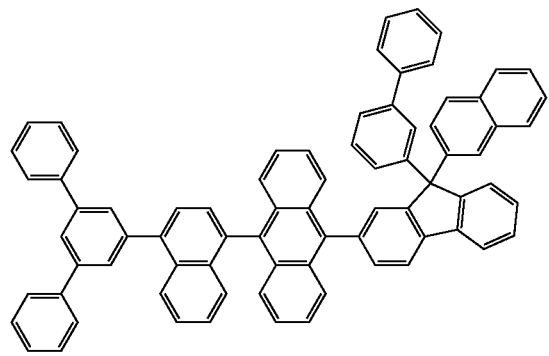
162
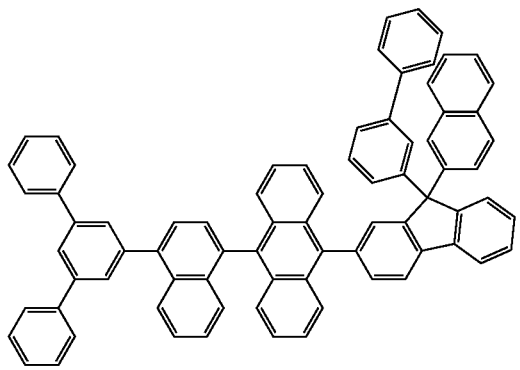
163
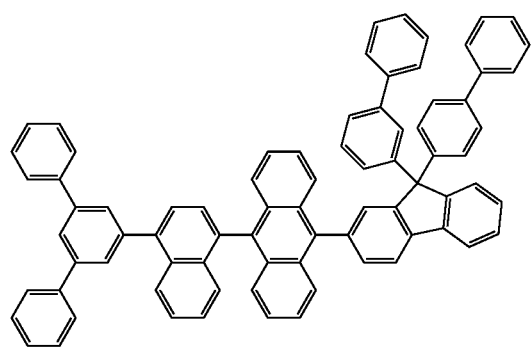
164
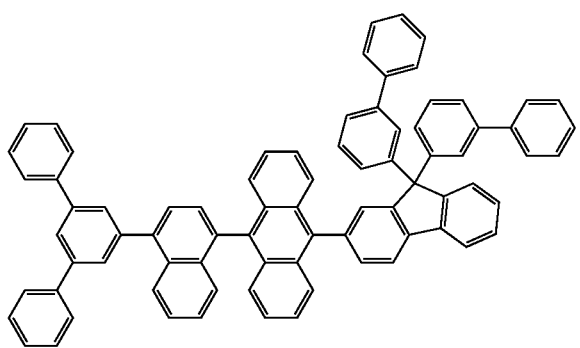

-continued
| 165 | 166 |
|---|---|
| 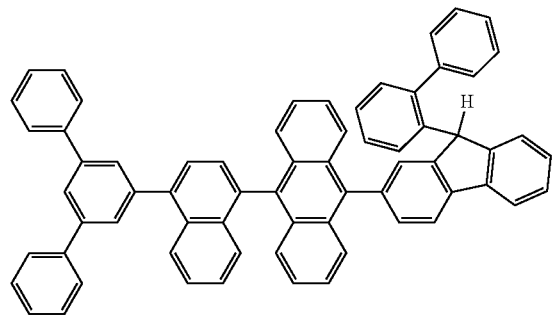 | 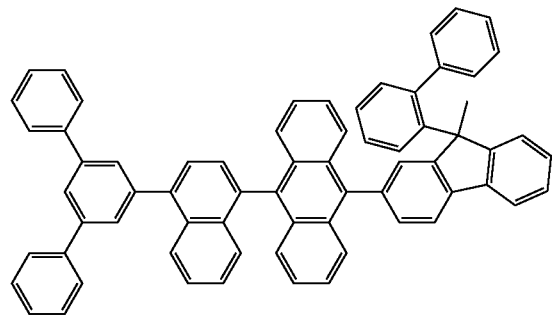 |
| 167 | 168 |
| 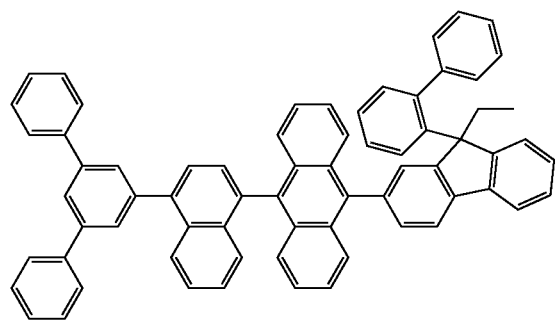 | 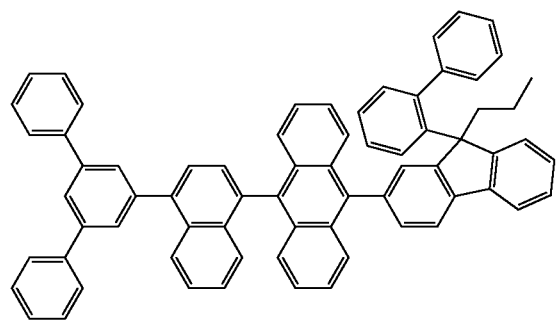 |
| 169 | 170 |
| 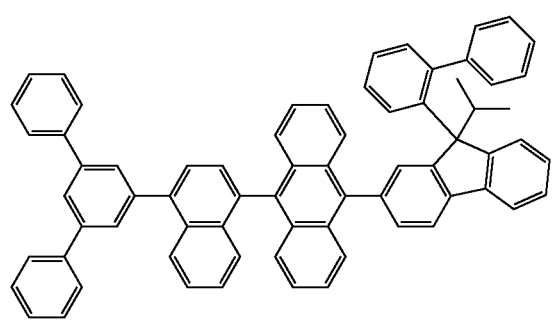 | 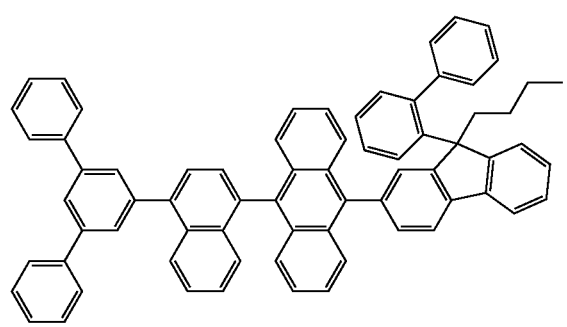 |
| 171 | 172 |
| 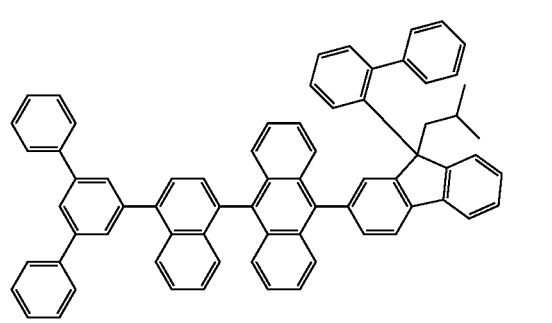 | 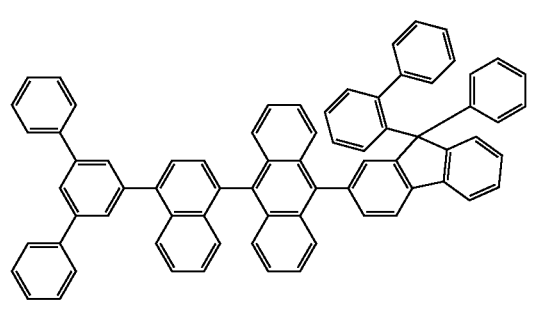 |
| 173 | 174 |
| 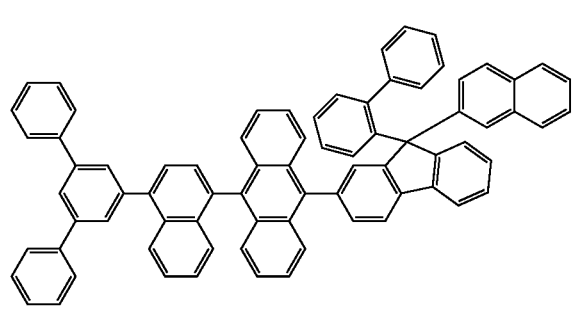 | 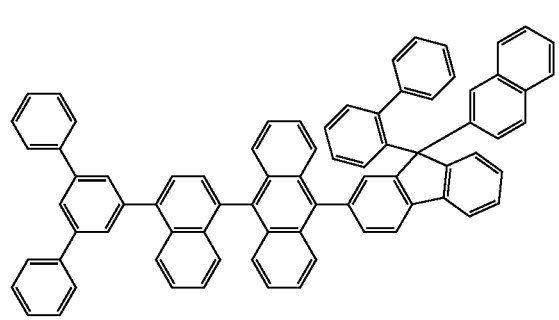 |

-continued
175
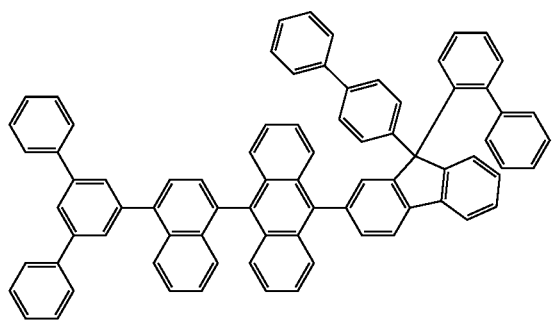
176
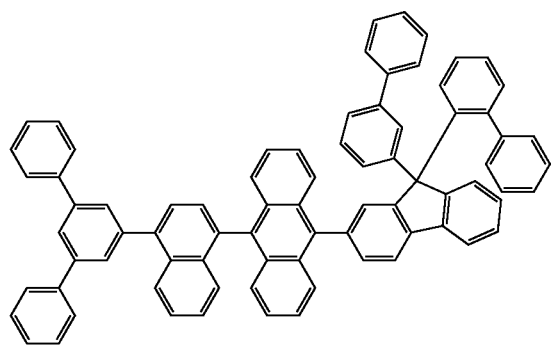
177
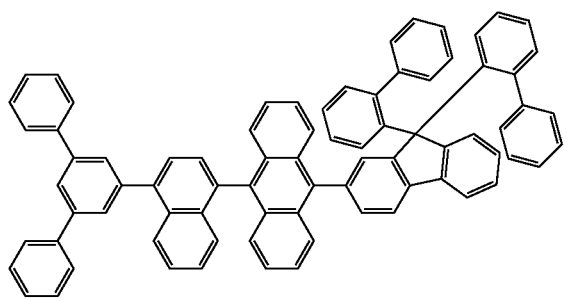
178
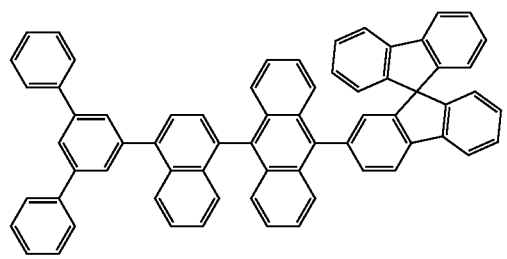
179
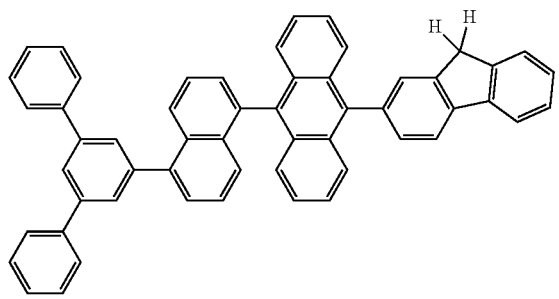
180
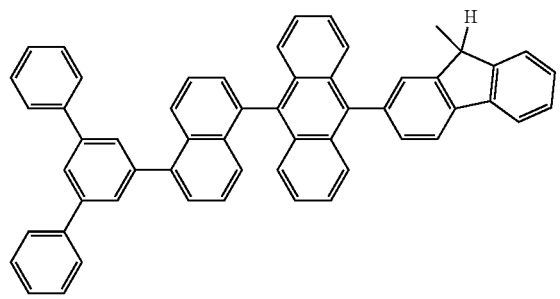
181
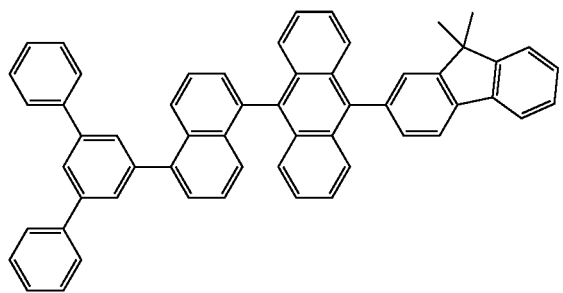
182
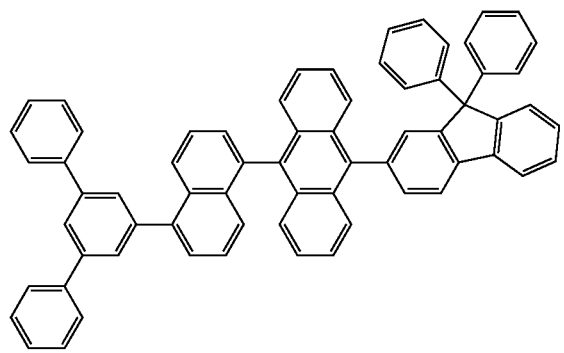

-continued
183
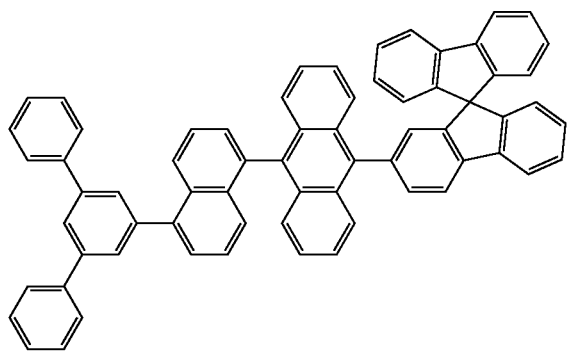
184
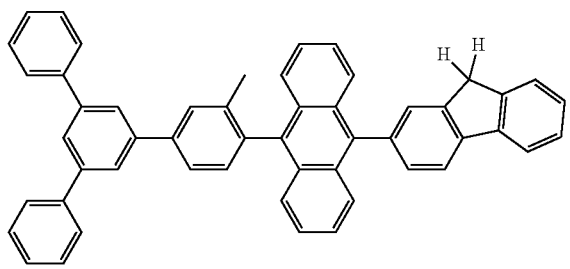
185
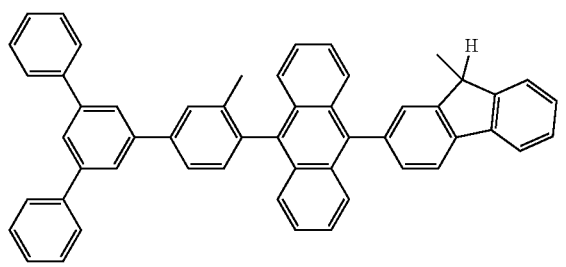
186
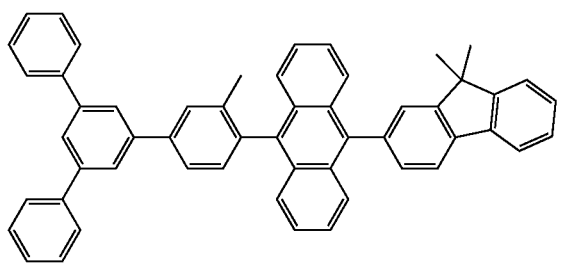
187
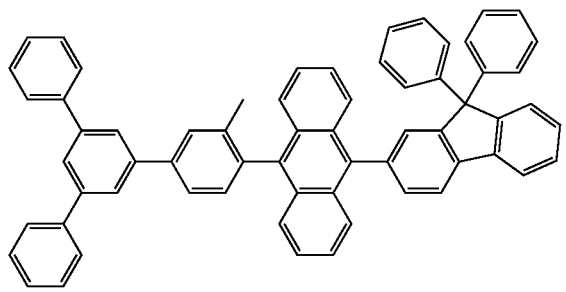
188
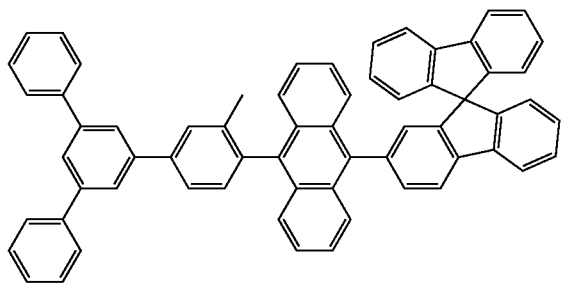
189
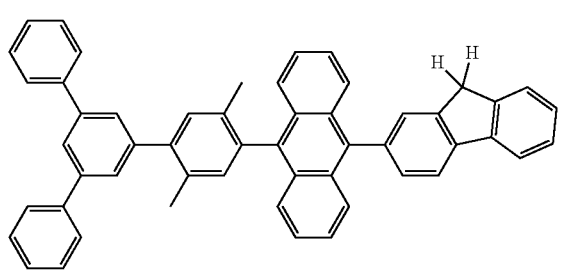
190
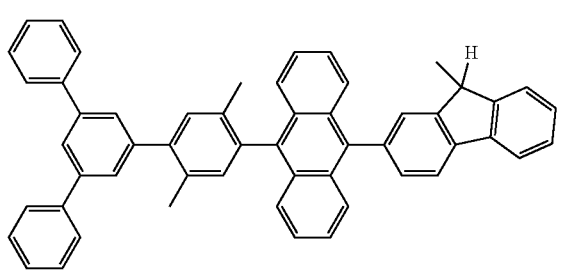
191
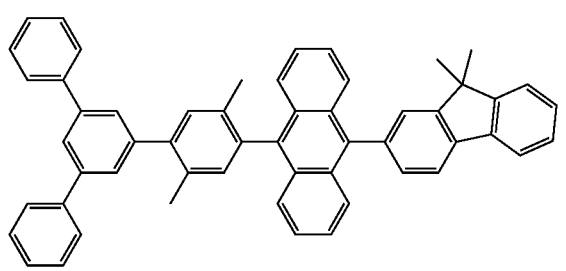
192
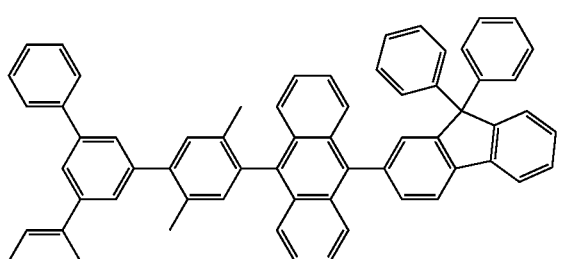

193 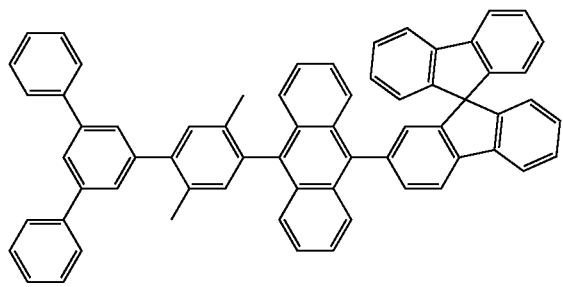
194 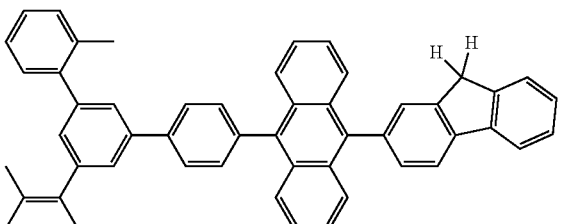
195 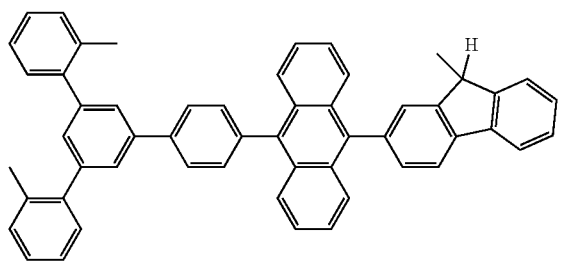
196 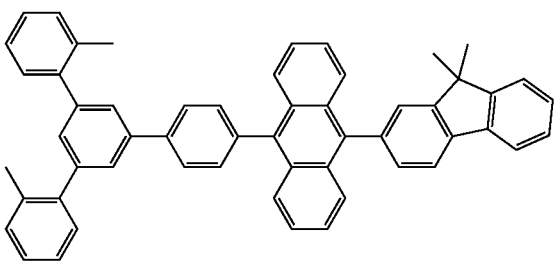
197 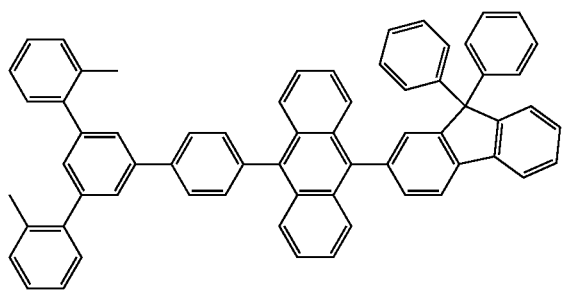
198 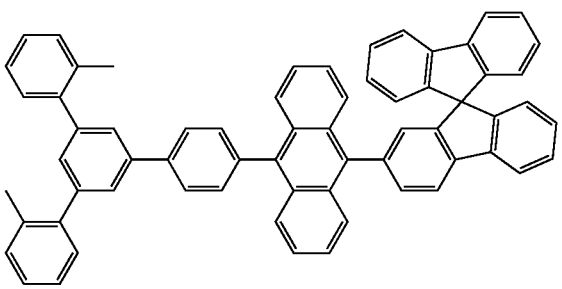
199 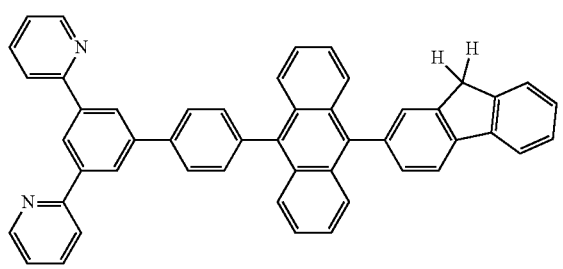
200 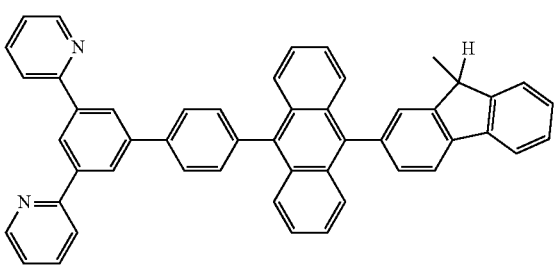
201 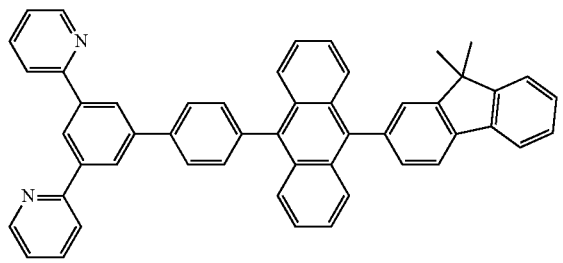
202 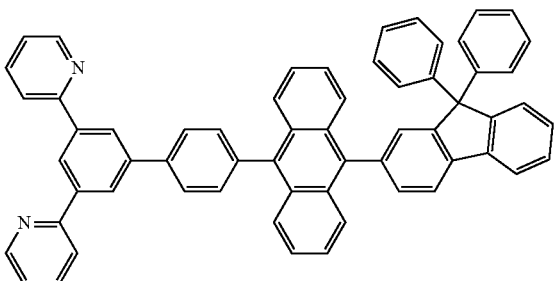

203
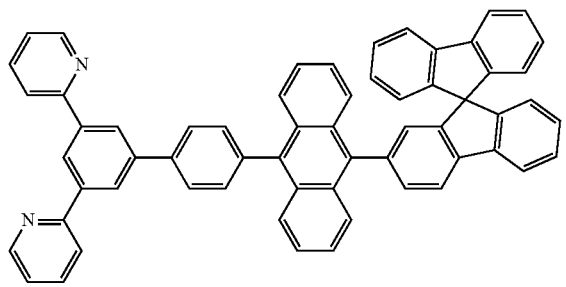
204
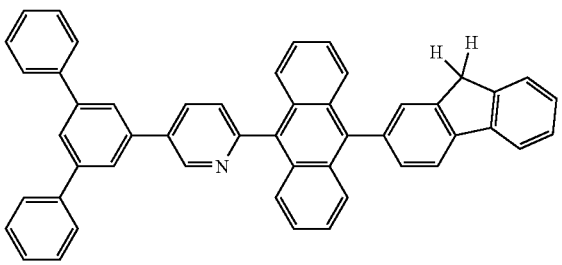
205
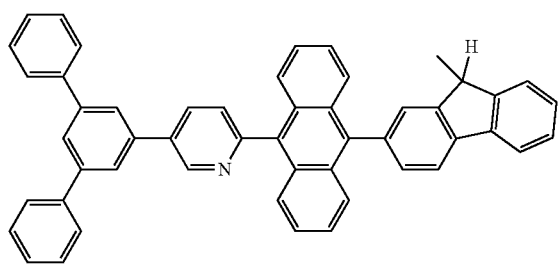
206
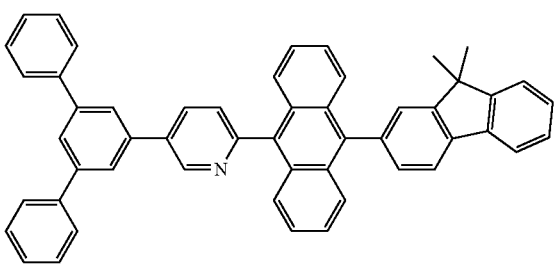
207
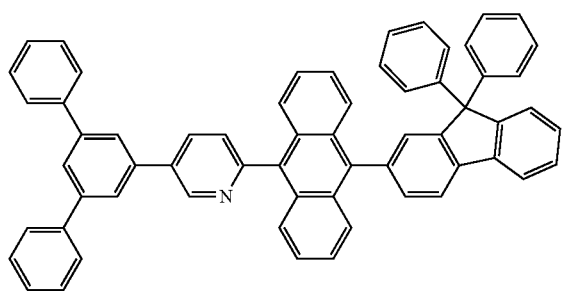
208
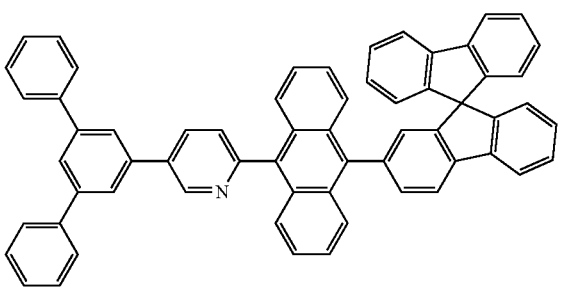
209
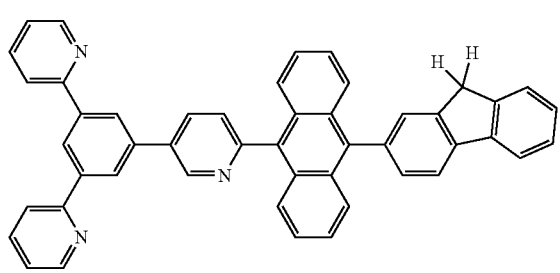
210
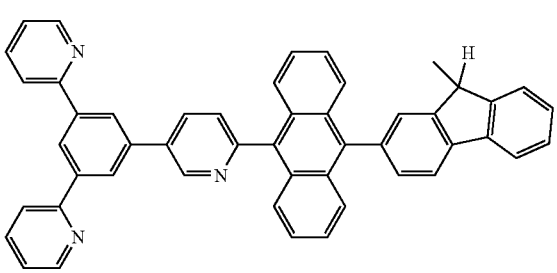
211
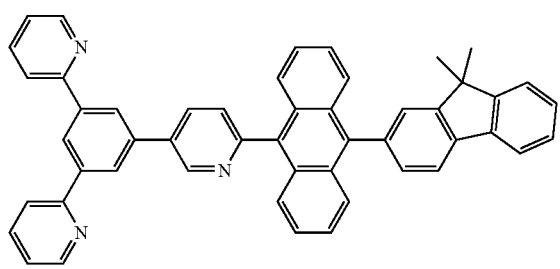
212
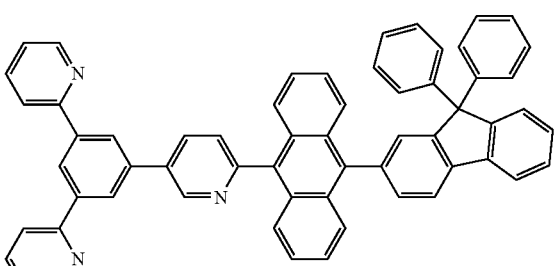

213
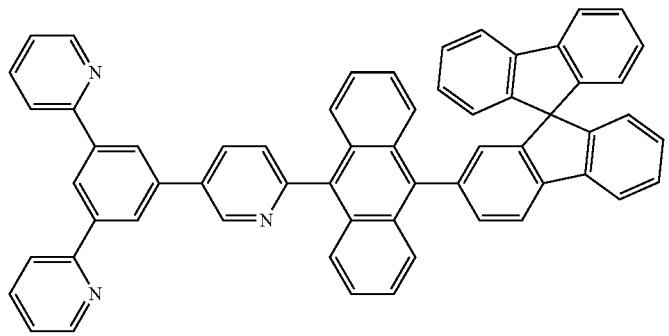
214
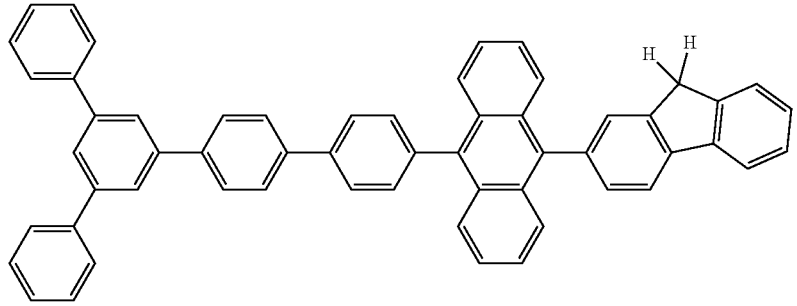
215
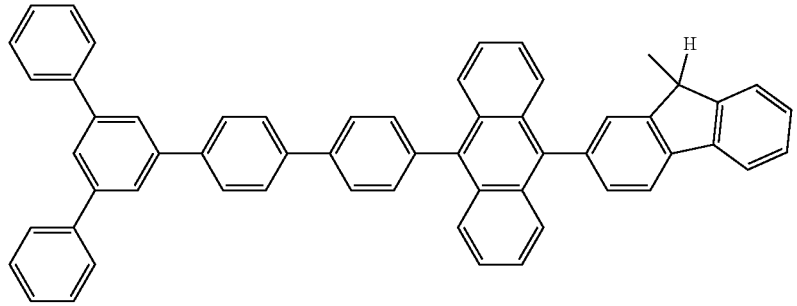
216
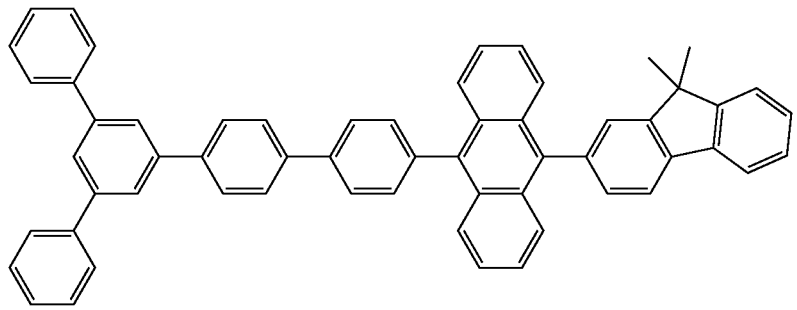
217
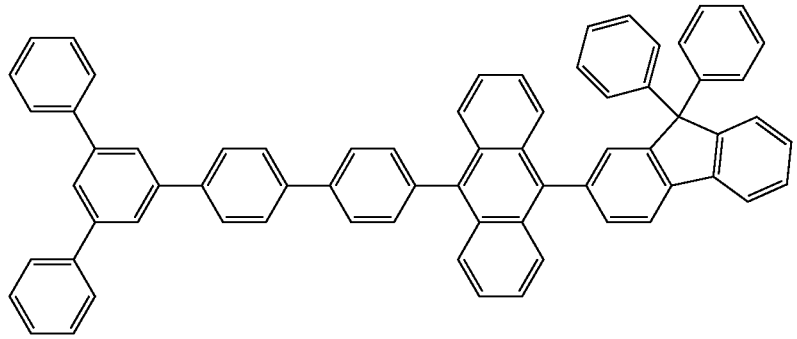

-continued
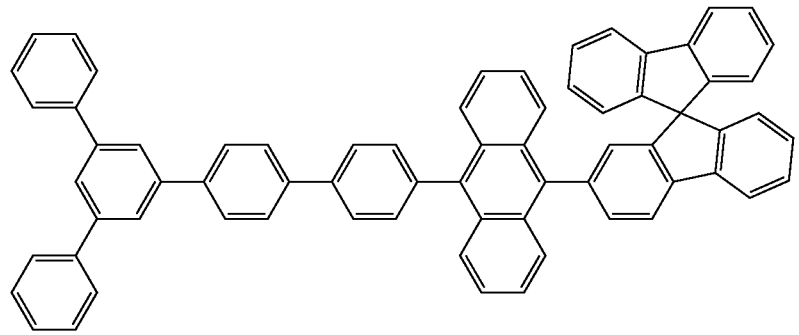
218
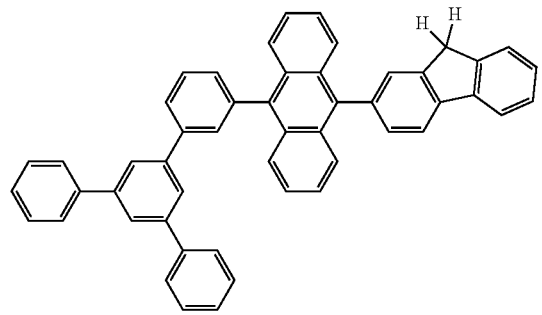
219
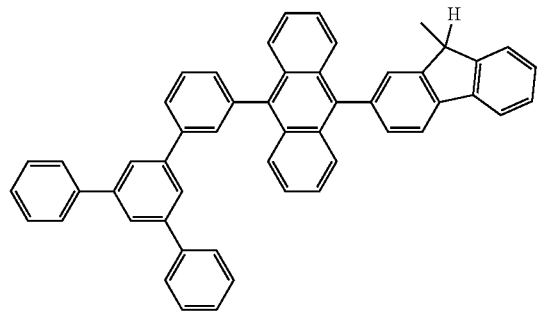
220
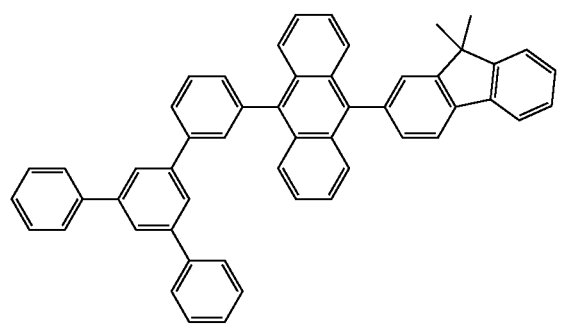
221
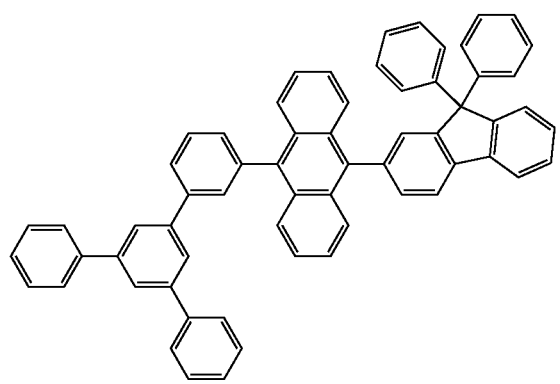
222
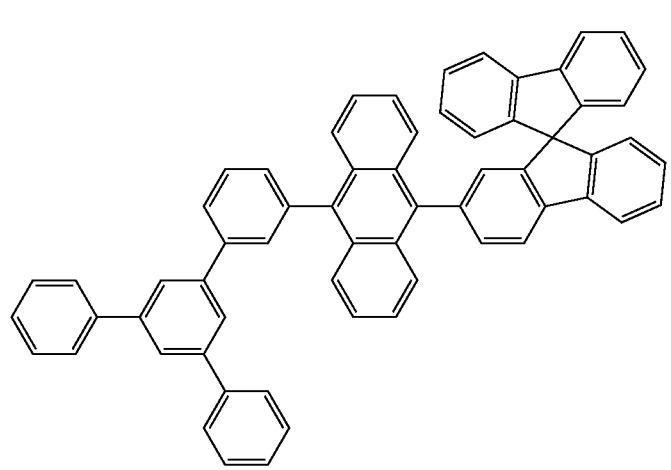
223

The organic electronic material provide in the present invention can be used to make OLED, which comprises an anode, a cathode, and a layer or multiple layers of organic layers. The said organic layer includes at least one layer of said organic electronic material with the structural formula I.

The said multiple organic layers are hole injection layer, hole transport layer, light emitting layer, hole blocking layer and electron transport layer, respectively, and in particular, not all organic layers are necessary according to the demands.

The said hole transport layer, electron transport layer and light emitting layer contain the said organic material with the structural formula 1.

The materials of the hole transport layer and hole injection layer in the present invention should have good hole transport performance, which can effectively transport the holes from the anode to the organic light emitting layer. The materials used can include small molecule and polymer organic materials, including but not limited to tri-aromatic amine compounds, benzidine compounds, thiazole compounds, oxazole compounds, imidazole compounds, fluorene compound, phthalocyanine compounds, hexanitrile hexaazatriphenylene, 2,3,5,6-tetrafluoro-7,7',8,8'-tetracyanoanthraquinodimethane dimethyl-p-benzoquinone (F4-TCNQ), polyvinyl carbazole, polythiophene, polyethylene, polyethylene sulfonic acid.

The organic light emitting layer in the present invention contains, in addition to the compounds with the structural formula (I), the following but not limited to the following compounds: naphthalene compounds, pyrene compounds, fluorene compounds, phenanthrene compounds, chrysene compounds, fluoranthene compounds, anthracene compounds, dibenzanthracene compounds, perylene compound, bi-aryl vinyl compounds, triphenylamine vinyl compounds, amine compounds, benzimidazole compounds, furan compounds and organic metal chelate compounds.

The organic electron transport material of the organic electronic devices in the present invention should have good electron-transport performance, which can efficiently transfer electrons from the cathode to the light emitting layer. These materials can select the following compounds, but not limited to oxa oxazole, thiazoles, triazole compounds, tri-diazoxide compounds, tri-aza benzene compounds, quinoxaline compounds, dinitrogen anthracene compounds, silicon-containing heterocyclic compounds, quinoline compounds, phenanthroline compounds, metal chelates, fluoro-substituted benzene compounds.

One electron injection layer can be added to the organic electronic device of the present invention as required. The electron injection layer may effectively inject the electrons from the cathode into the organic layer, mainly selected from alkali metals or alkali metal compounds, or selected from alkaline earth metals or alkaline earth metal compounds, including but not limited to the following: lithium, lithium fluoride, lithium oxide, lithium nitride, 8-hydroxyquinoline lithium, cesium, cesium carbonate, 8-hydroxyquinoline cesium, calcium, calcium fluoride, calcium oxide, magnesium, magnesium fluoride, magnesium carbonate, magnesium oxide.

Experimental results show that, the organic electronic material with structural formula (I) has a good thermal stability, high light-emitting efficiency, high purity of light-emitting. The OLEDs made from this organic light-emitting material will have advantages of good light-emitting efficiency, excellent color purity and long lifetime.

DETAILED DESCRIPTIONS OF THE PREFERRED EMBODIMENTS

Figure 1:
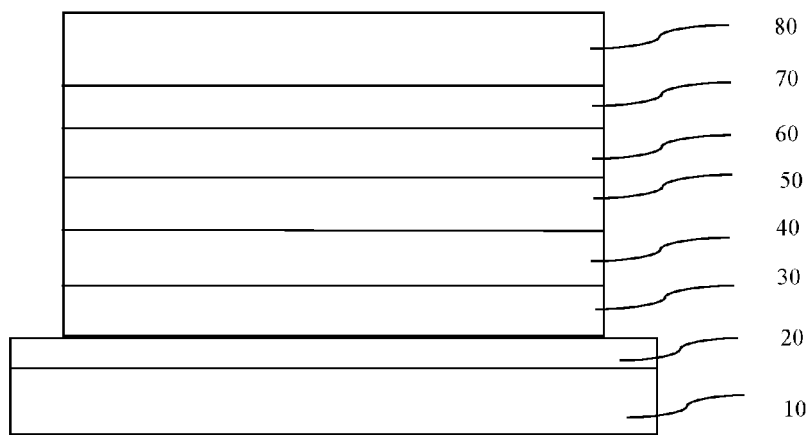
FIG. 1 is a structural charge of the device, of which, 10 denotes a glass substrate, 20 denotes an anode, 30 denotes hole injection layer, 40 denotes hole transport layer, 50 denotes light emitting layer, 60 denotes electron transport layer, 70 denotes electron injection layer, 80 denotes cathode.

In the following, the present invention is described in details by combining the following examples.

(The compounds 1a, 1b, 1e, 1h, 3a, 89a are common materials available in the markets)

Embodiment 1

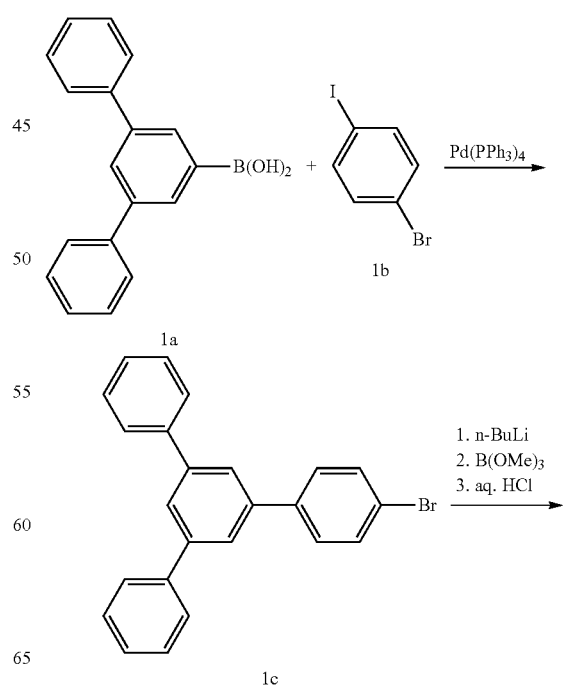

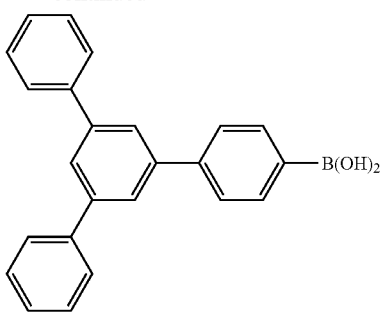

1d

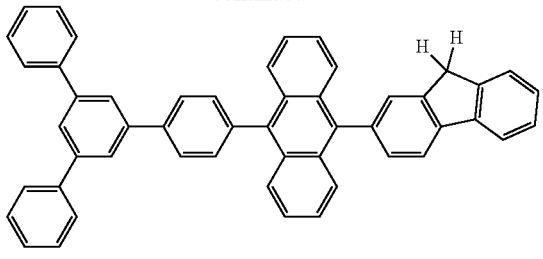

1

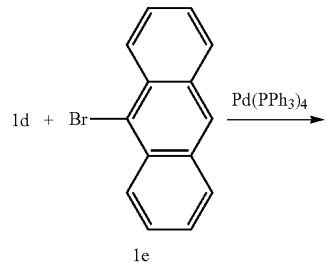

1d + Br—<span>[anthracene]</span> →<sup>Pd(PPh₃)₄</sup>

1e

Synthesis of Intermediate 1c

Add 1a (240.00 g, 0.88 mol), 1b (496.32 g, 1.76 mol), Pd(PPh₃)₄ (20.35 g, 17.60 mmol), potassium carbonate (302.52 g, 2.20 mol), toluene (2400 mL), pure water (1200 mL) to a reaction flask. Start to heat after extracting air for three times, and when the reaction solution temperature reaches 95-105V, maintain it for 8-12 h; take samples for TLC and HPLC, to completely react. Stop heating and cool down to 20-30° C., perform suction filtration to separate the organic layer from filtrate. Extract the aqueous layer with ethyl acetate, combine the organic layer, then wash with water, dry by anhydrous magnesium sulfate, and perform suction filtration, to get the filtrate. Concentrate the filtrate to get a dark yellow solid crude product. The crude product is recrystallized from petroleum ether to get an off-white solid product, with a yield of 90% and a purity of 95%.

Synthesis of Intermediate 1d

Add 1c (302 g, 0.78 mol), B(OEt)₃ (142 g, 0.97 mol), n-BuLi/THF (1.6 M, 600 mL), and anhydrous THF (3000 mL) at appropriate ratio to a reaction flask. After extracting with nitrogen for three times, cool down until the reaction solution temperature is −75~−65° C., slowly add n-BuLi/THF solution dropwise and control the temperature at −75~−65° C.; after dripping, continue to maintain this temperature for reaction 0.5-1 h. Then add appropriate amount of B(OEt)₃ dropwise, to control the reaction solution temperature at −75~−65° C., after dripping, continue to maintain this temperature for reaction 0.5-1 h. Then transfer the solution to room temperature for naturally heating reaction 4-6 h, then add 2M dilute hydrochloric acid to adjust the PH value to 2-3, after stirring about 1 h, stop the reaction. Add ethyl acetate to extract the solution, and the aqueous layer is extracted by EA. The organic layers are combined and dried over anhydrous magnesium sulfate, then suction filtration is conducted. The filtrate is concentrated to get an off-white solid product, with a purity of 95% and a yield of 62.5%.

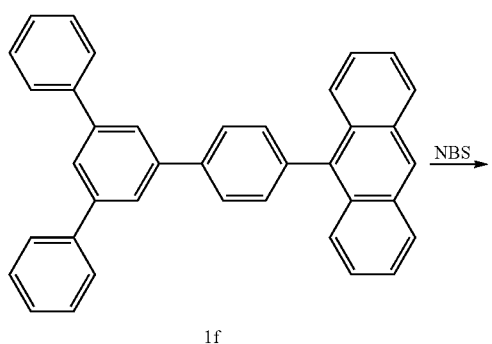

1f

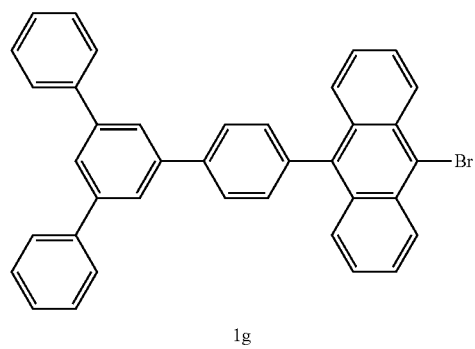

1g

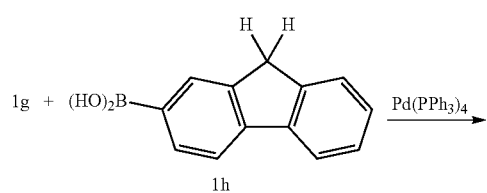

Synthesis of Intermediate 1f

Add 1d (150 g, 0.43 mol), 1e (500 g, 0.86 mol), Pd(PPh₃)₄ (5.0 g, 0.44 mmol), potassium carbonate (130 g, 0.92 mol), toluene (1000 mL), pure water (500 mL) to a reaction flask. Start to heat after extracting nitrogen for three times, and when the reaction solution temperature reaches 95-105° C., maintain it for 8-12 h; take samples for TLC and HPLC, to completely react. Stop heating and cool down to 20-30° C., perform suction filtration to separate the organic layer from filtrate. Extract the aqueous layer with ethyl acetate, combine the organic layers, dry by anhydrous magnesium sulfate, and perform suction filtration. The filtrate is concentrated to get dark yellow solid crude product, with a purity of 80% and a yield of 78.1%.

Synthesis of Intermediate 1g

Add 1f (210 g, 0.42 mol), NBS (135 g, 0.71 mol), DMF (5 L) to a reaction flask. Start to heat after extracting nitrogen for three times, and when the reaction solution temperature reaches 60-65° C., maintain it for 6-8 h; take samples for TLC and HPLC, to completely react. Stop heating and cool down to 20-30° C., then pour the reaction solution to ice-water to separate dark yellow solid, and then perform suction filtration to get yellow solid and bake to obtain 1 g of crude product. Add the crude product to DCM/MeOH until the solution becomes slightly turbid, continue to stir for about 30 min, to separate out a large amount of solid, then perform suction filtration to get pale yellow solid product, with a yield of approximate 54.05% and a purity of 98.5%.

$^1$H NMR (300 MHz, CDCl$_3$) δ 8.64 (d, J=8.8 Hz, 2H), 7.99-7.90 (m, 4H), 7.87 (t, J=1.6 Hz, 1H), 7.78 (dd, J=9.3, 2.3 Hz, 6H), 7.61 (ddd, J=8.8, 6.5, 1.1 Hz, 2H), 7.56-7.48 (m, 6H), 7.46-7.38 (m, 4H).

$^{13}$C NMR (76 MHz, CDCl$_3$) δ 142.67 (s), 142.03 (s), 141.26 (s), 140.69 (s), 137.83 (s), 137.52 (s), 131.87 (s), 131.24 (s), 130.44 (s), 129.09 (s), 128.80 (s), 128.38-127.40 (m), 127.18 (s), 126.05-125.21 (m), 123.08 (s), 77.74 (s), 77.31 (s), 76.89 (s), 30.10 (s).

Synthesis of Compound 1

Add 1 g (9.5 g, 16.92 mmol), 1h (6.41 g, 30.51 mmol), Pd(PPh$_3$)$_4$ (1.5 g, 1.3 mmol), potassium carbonate (5.84 g, 42.3 mmol), toluene (150 mL) and pure water (75 mL) to a 500 ml three-necked flask. After extracting nitrogen for three times, reaction occurs at 105° C. The time of reaction stop is around 12 h, which is detected by liquid phase. The reaction solution is earth yellow of catalyst at the beginning, slowly turning into a yellow solution. After reaction stops, the upper layer is bright and light yellow, and the lower layer is water. After reaction stops, filter the solution, wash the filter residues with ethyl acetate until no product in the residue, then collect the filtrate, spin-dry, to separate out a large amount of off white solid. Collect the filter residue to dry, to get the target product, with purity of 98%; after vacuum sublimation, gray-white solid powder with purity of 99.5% is obtained.

$^1$H-NMR (300 MHz, CDCl$_3$) δ 8.10-8.21 (d, 2H), 7.96-7.98 (dd, 3H), 7.87-7.89 (m, 2H), 7.81-7.86 (m, 4H), 7.78-7.81 (d, 4H), 7.62-7.65 (m, 2H), 7.59 (s, 1H), 7.51-7.57 (m, 5H), 7.45-7.48 (m, 2H), 7.36-7.43 (m, 7H), 3.88 (s, 2H).

Embodiment 2

Synthesis of Compound 3

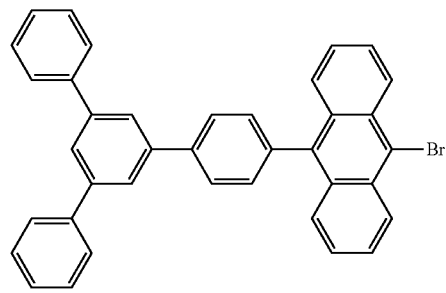

1g

+

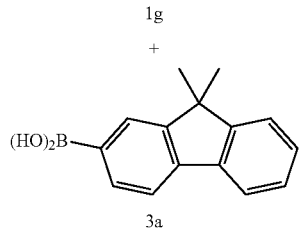

3a

Pd(PPh$_3$)$_4$ →

-continued

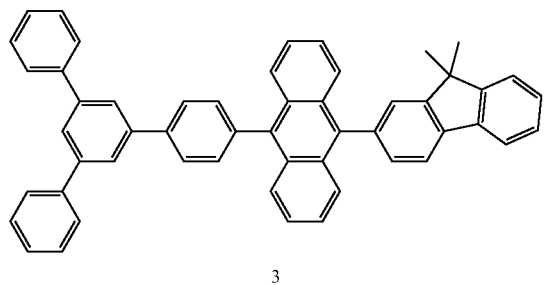

3

Add 1 g (9.5 g, 16.92 mmol), 3a (7.25 g, 30.46 mmol), Pd(PPh$_3$)$_4$ (1.5 g, 1.3 mmol), potassium carbonate (5.84 g, 42.3 mmol), toluene (150 mL) and pure water (75 mL) to a 500 ml three-necked flask. After extracting nitrogen for three times, reaction occurs at 105° C. The time of reaction stop is around 12 h, which is detected by liquid phase.

The reaction solution is earth yellow of catalyst at the beginning, slowly turning into a yellow solution. After reaction stops, the upper layer is bright and light yellow, and the lower layer is water. After reaction stops, filter the solution, wash the filter residues with ethyl acetate until no product in the residue, then collect the filtrate, spin-dry, to separate out a large amount of off white solid. Collect the filter residue to dry, to get the target product, with purity of 98%; after vacuum sublimation, gray-white solid powder with purity of 99.7% is obtained.

$^1$H-NMR (300 MHz, CDCl$_3$) δ 8.1-8.2 (d, 2H), 7.96-7.99 (dd, 3H), 7.88-7.89 (m, 2H), 7.81-7.86 (m, 4H), 7.78-7.81 (d, 4H), 7.61-7.65 (m, 2H), 7.59 (s, 1H), 7.51-7.56 (m, 5H), 7.46-7.48 (m, 2H), 7.35-7.43 (m, 7H), 1.61 (s, 6H).

Embodiment 3

Synthesis of Compound 89

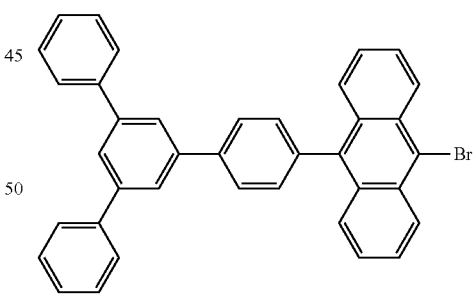

1g

+

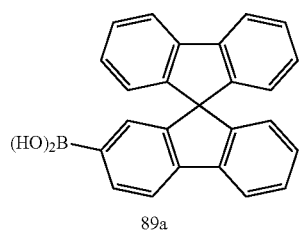

89a

Pd(PPh$_3$)$_4$ →

-continued

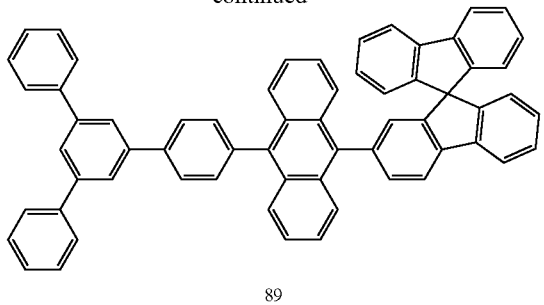

89

Add 1 g (10.0 g, 17.8 mmol), 89a (7.1 g, 19.6 mmol), Pd(PPh$_3$)$_4$ (432.2 mg, 0.35 mmol), K2CO3 (6.14 g, 44.5 mmol), toluene (300 mL) and water (150 mL) successively to a reaction tank. After deoxygenization of the device and introduction of nitrogen, heat to 100° C. for reaction overnight, apply to the plates at a ratio of DCM:PE=1:5. The product gives out intensive blue light under UV light at 365 nm wavelength, with the Rf value at about 0.2. Perform suction filtration with the reaction solution, wash the filter cake with ethyl acetate (100 mL) twice and separate. Extract the aqueous layer with ethyl acetate (100 mL) once, combine the organic layers, then wash the organic layer once with water (200 mL). spin dry to remove the solvent. The crude product is recrystallized from 120 ml DCM/MeOH, then suction filtration is performed to get 13.1 g yellow solid powder, with a purity of 98.7% and a yield of 92.2% yield. After vacuum sublimation, a slight yellow solid powder with purity of 99.7% is obtained. m/z=797.

Figure 2:
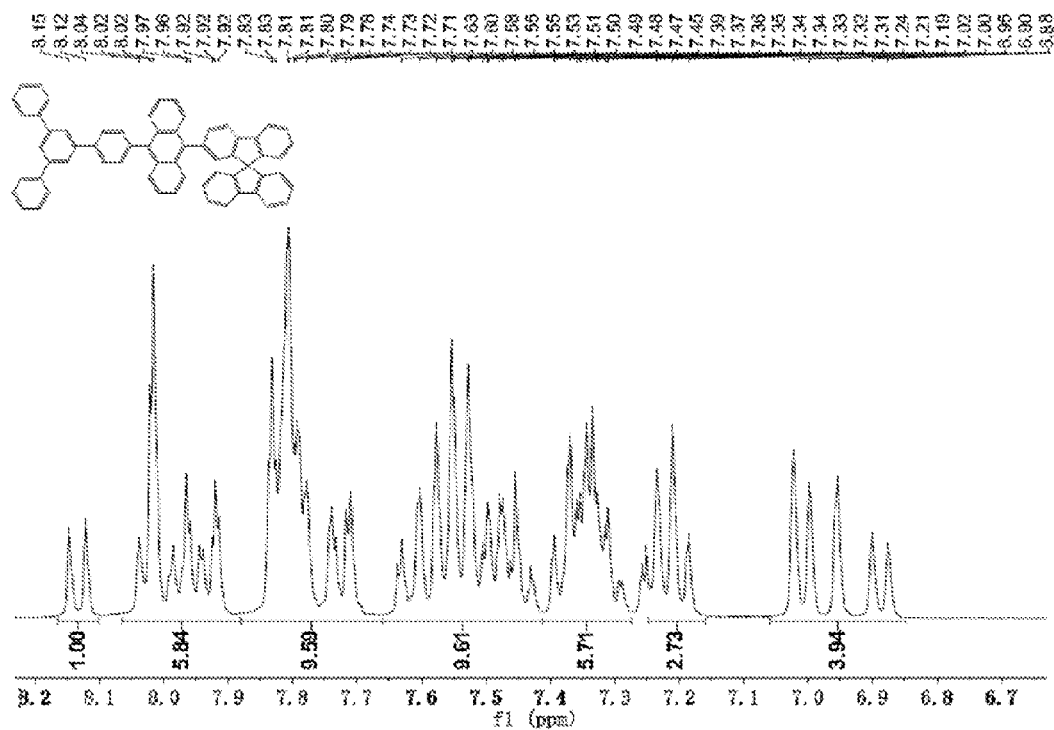
FIG. 2 is the $^1$H NMR diagram of compound 89.
Figure 3:
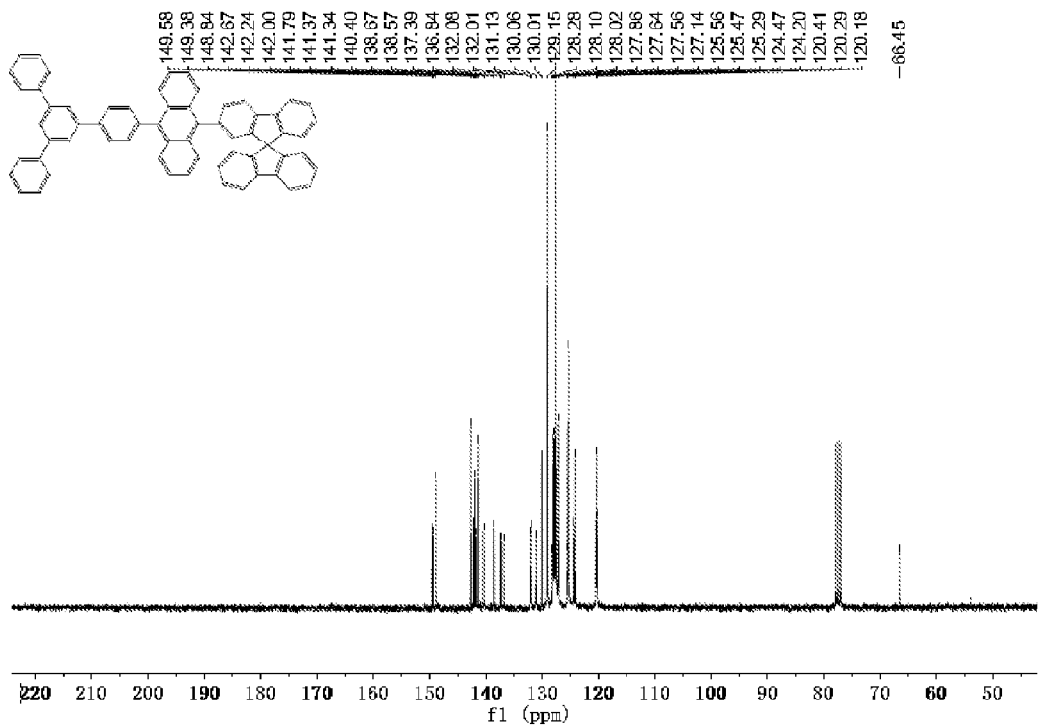
FIG. 3 is the $^{13}$C NMR diagram of compound 89.
Figure 4:
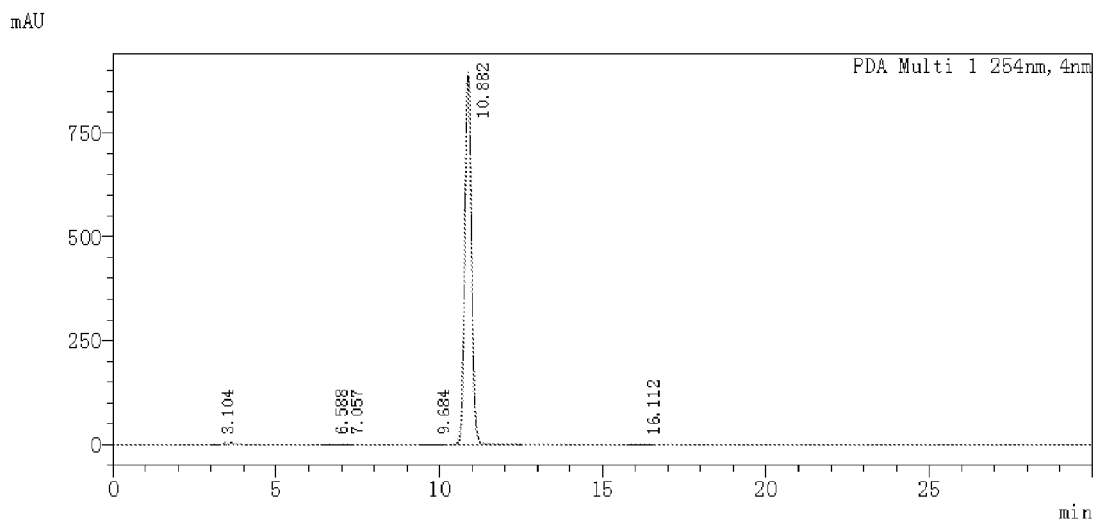
Figure 5:
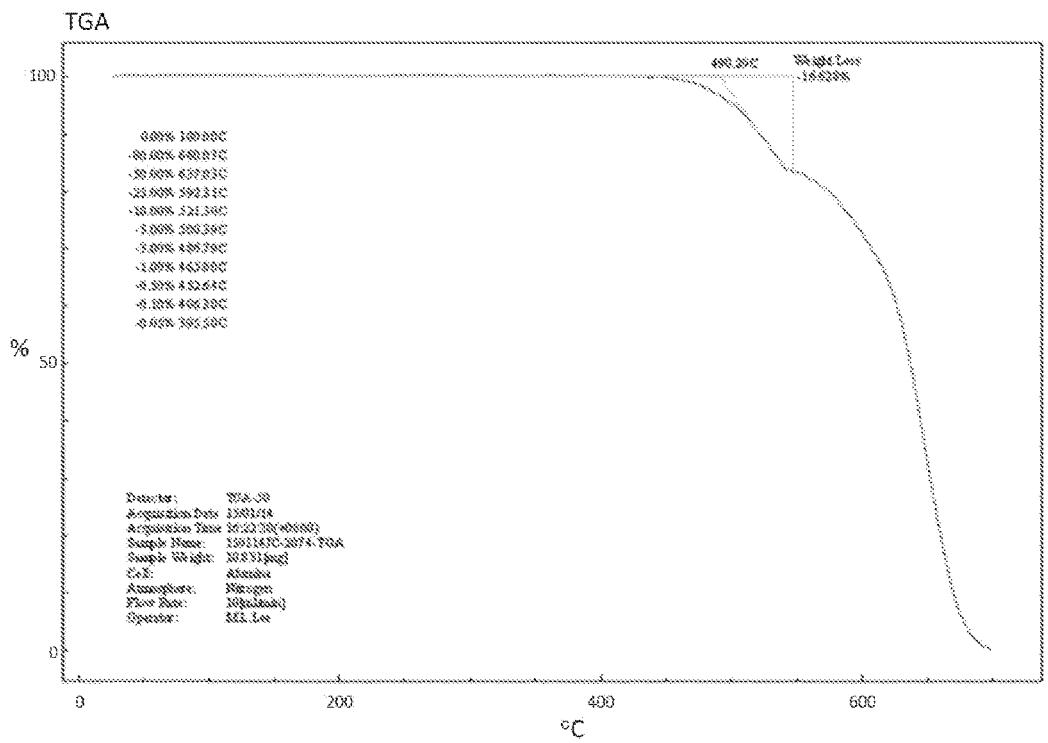
FIG. 5 is the TGA map of compound 89.
Figure 6:
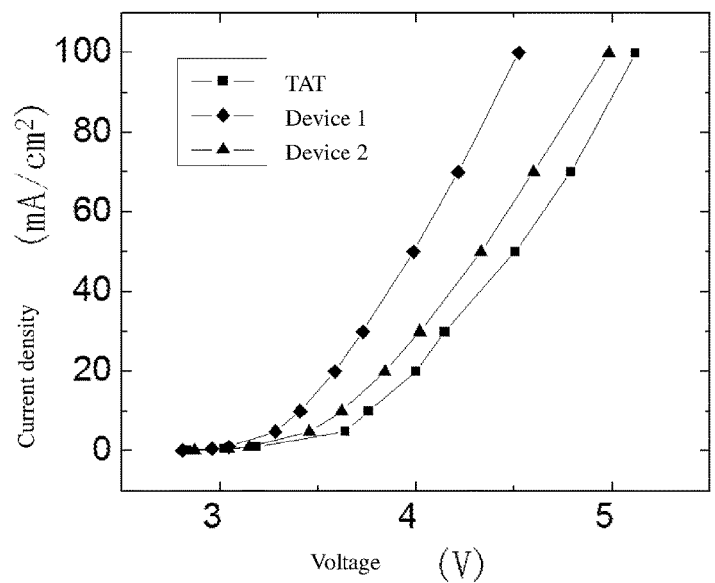
FIG. 6 shows the voltage-current density curves of Embodiments 4 and 5 and Comparative Example 1.
Figure 7:
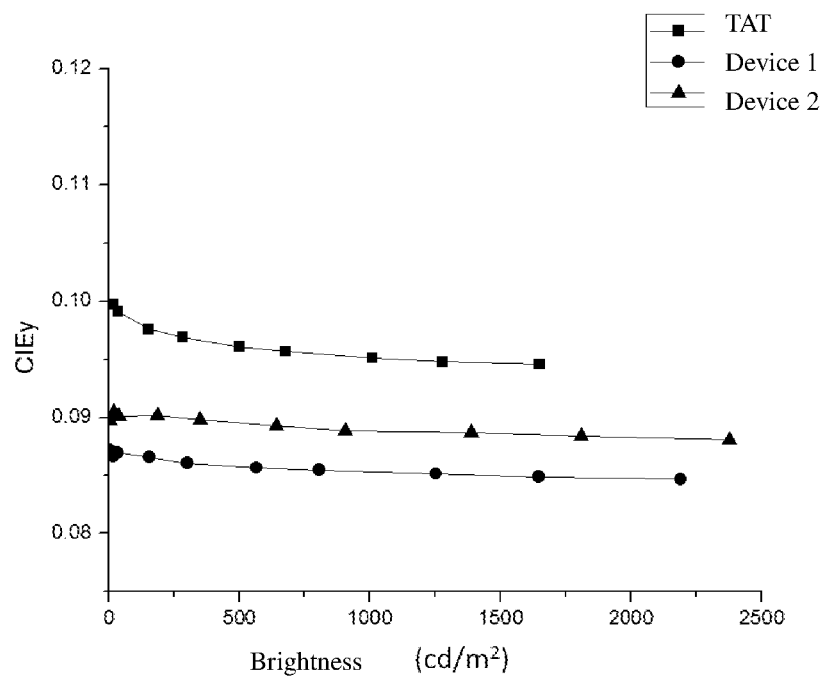
FIG. 7 shows the brightness –CIEy plot of Embodiments 4 and 5 and Comparative Example 1.
Figure 8:
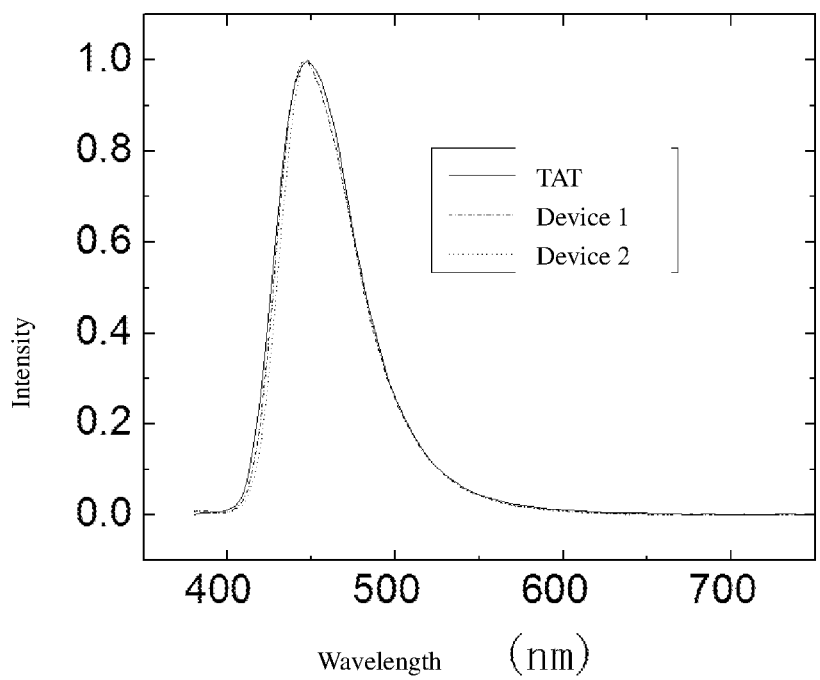
FIG. 8 shows the light-emitting spectra of Embodiments 4 and 5 and Comparative Example 1.
Figure 9:
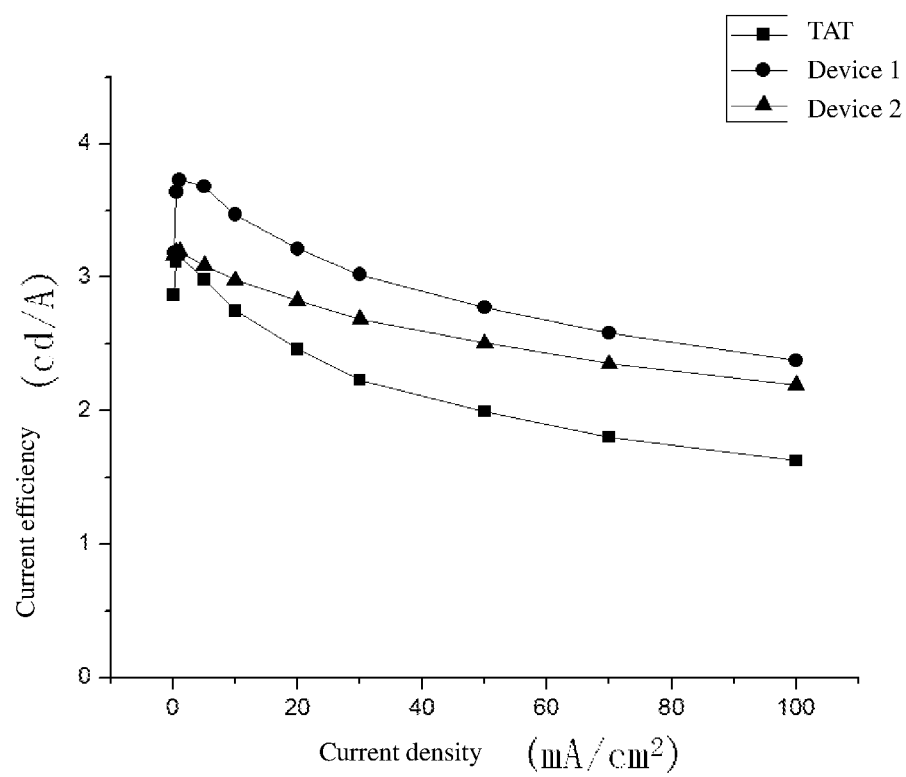
FIG. 9 shows the current density-current efficiency curves of Embodiments 4 and 5 and Comparative Example 1.

As shown from FIG. 2 and FIG. 3, the hydrogen spectra and carbon spectra of compound 89 are completely consistent with the structures. From the high performance liquid chromatogram of compound 89 in FIG. 4, the product made by the synthesis method in the invention has high purity. According to the thermal gravametric analysis of compound 89 in FIG. 5, the decomposition temperature of this type of compound is higher than 400 degrees centigrade, indicating that it has very high thermal stability.

Embodiment 4

Preparation of OLED1
Prepare OLED by the Organic Electronic Material in the Present Invention Firstly, the ITO transparent conductive glass substrate 10 (with anode 20 above) is washed with detergent solution and deionized water, ethanol, acetone, deionized water in sequence, then treated with oxygen plasma for 30 seconds.

Then, perform vacuum evaporation of 10 nm HAT-CN$_6$ in ITO, which is used as the hole injection layer 30.

Then, perform vacuum evaporation of NPB, to form 30 nm thick of hole transport layer 40.

Then, perform vacuum evaporation of 30 nm thick of compound 3 in hole transport layer, which is used as light emitting layer 50.

And then, perform vacuum evaporation of 15 nm thick of TPBi in light emitting layer, which is used as electron transport layer 60.

Finally, perform vacuum evaporation of 15 nm BPhen:Li as electron injection layer 70, and vacuum evaporation of 150 nm Al as the device cathode 80.

The voltage of the device made in 20 mA/cm2 of operating current density is 3.58 V, the current efficiency is 3.21 cd/A. The CIEy at the luminance of 1000 cd/m2 is 0.0853. It emits blue light.

The Said Structural Formula of the Device

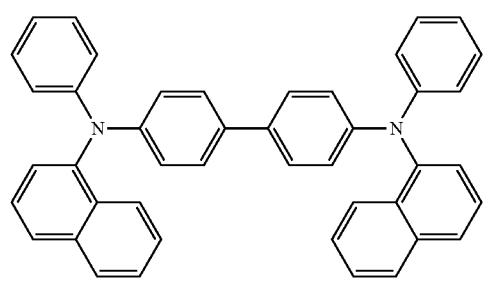

NPB

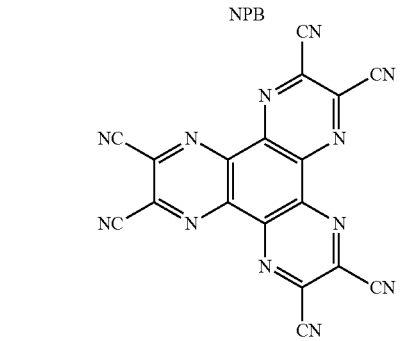

HAT—CN$_6$

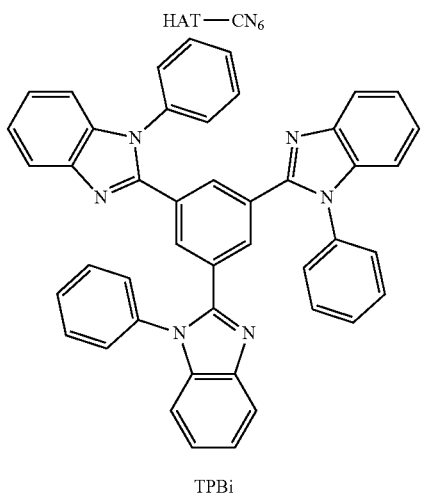

TPBi

Embodiment 5

Preparation of OLED2

Procedures are the same as Embodiment 4. OLED is made using compound 89 instead of compound 3 The voltage of the device made in 20 mA/cm2 of operating current density is 3.84 V, the current efficiency is 2.83 cd/A. The CIEy at the luminance of 1000 cd/m2 is 0.0888. It emits blue light.

Comparative Example 1

The procedures are the same as Embodiment 4. OLED is made using the following compound TAT instead of compound 3, for comparison.

TAT Structural Formula

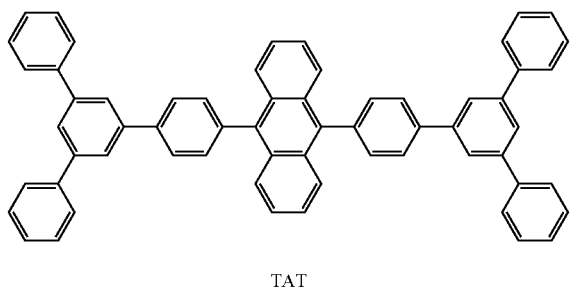 [SMILES: c1ccc(-c2cc(-c3ccccc3)cc(-c3ccc(-c4c5ccccc5c(-c5ccc(-c6cc(-c7ccccc7)cc(-c7ccccc7)c6)cc5)c5ccccc45)cc3)c2)cc1 ; "TAT"]

TAT

The voltage of the device made in 20 mA/cm2 of operating current density is 4.00 V, the current efficiency is 2.46 cd/A. The CIEy at the luminance of 1000 cd/m2 is 0.0952. It emits blue light.

The embodiments 4 and 5 are the specific applications of the material in the present invention. The blue light-emitting, efficiency and luminance of the devices are higher than those in the comparison example. Therefore, as stated above, the material in the present invention has high stability, and the OLED made in the invention has high efficiency and light purity.

The invention claimed is:

1. An organic electronic material comprising the following structural formula (I):

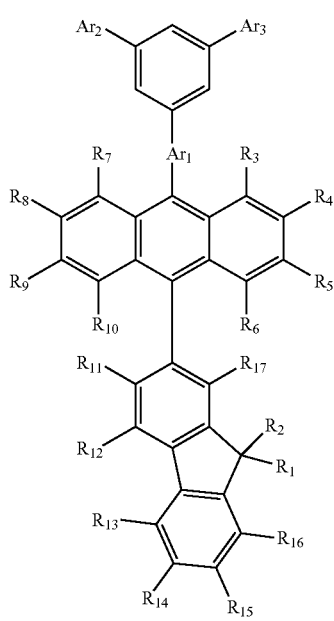

(I)

Wherein
$R_1$-$R_{17}$ independently represent hydrogen, halogen, cyano, nitro, $C_1$-$C_8$ alkyl, $C_1$-$C_8$ alkoxy, $C_2$-$C_8$ substituted or unsubstituted alkenyl, $C_2$-$C_8$ substituted or an unsubstituted alkynyl, $C_1$-$C_4$ alkyl substituted or unsubstituted phenyl, $C_1$-$C_4$ alkyl substituted or unsubstituted naphthyl, or combined $C_1$-$C_4$ alkyl substituted or unsubstituted fluorenyl; and
$Ar_1$-$Ar_3$ independently represent $C_1$-$C_4$ alkyl substituted phenyl, phenyl, pyridyl.

2. The organic electronic material according to claim 1, wherein
$R_1$-$R_2$ independently and preferably represent hydrogen, halogen, $C_1$-$C_4$ alkyl, $C_1$-$C_4$ alkyl substituted or unsubstituted phenyl, $C_1$-$C_4$ alkyl substituted or unsubstituted naphthyl, or combined $C_1$-$C_4$ alkyl-substituted or unsubstituted fluorenyl; and
$R_3$-$R_{17}$ may independently represent hydrogen, halogen, $C_1$-$C_4$ alkyl, $C_1$-$C_4$ alkyl substituted or unsubstituted phenyl, $C_1$-$C_4$ alkyl-substituted or unsubstituted naphthyl, preferably $Ar_1$-$Ar_3$ independently represent phenyl, tolyl, xylyl, t-butylphenyl.

3. The organic electronic material according to claim 2, wherein
$R_3$-$R_{17}$ preferably represents hydrogen, and
$R_1$ and $R_2$ may independently represent hydrogen, methyl, ethyl, propyl, isopropyl, t-butyl, phenyl, biphenyl, naphthyl, or combined fluorenyl; $Ar_1$-$Ar_3$ may independently represent phenyl, pyridyl, tolyl, xylyl.

4. The organic electronic material according to claim 3, wherein
$R_3$-$R_{17}$ represent hydrogen preferably;
$R_1$, $R_2$ independently represent hydrogen, methyl or combined fluorenyl; and
$Ar_1$, $Ar_2$, $Ar_3$ independently represent phenyl.

5. The organic electronic material according to claim 1, wherein its structure is as follows:

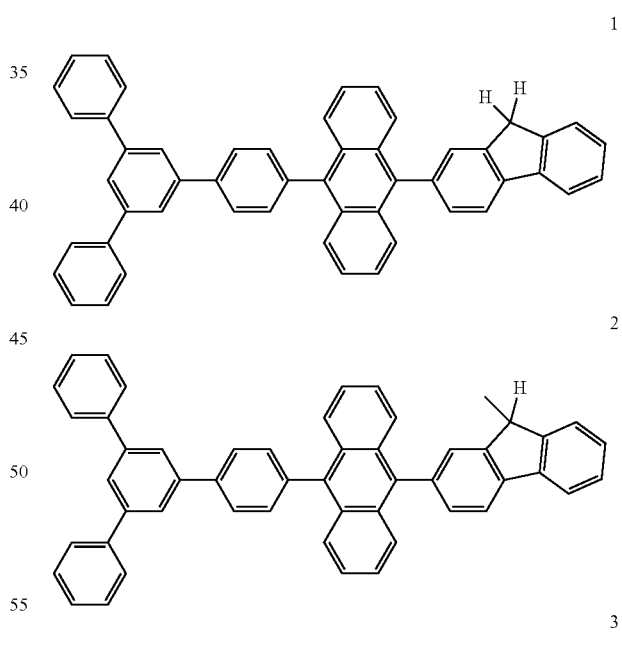

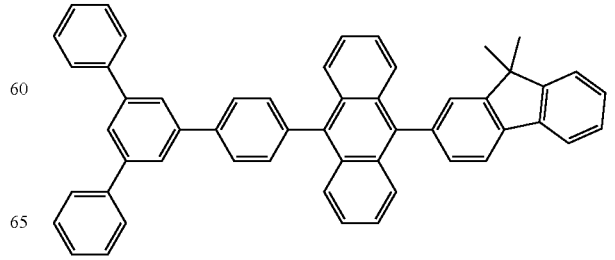

4
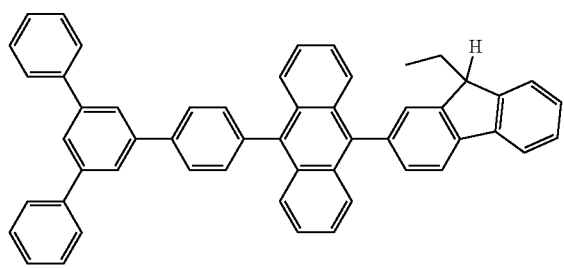
5
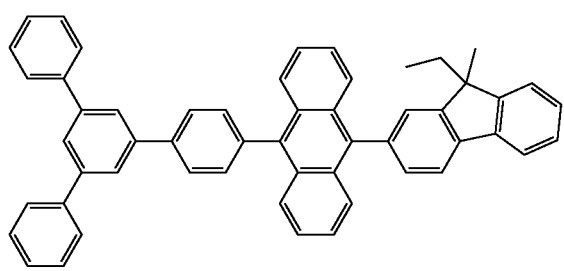
6
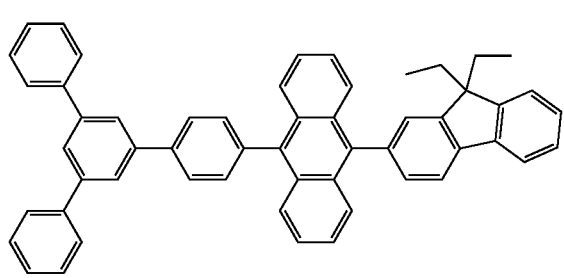
7
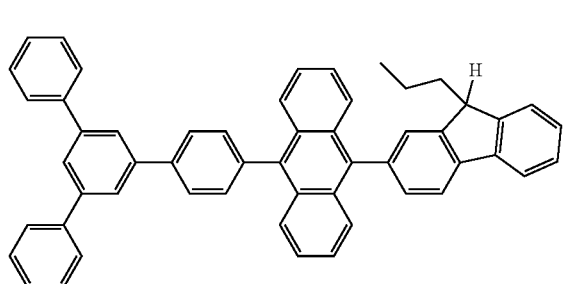
8
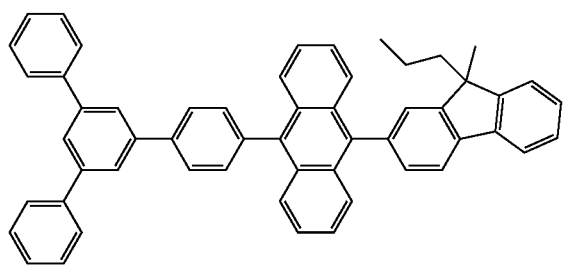
9
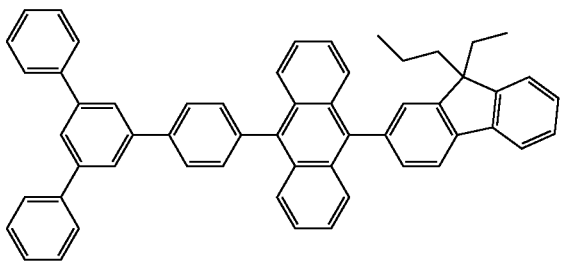
10
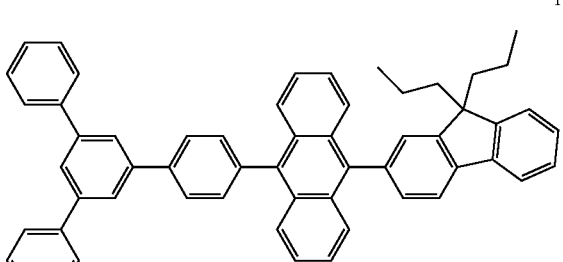
11
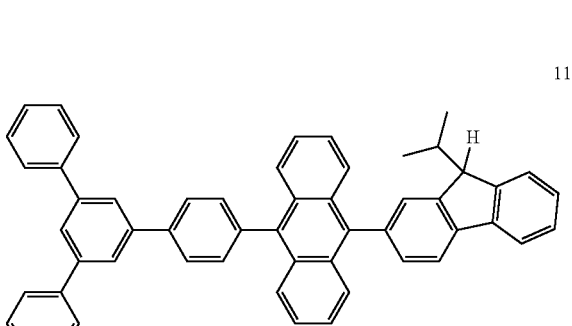
12
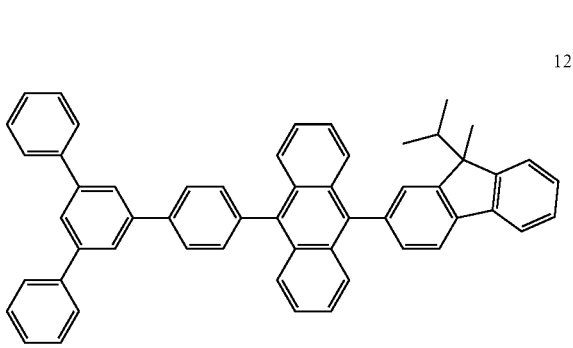
13
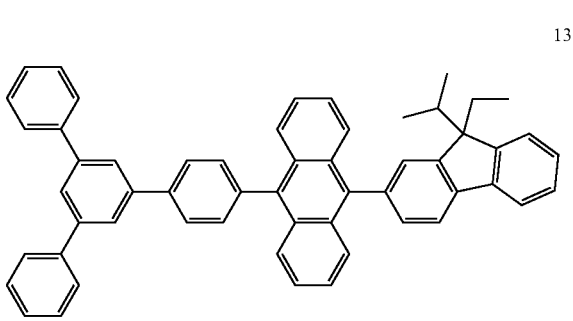

14
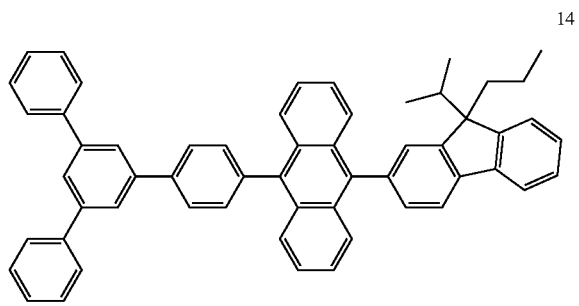
15
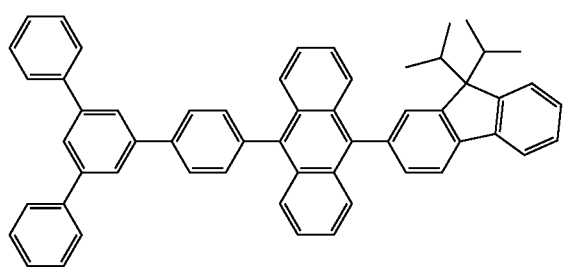
16
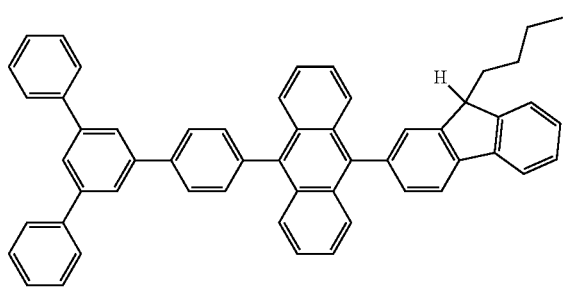
17
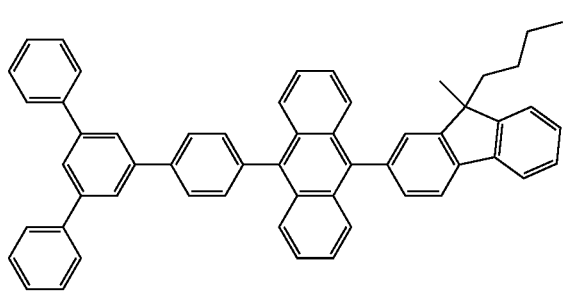
18
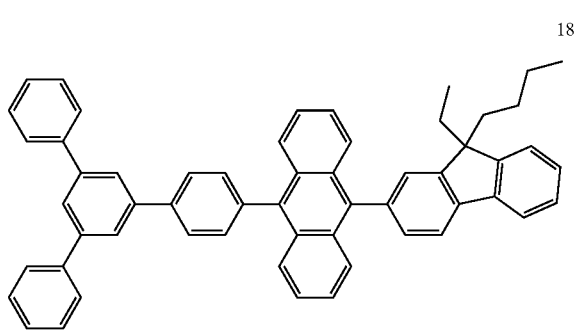
19
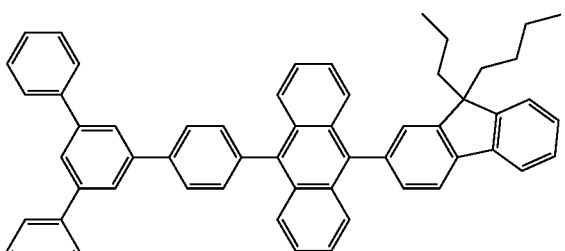
20
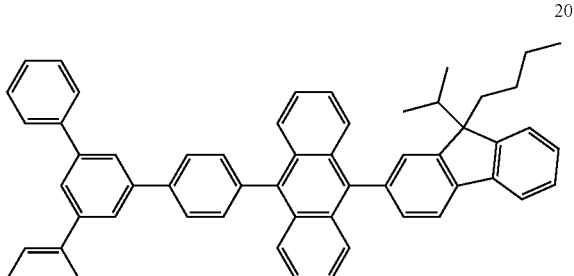
21
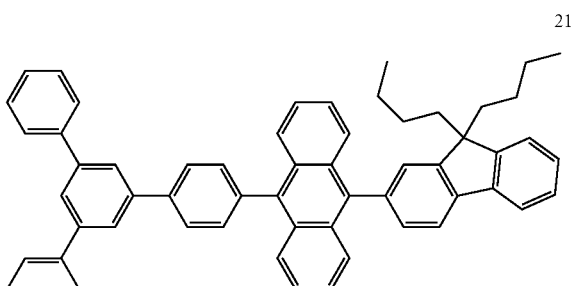
22
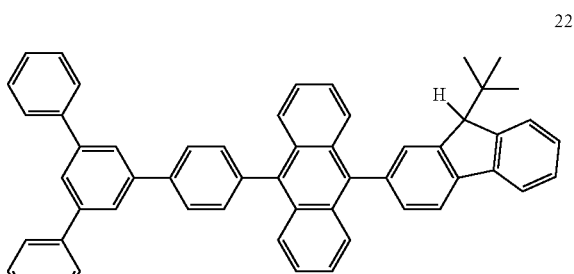
23
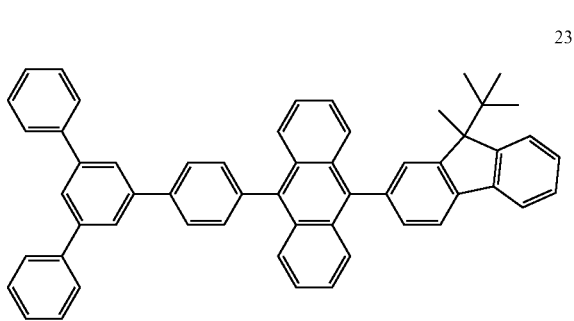

24
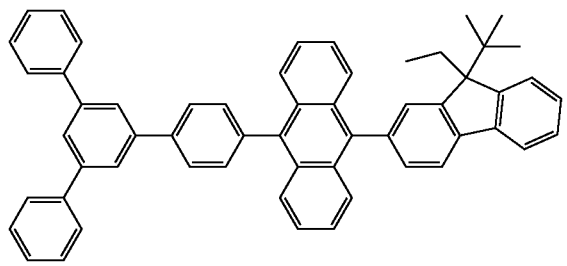
25
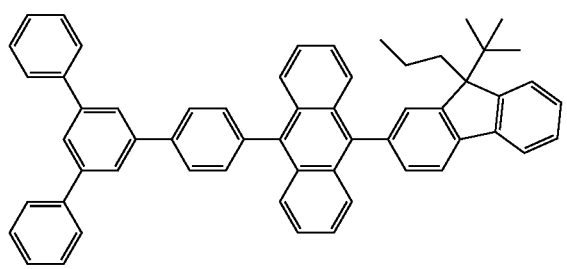
26
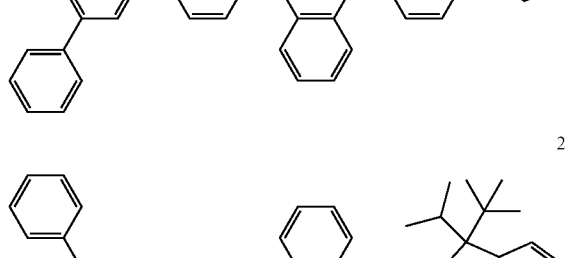
27
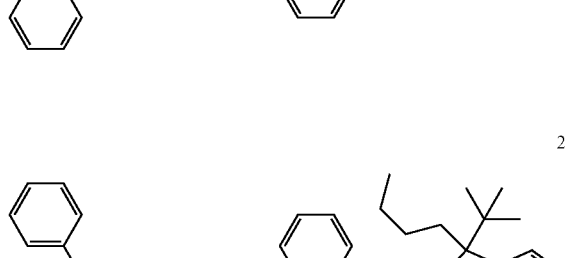
28
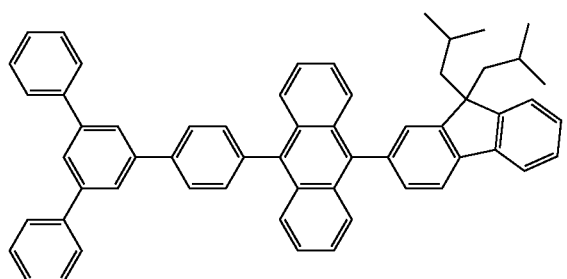
29
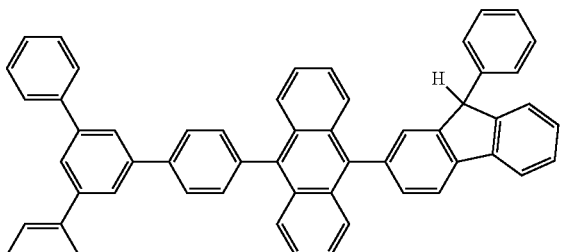
30
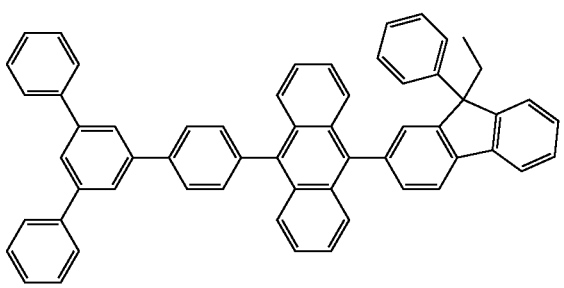
31
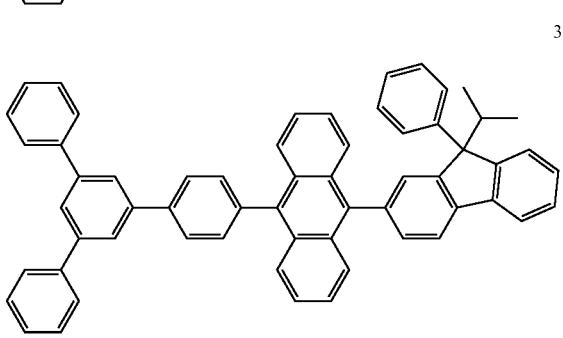
32
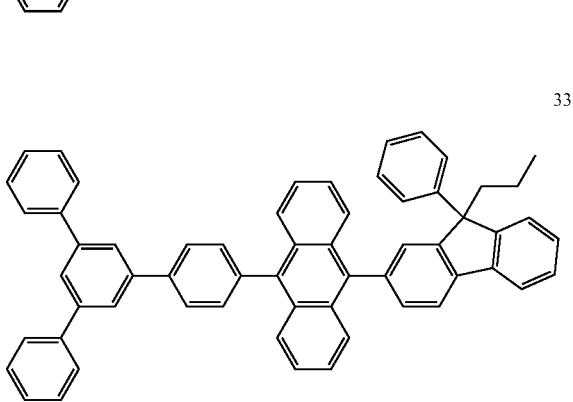
33

34
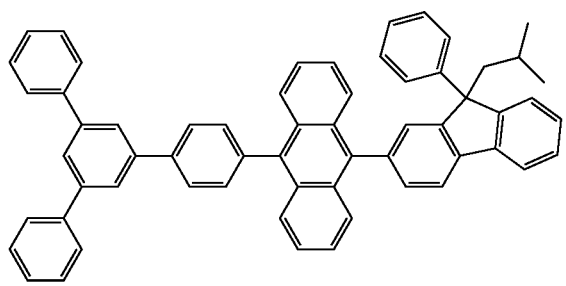
35
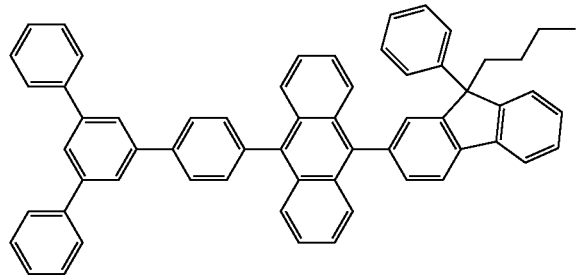
36
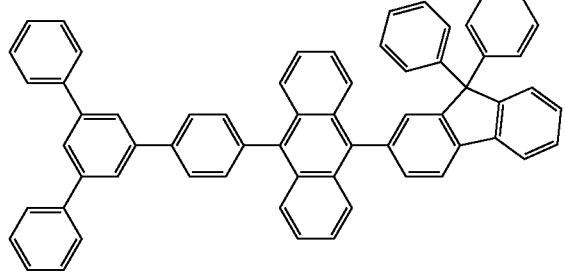
37
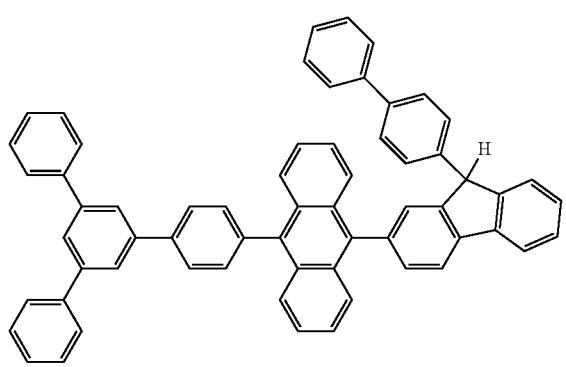
38
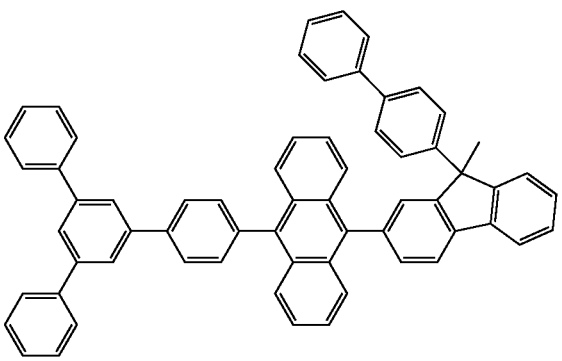
39
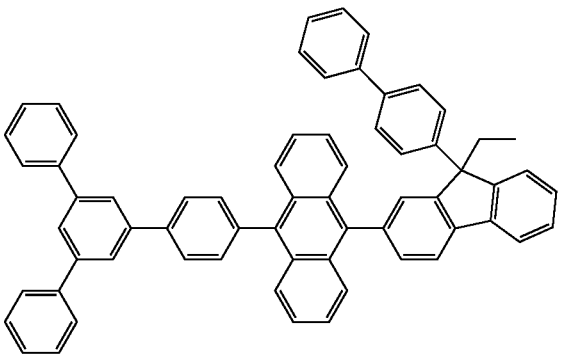
40
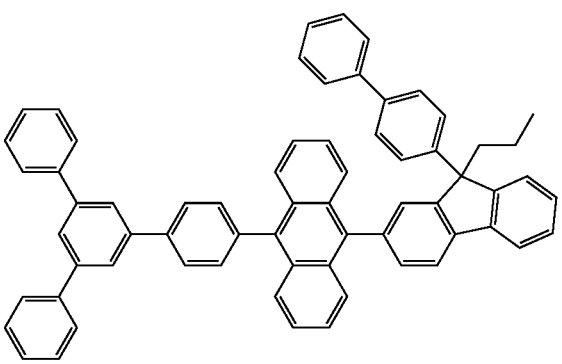
41
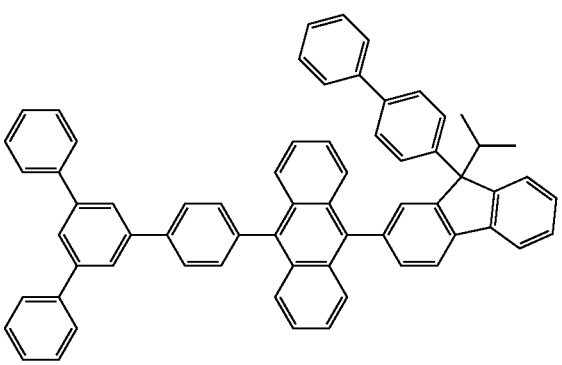

42
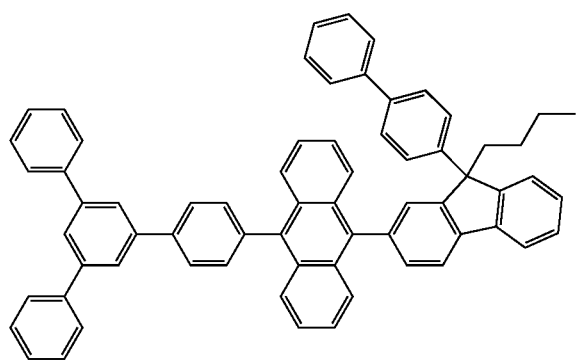
43
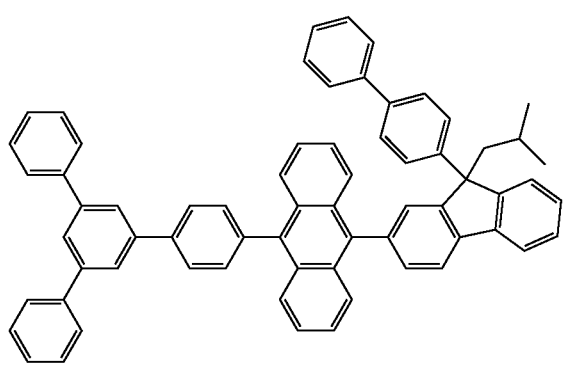
44
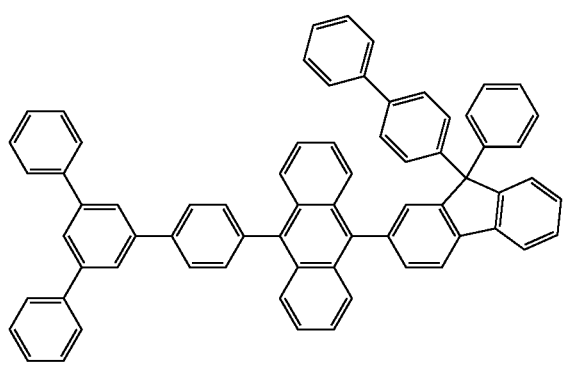
45
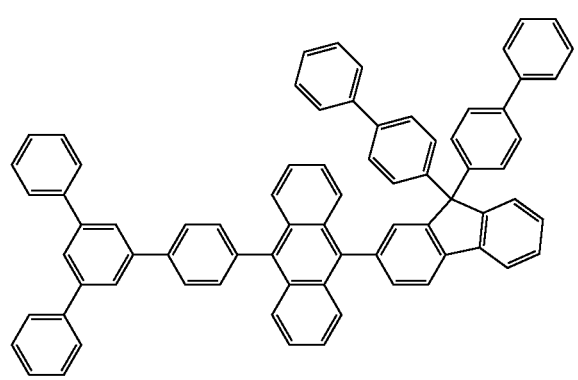
46
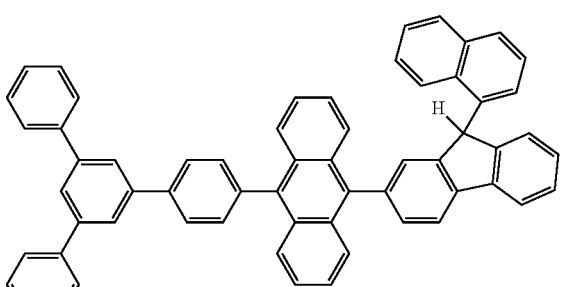
47
48
49
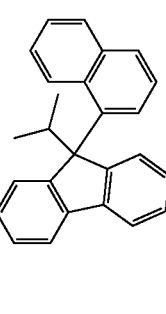

75
-continued
50
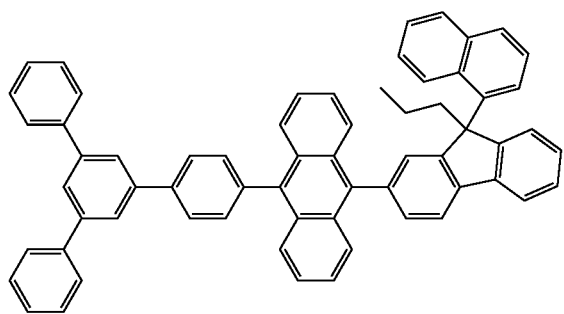
51
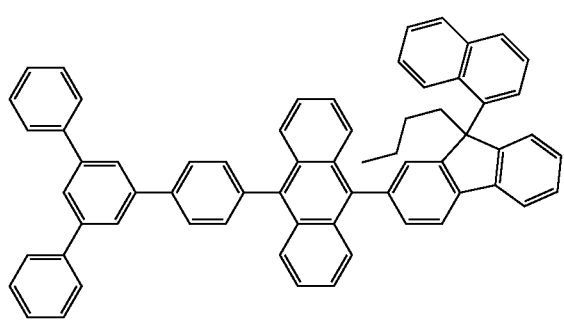
52
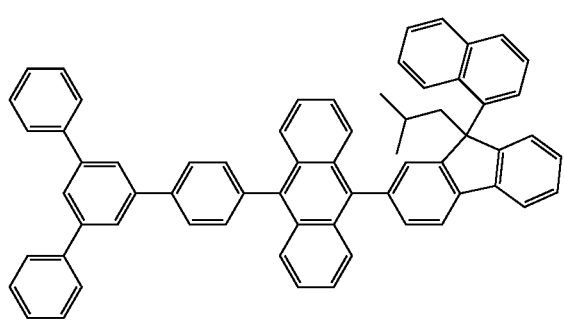
53
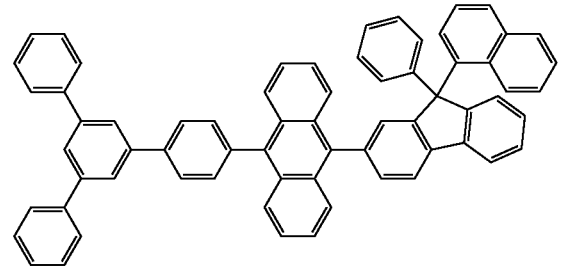
54
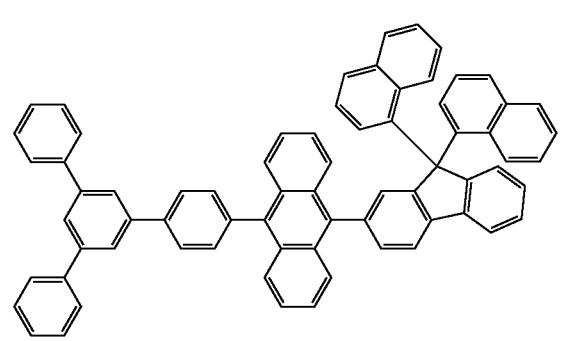
76
-continued
55
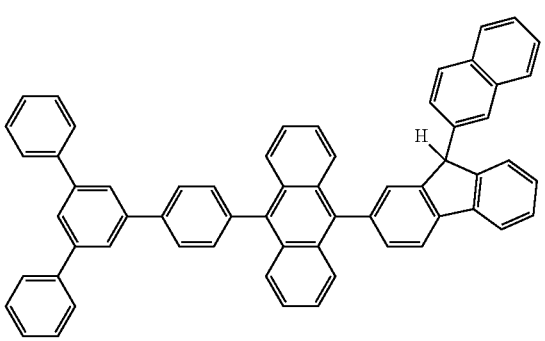
56
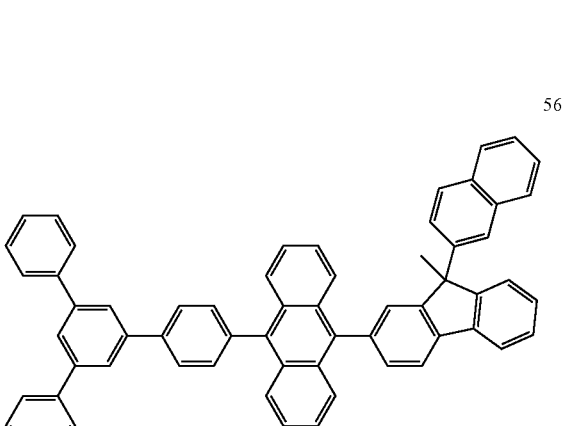
57
58
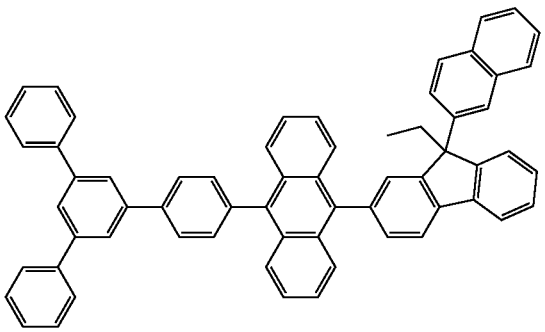

59
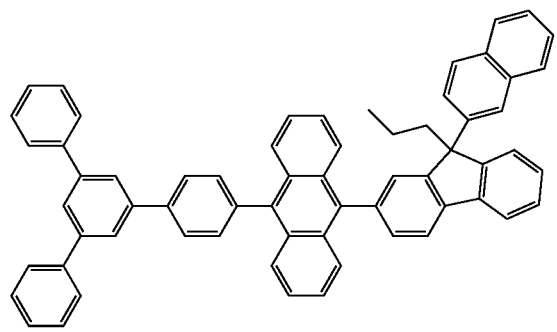
63
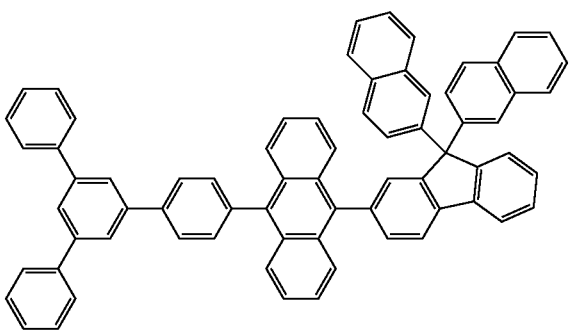
60
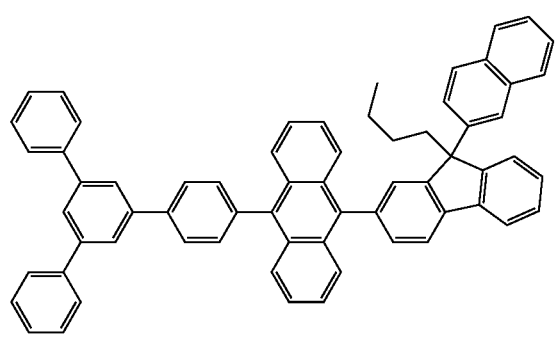
64
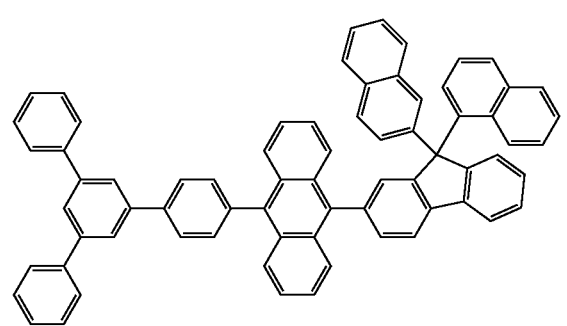
61
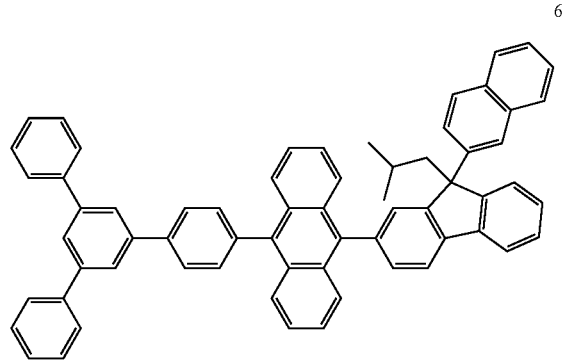
65
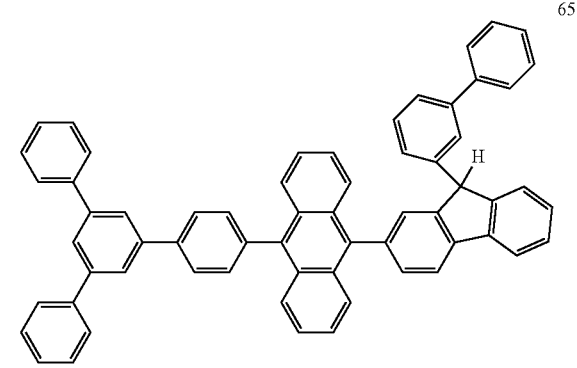
62
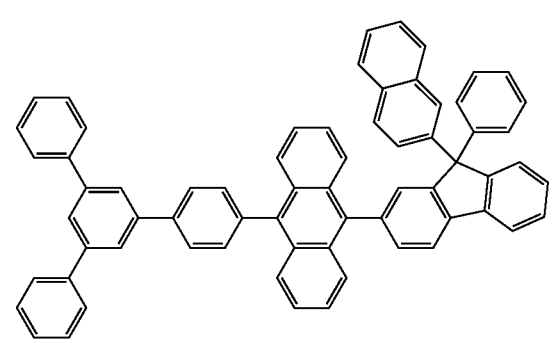
66
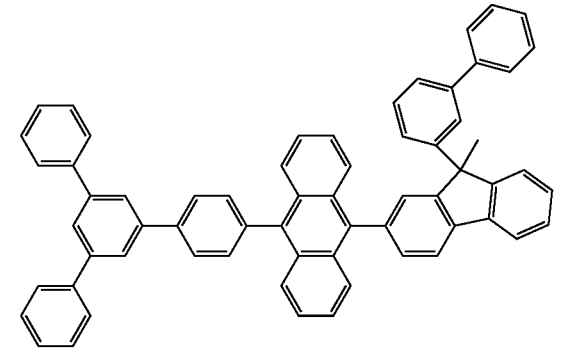

67
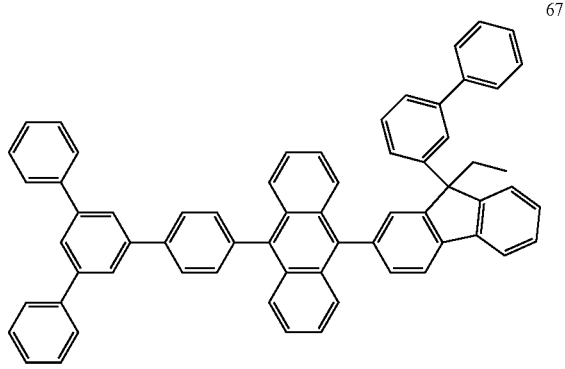
68
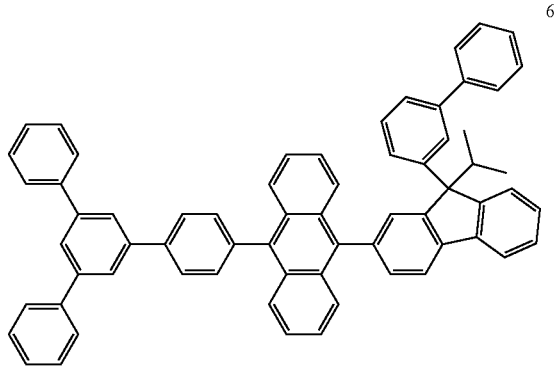
69
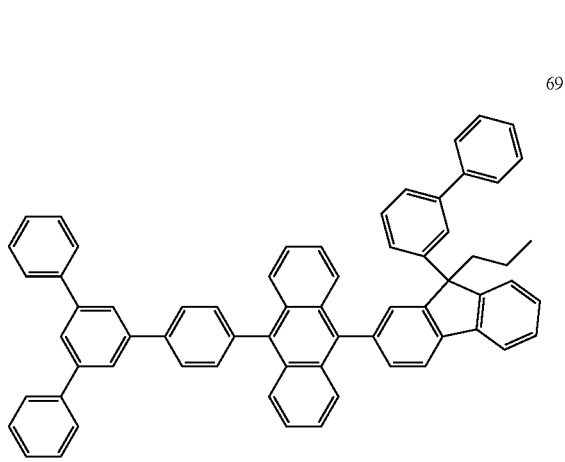
70
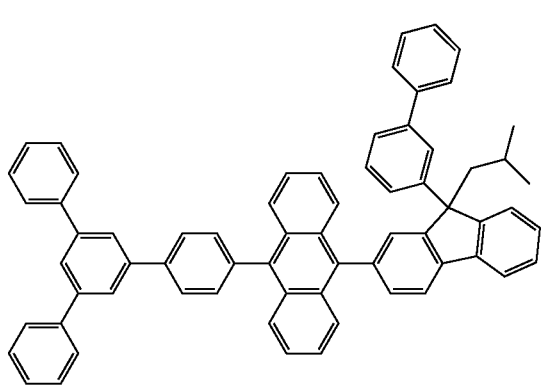
71
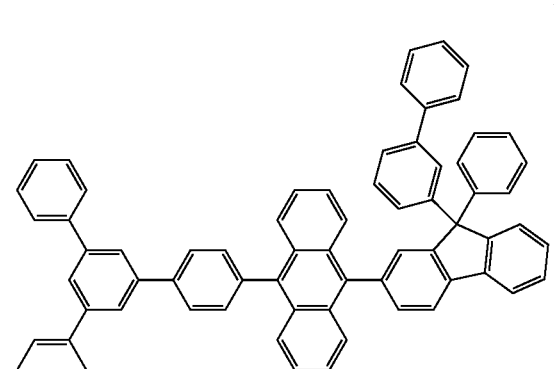
72
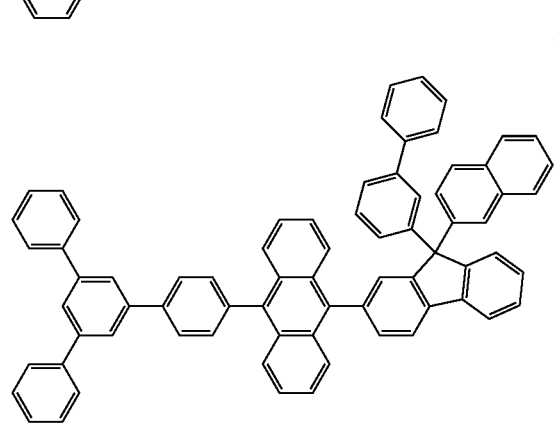
73
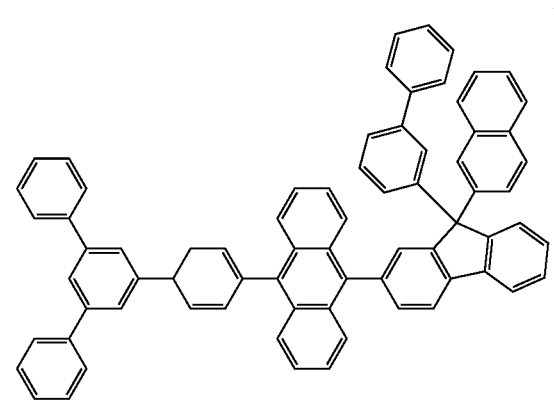
74
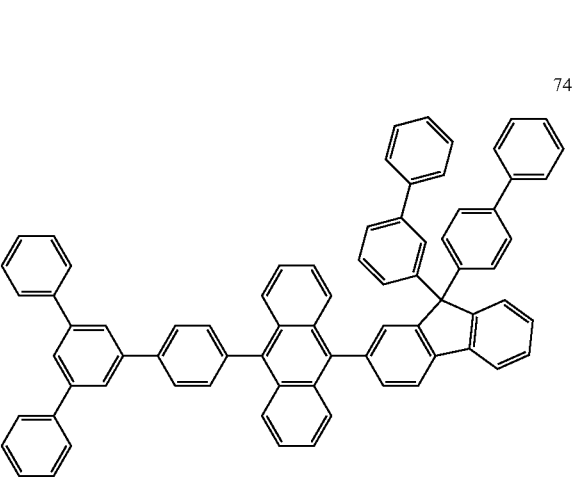

75
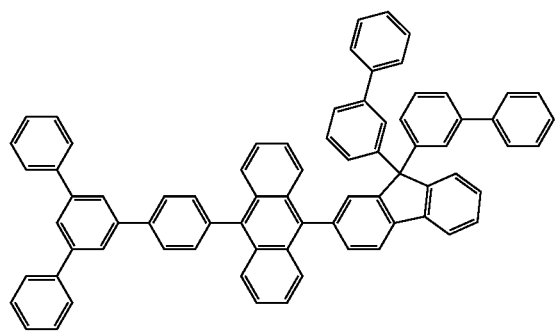
76
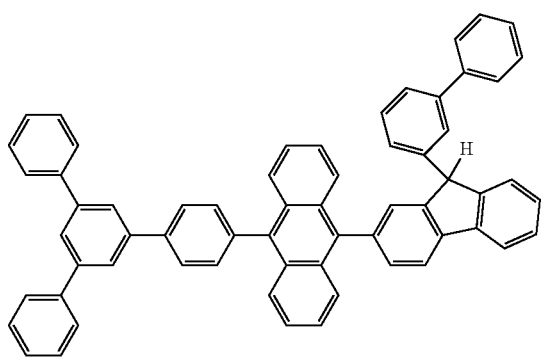
77
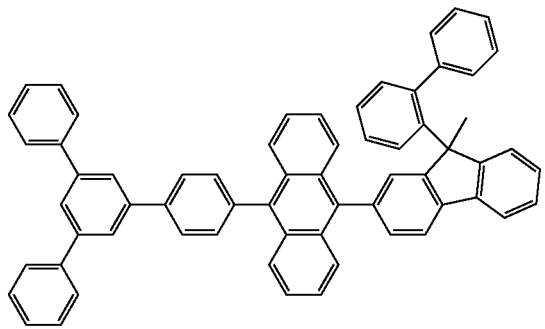
78
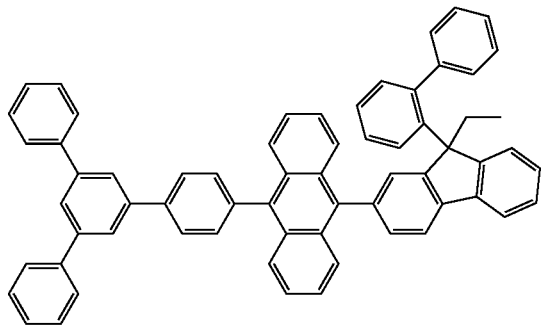
79
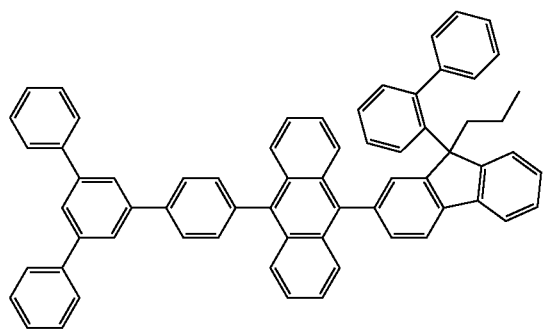
80
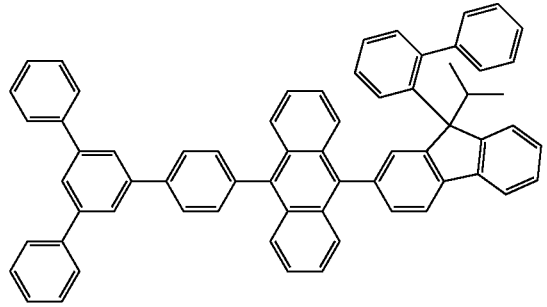
81
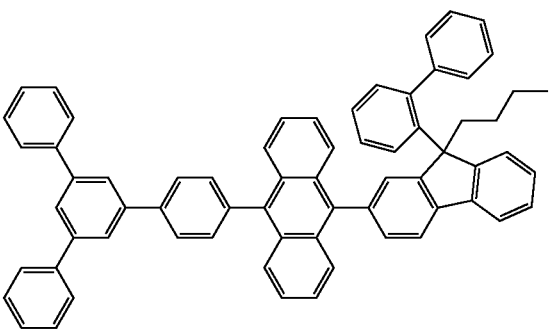
82
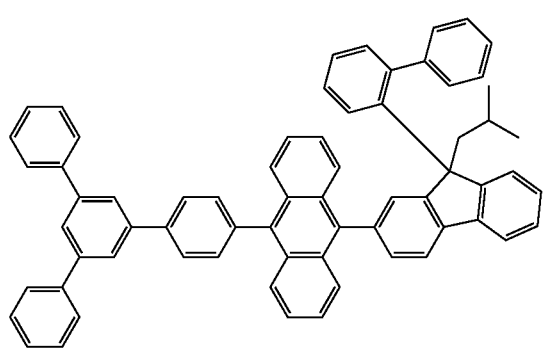

83
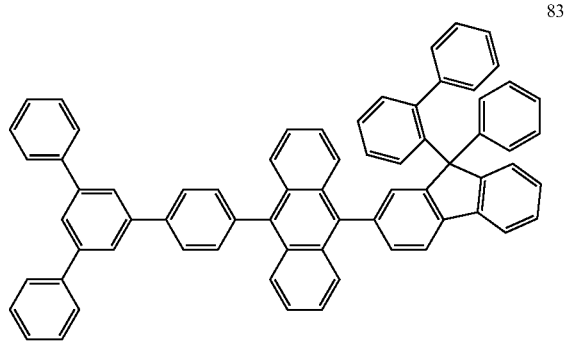
84
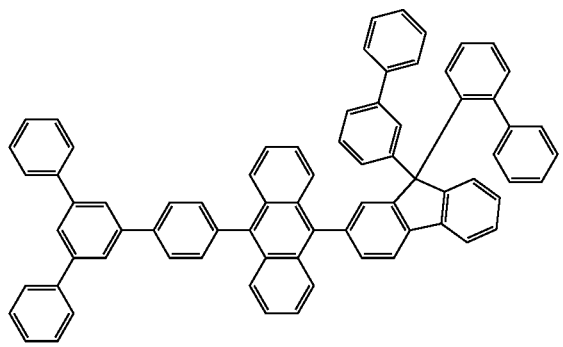
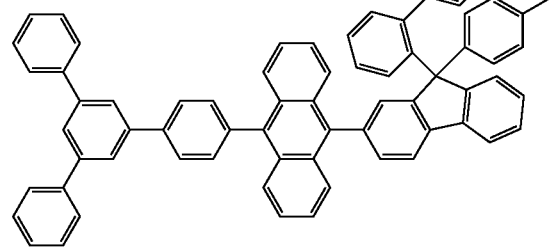
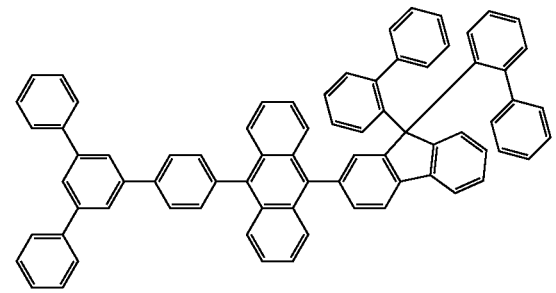
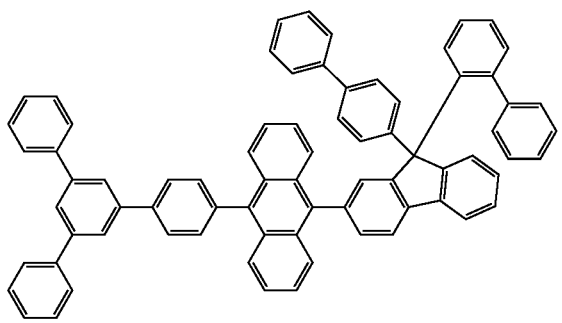
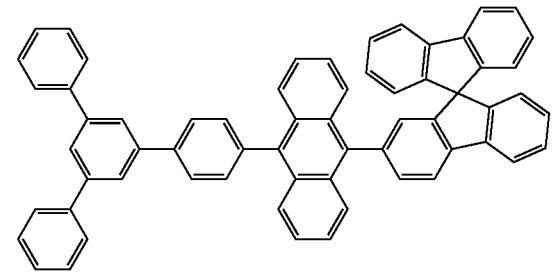
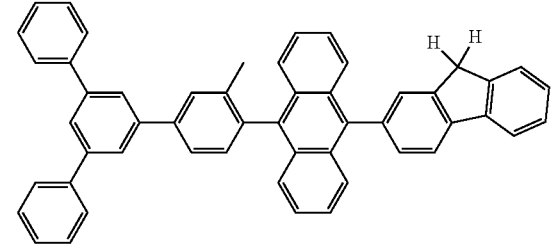

186
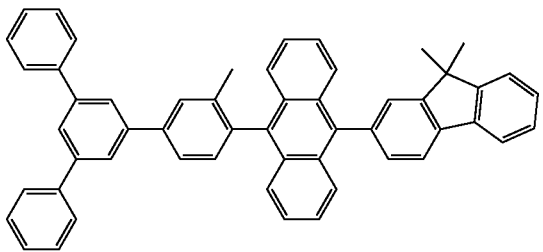
187
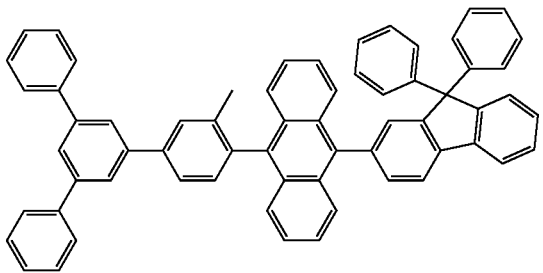
188
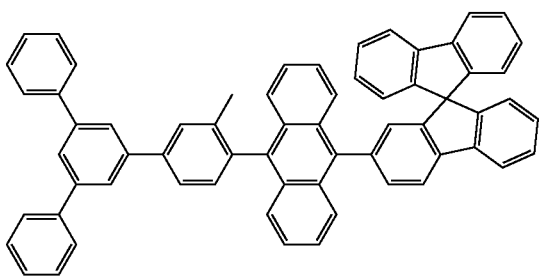
189
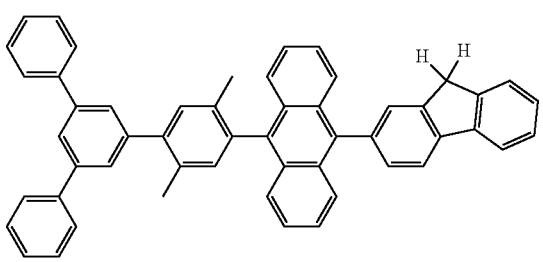
190
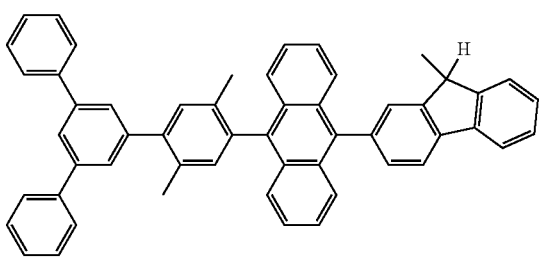
191
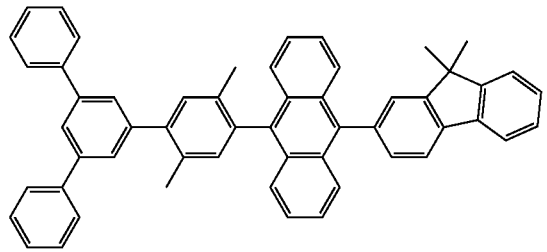
192
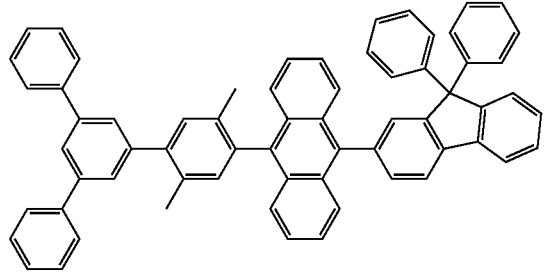
193
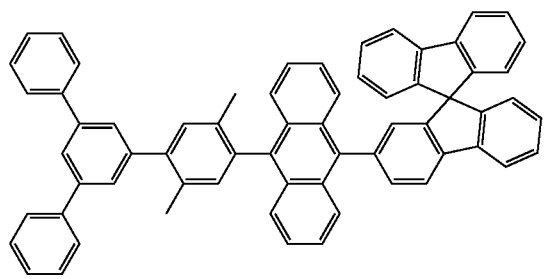
194
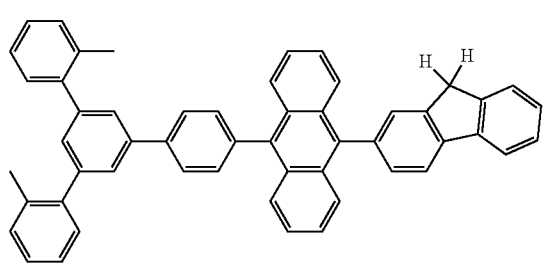
195
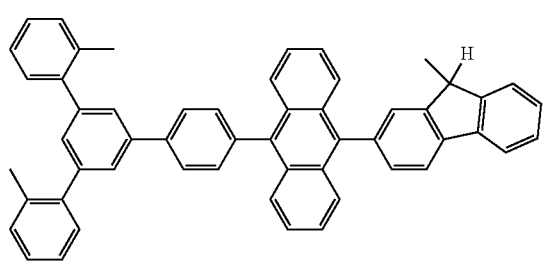

196
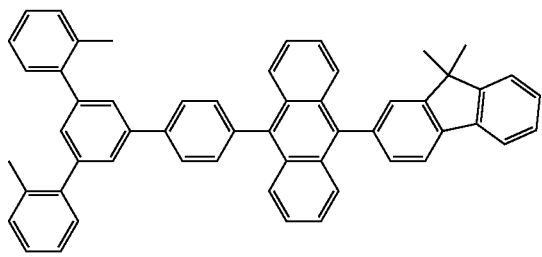
197
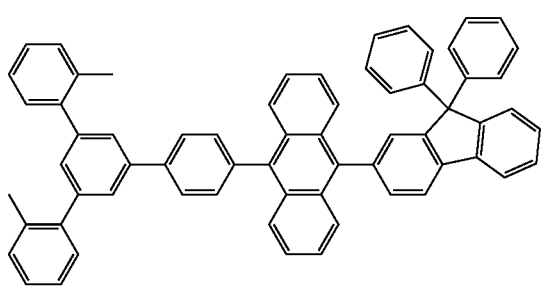
198
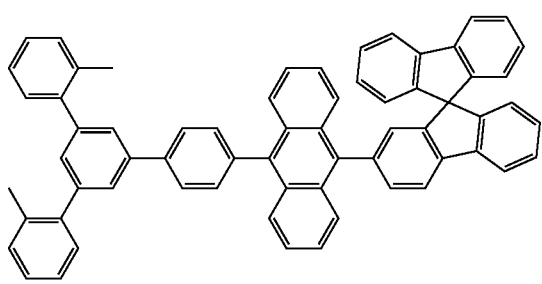
199
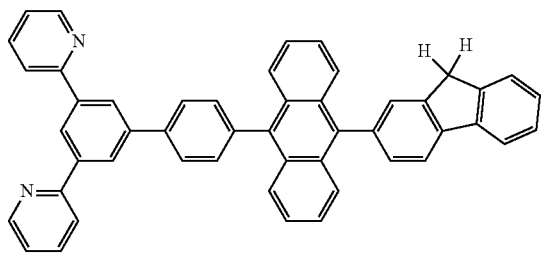
200
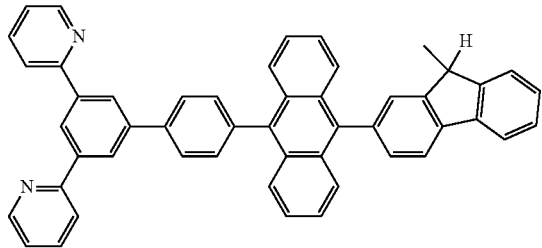
201
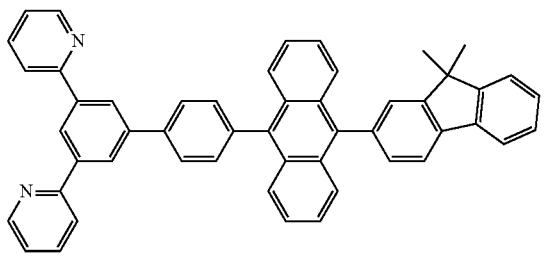
202
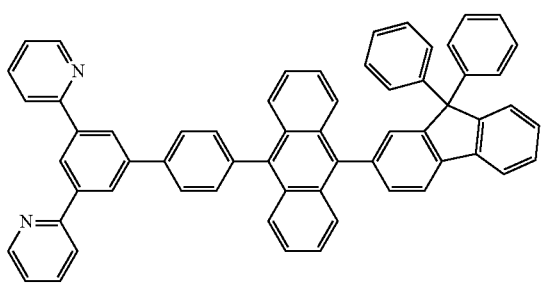
203
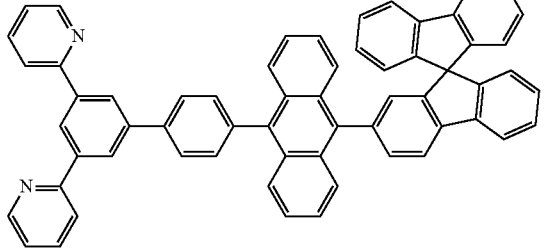
204
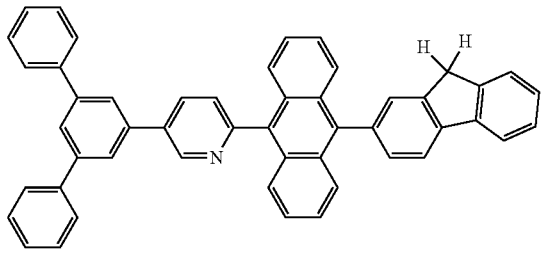
205
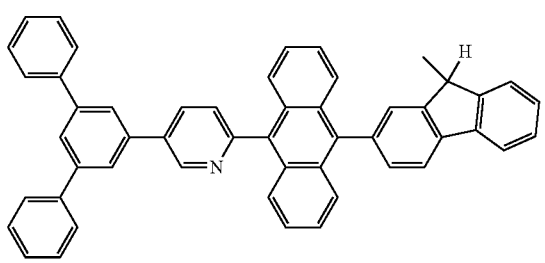

206
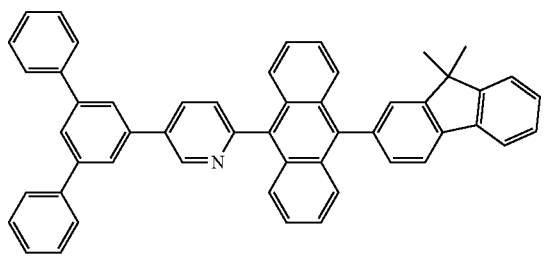
207
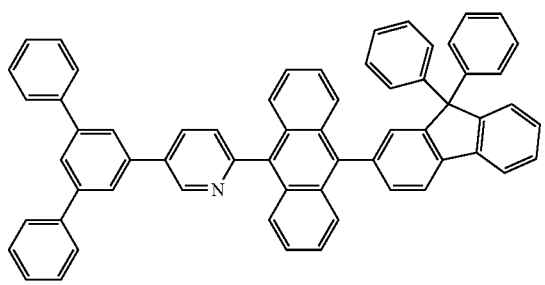
208
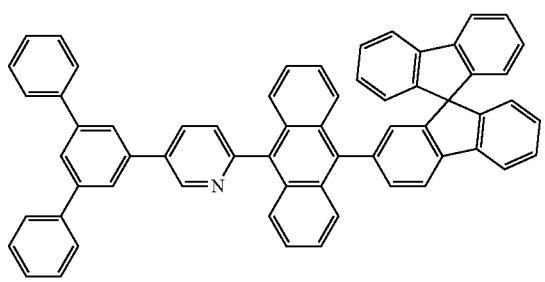
209
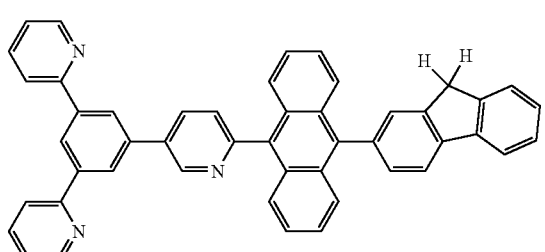
210
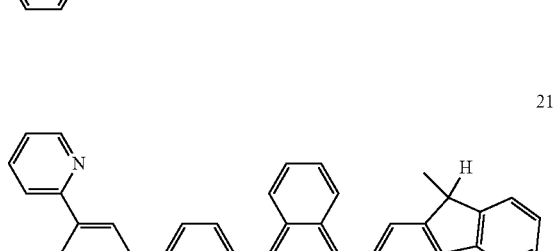
211
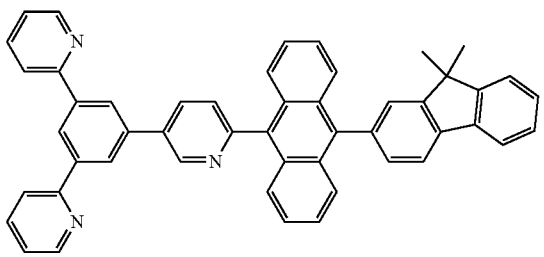
212
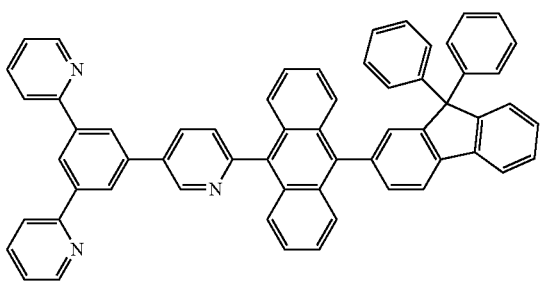
213
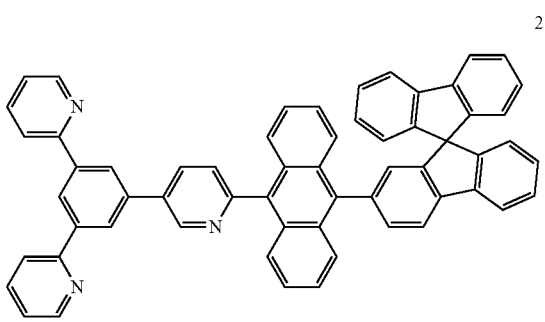
219
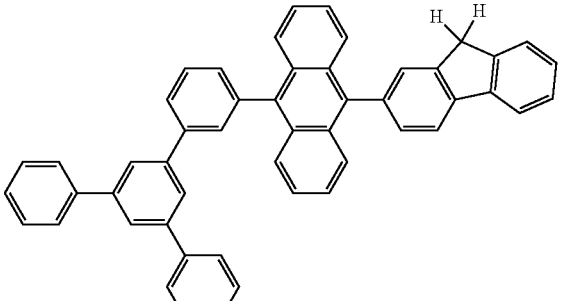
220
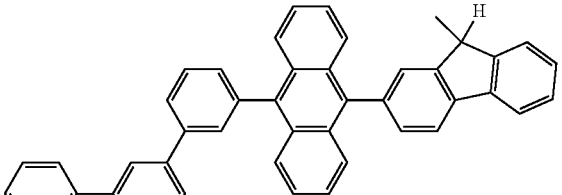

-continued
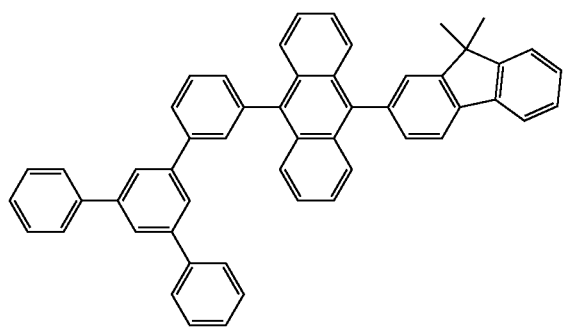
221
222
223
6. The organic electronic material according to claim 5, wherein its structure is as follows:
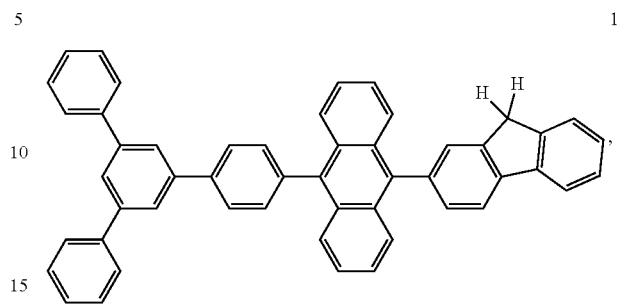
1
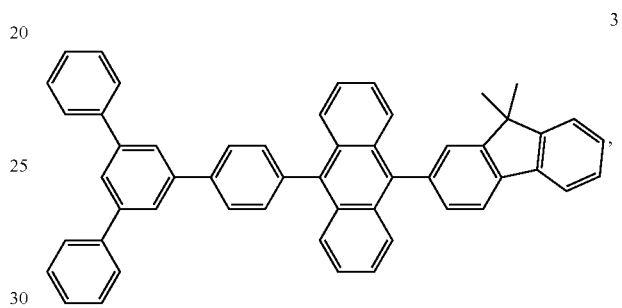
3
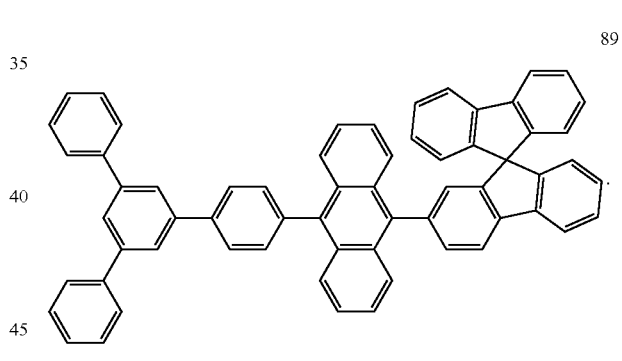
89
* * * * *